(12) United States Patent
Wang et al.

(10) Patent No.: US 11,445,905 B2
(45) Date of Patent: Sep. 20, 2022

(54) HETEROGENEOUS VISUAL ACUITY CHART AND VISUAL ACUITY TESTING METHOD AND DEVICE

(71) Applicant: QINGDAO UNIVERSITY, Qingdao (CN)

(72) Inventors: Lan Wang, Qingdao (CN); Yixiang Yuan, Qingdao (CN); Jason Yang Xue, Arcadia, CA (US); Judy Danley, Jamestown, NC (US); Xingcai Li, Qingdao (CN)

( * ) Notice: Subject to any disclaimer, the term of this patent is extended or adjusted under 35 U.S.C. 154(b) by 0 days.

(21) Appl. No.: 17/614,562

(22) PCT Filed: Jun. 22, 2020

(86) PCT No.: PCT/CN2020/097325
§ 371 (c)(1),
(2) Date: Nov. 29, 2021

(87) PCT Pub. No.: WO2021/004258
PCT Pub. Date: Jan. 14, 2021

(65) Prior Publication Data
US 2022/0218194 A1    Jul. 14, 2022

(30) Foreign Application Priority Data

Jul. 5, 2019 (CN) .......................... 201910605759.5
Jul. 5, 2019 (CN) .......................... 201910605772.0

(51) Int. Cl.
*A61B 3/032* (2006.01)
*A61B 3/00* (2006.01)

(52) U.S. Cl.
CPC ............ *A61B 3/032* (2013.01); *A61B 3/0041* (2013.01)

(58) Field of Classification Search
CPC .............................. A61B 3/032; A61B 3/0041
(Continued)

(56) References Cited

U.S. PATENT DOCUMENTS

2016/0095513 A1    4/2016   Shapiro et al.
2018/0296089 A1*  10/2018   Carson .................. A61B 3/032
2019/0038125 A1*   2/2019   Lesmes .................. A61B 3/032

FOREIGN PATENT DOCUMENTS

CN        102397053 A      4/2012
CN        203408028 U      1/2014
(Continued)

OTHER PUBLICATIONS

Bing Xu, Equal Visual Effect Visual Standard Pseudo-visual Acuity Chart, China Academic Journal Electronic Publishing House, 1994, pp. 377-378.
(Continued)

*Primary Examiner* — Mohammed A Hasan
(74) *Attorney, Agent, or Firm* — Bayramoglu Law Offices LLC

(57) ABSTRACT

A heterogeneous visual acuity chart and a visual acuity testing method and device are provided. The heterogeneous visual acuity chart is a size illusion chart composed of a heterogeneous reference zone and at least two types of optotypes of different sizes, where the heterogeneous reference zone is used to cause incorrect identification on the different types of optotypes of different sizes. The visual acuity testing method and device determine whether a visual acuity of a subject is true based on a difference between visual acuities tested with the heterogeneous visual acuity chart and a standard logarithmic visual acuity chart. The visual acuity chart is a size illusion chart composed of optotypes of different sizes and a perspective, which causes an illusion on a visual depth to interfere with the identification of the optotypes of different sizes.

23 Claims, 14 Drawing Sheets

(58) Field of Classification Search
USPC .......................................................... 351/239
See application file for complete search history.

(56) References Cited

FOREIGN PATENT DOCUMENTS

| | | |
|---|---|---|
| CN | 203468585 U | 3/2014 |
| CN | 204337251 U | 5/2015 |
| CN | 206342458 U | 7/2017 |
| CN | 108478185 A | 9/2018 |
| CN | 208404524 U | 1/2019 |
| CN | 110236481 A | 9/2019 |
| CN | 110313887 A | 10/2019 |
| JP | 2006014766 A | 1/2006 |

OTHER PUBLICATIONS

GB11533-2011, Standard for logarithmic visual acuity charts, Ministry of Health of the People's Republic of China China National Standardization Management Committee, 2011.

* cited by examiner

HETEROGENEOUS VISUAL ACUITY CHART AND VISUAL ACUITY TESTING METHOD AND DEVICE

CROSS REFERENCE TO THE RELATED APPLICATIONS

This application is the national phase entry of International Application No. PCT/CN2020/097325, filed on Jun. 22, 2020, which is based upon and claims priority to Chinese Patent Application No. 201910605759.5, filed on Jul. 5, 2019, and Chinese Patent Application No. 201910605772.0, filed on Jul. 5, 2019, the entire contents of which are incorporated herein by reference.

TECHNICAL FIELD

The present disclosure belongs to the technical field of visual acuity testing, and in particular relates to a heterogeneous visual acuity chart and a visual acuity testing method and device.

BACKGROUND

Visual acuity is one of the commonly used indicators of human function states. In China, visual acuity is usually tested in accordance with the *GB* 11533 *Standard for Logarithmic Visual Acuity Charts*. However, the visual acuity testing process has the following problems.

(1) The visual acuity test result relies on the subjective cooperation and statement of the subject, which may not be true. The subject is tested with a conventional visual acuity chart at a standard test distance of 5 m, and the subject is considered to have a visual acuity if he/she can correctly identify more than half of the smallest optotypes. The best subjective visual acuity of the subject defaults as a true visual acuity. Since the testing process is highly dependent on subjective cooperation and statement, and the directions and order of the optotypes in the visual acuity chart are fixed, if the subjective statement of the subject is not true, the test result cannot reflect a true visual acuity. For example, in order to meet the visual acuity requirements for entering school, enlisting in the army or working, etc., a subject may memorize the directions of 1 to 2 rows of optotypes that indicate a high visual acuity so as to obtain a tested high visual acuity. For another example, in a criminal judgment, a victim may falsely claim that he/she can only identify optotypes of a low visual acuity so as to pretend he/she has a low visual acuity, resulting in a false identification, eventually obtaining more compensation or aggravate the punishment for the offender. To prevent a subject from feigning a high visual acuity by memorizing the order of the optotypes, the structure of the visual acuity chart, the test distance, and the sizes and directions of the optotypes may be changed. However, the perceptual system can estimate the sizes and the distance of the optotypes to feign a low visual acuity. It is hard to effectively identify a feigned low visual acuity, which is still a key problem in visual acuity testing. Even if an unexplainable low visual acuity is found or a feigned low visual acuity is suspected, it is hard to make a definite judgement and conclusion due to a lack of basis, and a false result may be adopted.

(2) The visual acuity testing methods are inconsistent, and the low visual acuity tests have large errors. In accordance with the *GB* 11533 *Standard for Logarithmic Visual Acuity Charts*, there are 2 to 8 optotypes in each row in the visual acuity chart, and the subject is deemed to have a visual acuity if he/she can correctly identify more than half of a total number of optotypes. The number of optotypes used in actual tests is not uniform, especially in low visual acuity tests. Low visual acuity is one of the important visual function states, which is usually involved in social security, personal injury insurance claims and other social issues. In accordance with the *GB* 11533 *Standard for Logarithmic Visual Acuity Charts*, there are 2 to 4 optotypes to test a low visual acuity, resulting in a large error in low visual acuity testing.

SUMMARY

In order to overcome the above-mentioned shortcomings of the existing visual acuity testing process, such as difficulty in determining the authenticity of visual acuity test results and large errors in low visual acuity tests, the present disclosure provides a heterogeneous visual acuity chart and a visual acuity testing method and device. The present disclosure adopts a visual acuity chart that is a size illusion chart composed of optotypes of different sizes and a perspective. By frequently changing the structure of the visual acuity chart to test a subject, the present disclosure can obtain a true visual acuity of the subject, and can effectively identify a feigned visual acuity, especially a feigned low visual acuity.

Visual acuity is the ability of people to perceive the size of external objects, which is affected by external sensory stimuli and internal cognitive processes. These cognitive processes are affected by factors such as past experience and memory. When a subject is tested with a conventional visual acuity chart, the subject may feign a visual acuity based on the special perception of the size of objects. Visual illusion is a wrong determination and perception that people make based on empiricism or improper references when they observe an object. The present disclosure adopts a visual acuity chart is a size illusion chart composed of optotypes of different sizes and a perspective. The visual acuity chart causes an illusion on a visual depth to interfere with the identification of the optotypes of different sizes, so as to identify a feigned visual acuity, without affecting the identification of a true visual acuity.

In order to achieve the above objective, the present disclosure provides a heterogeneous visual acuity chart. The heterogeneous visual acuity chart is a size illusion chart composed of a heterogeneous reference zone and at least two types of optotypes of different sizes, where the heterogeneous reference zone is used to cause incorrect identification on the different types of optotypes of different sizes, that is, to make a small-sized type of optotype visually appear not to be smaller than a large-sized type of optotype.

Preferably, the heterogeneous reference zone may be a perspective that affects a visual depth of the optotypes of different sizes; M large-sized optotypes may be provided in visually nearer positions in the perspective, and N small-sized optotypes may be provided in visually farther positions in the perspective, M and N being positive integers $\geq 1$; and the incorrect identification on the different types of optotypes of different sizes may be caused by causing an illusion on the visual depth.

Preferably, the perspective that affects the visual depth of the optotypes of different sizes may be a background part in a size constancy illusion chart; for example, the perspective may be defined by grid patterns composed of first lines, second lines and third lines; and multiple first lines may be concentrated at one point along a depth direction, multiple second lines parallel to each other intersect the first lines in a horizontal direction, and multiple third lines parallel to each other intersect the first lines in a vertical direction.

Preferably, the heterogeneous reference zone may further include an illusion pattern that makes a small-sized optotype visually larger and a large-sized optotype visually smaller; and the illusion pattern may include, but may be not limited to, a pattern to realize an illusion function, such as a letter, a number, a geometric structure and a cone. Preferably, a letter pattern may be an optotype pattern with the same structure as the optotype.

Preferably, a color block may be further provided between two different sets of optotypes in the heterogeneous reference zone; and the color block may separate the two sets of optotypes, which are connected, so as to form a partition visually.

When there are two types of optotypes, there may be multiple small-sized optotypes in a first type and multiple large-sized optotypes in a second type; a size of each of the optotypes in the first type may be 0.64-0.99 times that of each of the optotypes in the second type; a blank distance between each of the optotypes in each of the types and a surrounding line or illusion pattern that defines the heterogeneous reference zone may be more than half of a width of the optotype; a blank distance between optotypes of the two types that may be adjacent may be more than half of a width of the large-sized optotype; and there may be at least five optotypes in four directions in each of the two types, and the directions of two adjacent optotypes may be different. Specifically, the heterogeneous reference zone may include a first type of optotype pattern and a second type of optotype pattern that have the same structure as the optotypes; the first type of optotype pattern and the second type of optotype pattern may be respectively provided around the first type of optotypes and the second type of optotypes; a size of the first type of optotype pattern may be not more than 0.5 times that of the first type of optotypes, and a size of the second type of optotype pattern may be not less than 1.5 times that of the second type of optotypes; and an Ebbinghaus illusion may be caused to make the first type of optotypes appear larger visually and the second type of optotypes appear smaller visually, so as to affect normal identification on the sizes of the optotypes. Specifically, the optotype pattern may be an E-type optotype pattern and a C-type optotype pattern, which have the same principle. A cone may be provided between the two types of optotypes; and an apex of the cone may be near the first type of optotypes, and a bottom surface of the cone may be near the second type of optotypes.

Preferably, the size of the first type of optotypes may be 0.79-0.81 times that of the second type of optotypes.

In order to achieve the above objective, the present disclosure provides a visual acuity testing method, which includes the following steps:

performing a visual acuity test with the heterogeneous visual acuity chart; moving a testing heterogeneous visual acuity chart from far to near or from near to far relative to a subject so as to change a test distance between the subject and the testing heterogeneous visual acuity chart, until a number of optotypes, correctly identified by the subject, in any set of optotypes is less than half; and recording the number of correctly identified optotypes in each of the two types in the heterogeneous visual acuity chart, calculating and recording a tested visual acuity;

performing a standard visual acuity test with a standard logarithmic visual acuity chart, where the subject is in a test distance from a testing standard logarithmic visual acuity chart, and recording a tested visual acuity; and testing with the heterogeneous visual acuity chart for ≥1 time for the same subject, and determining whether a visual acuity of the subject is true according to a difference between visual acuities tested with the heterogeneous visual acuity chart and a difference between visual acuities tested with the heterogeneous visual acuity chart and the standard logarithmic visual acuity chart. Specifically, the determining whether a visual acuity of the subject is true includes:

defining a row of the standard logarithmic visual acuity chart as a standard visual acuity row;

determining that a visual acuity tested with the standard logarithmic visual acuity chart is true if these differences are all within one standard visual acuity row, that is, the differences ≤1 standard visual acuity row;

determining that the subject is uncooperative and the visual acuity tested with the standard logarithmic visual acuity chart is false, if one of these differences reaches two standard visual acuity rows or more, that is, the difference ≥2 standard visual acuity rows, or the subject does not cooperate to complete the test; and determining that the subject is likely to be subjectively uncooperative and the visual acuity tested with the standard logarithmic visual acuity chart is likely to be false, if, although these differences do not reach two standard visual acuity rows, when tested with the heterogeneous visual acuity chart, the subject correctly identifies an optotype in the first type but fails to correctly identify an optotype in the second type, or there is a contradiction hard to be explained reasonably between the tested visual acuities.

Further, the visual acuity testing method may further include: performing a visual acuity test with a single visual acuity chart; moving a testing single visual acuity chart relative to a subject from far to near so as to change a test distance between the subject and the testing single visual acuity chart, until a farthest distance where the subject correctly identifies more than half of the optotypes; and calculating and recording a tested visual acuity;

where, the single visual acuity chart is a plan composed of at least five optotypes of the same size; there are four optotype directions in the visual acuity chart; a blank distance between any two adjacent optotypes is more than half of a width of each of the optotypes; and the directions of any two adjacent optotypes in a vertical direction are different, and the directions of any two adjacent optotypes in a horizontal direction are also different; and testing with the heterogeneous visual acuity chart and the single visual acuity chart each for ≥1 time for the same subject, and determining whether a visual acuity of the subject is true according to a difference between visual acuities tested with the heterogeneous visual acuity chart, a difference between visual acuities tested with the single visual acuity chart, a difference between visual acuities tested with the heterogeneous visual acuity chart and the single visual acuity chart and a difference between visual acuities tested with the single visual acuity chart and a standard logarithmic visual acuity chart, where specifically, the determining whether a visual acuity of the subject is true may include:

defining a row of the standard logarithmic visual acuity chart as a standard visual acuity row;

determining that a visual acuity tested with the standard logarithmic visual acuity chart is true if these differences are all within one standard visual acuity row, that is, the differences ≤1 standard visual acuity row;

determining that the subject is uncooperative and the visual acuity tested with the standard logarithmic visual acuity chart is false, if one of these differences reaches two standard visual acuity rows or more, that is, the difference ≥2 standard visual acuity rows, or the subject does not cooperate to complete the test; and determining that the subject is likely to be subjectively uncooperative and the visual acuity tested with the standard logarithmic visual acuity chart is likely to be false, if, although these differences do not reach two standard visual acuity rows, when tested with the heterogeneous visual acuity chart, the subject correctly identifies an optotype in the first type but fails to correctly identify an optotype in the second type, or there is a contradiction hard to be explained reasonably between the tested visual acuities.

In order to achieve the above objective, the present disclosure provides a visual acuity testing device. The visual acuity testing device includes a distance measuring device, a visual acuity chart mounting and adjustment device and a visual acuity chart support device, where the visual acuity chart mounting and adjustment device is fixed on the visual acuity chart support device, for changing and displaying different visual acuity charts; the distance measuring device is used to measure a distance between a subject and a testing visual acuity chart; the testing visual acuity chart is defined by each of the visual acuity charts or an image thereof in a mirror; and the visual acuity charts include a heterogeneous visual acuity chart, a standard logarithmic visual acuity chart and a single visual acuity chart.

Further, the visual acuity chart support device may be specifically a first support device; each of the visual acuity charts may be detachably provided on a support plate of the first support device; and each of the visual acuity charts serves as the testing visual acuity chart.

Further, the visual acuity chart support device may be specifically a first support device; the visual acuity testing device may further include a second support device and a mirror; the visual acuity charts may be detachably provided on the first support device; the first support device may be provided opposite to the second support device; the mirror may be provided on the second support device, such that the mirror may be opposite to the heterogeneous visual acuity chart or the standard logarithmic visual acuity chart; and the testing visual acuity chart may be defined by an image of the visual acuity chart in the mirror.

Further, the visual acuity testing device may further include a moving device, which may be used to realize relative movement between the testing visual acuity chart and the subject.

Further, the visual acuity chart mounting and adjustment device may include first magnets and second magnets that may be mutually attracted; the first magnets may be fixedly provided on the heterogeneous visual acuity chart, the standard logarithmic visual acuity chart and the single visual acuity chart; and the second magnets may be provided on the support plate of the first support device.

Further, the visual acuity chart support device may be specifically a first support device; the visual acuity chart mounting and adjustment device may include a control unit and a visual acuity chart display screen and a visual acuity result display screen that may be connected to the control unit; the visual acuity chart display screen may be provided on the first support device; the control unit may be provided with a data storage module, a visual acuity chart selection module, a heterogeneous visual acuity chart generation module for generating the heterogeneous visual acuity chart, a standard visual acuity chart generation module for generating the standard logarithmic visual acuity chart, a single visual acuity chart generation module for generating the single visual acuity chart and a visual acuity calculation module for calculating a visual acuity; and the visual acuity chart calculation module, the visual acuity chart selection module, the heterogeneous visual acuity chart generation module, the single visual acuity chart generation module and the standard visual acuity chart generation module may be respectively connected to the data storage module.

The distance measuring device may be a displacement sensor, which may be provided on the first support device and connected to the control unit.

Further, the visual acuity testing device may include a smart moving device, an optotype indicating module and an optotype identifying device; the smart moving device may include a wheel at a bottom of the first support device, a drive motor connected to the wheel and a brake on the wheel; the drive motor and the brake may be respectively connected to a drive module in the control unit; the optotype indicating module may be used to indicate optotypes to be identified by the subject; the optotype identifying device may be used to confirm the start of identifying the optotypes and input an identification result on the optotypes to be identified; and the drive module, the optotype indicating module and the optotype identifying device may be respectively connected to the data storage module.

Further, the control unit may include a feigned visual acuity determination module; the feigned visual acuity determination module may be connected to the data storage module; and the feigned visual acuity determination module may be used to obtain visual acuities tested with the single visual acuity chart, the heterogeneous visual acuity chart and the standard logarithmic visual acuity chart from the data storage module, compare multiple visual acuities to determine whether a visual acuity may be false, send a determination result to the data storage module for storage, and send the determination result on the subject to the visual acuity result display screen for display.

Further, the control unit may include an optotype size setting module for setting the size of the optotypes; and the optotype size setting module may be connected to the heterogeneous visual acuity chart generation module, the single visual acuity chart generation module and the standard visual acuity chart generation module, respectively.

Further, the control unit may include an optotype direction setting module for setting optotype directions; and the optotype direction setting module may be connected to the heterogeneous visual acuity chart generation module, the single visual acuity chart generation module and the standard visual acuity chart generation module, respectively.

Further, the control unit may include an optotype arrangement setting module for arranging optotype positions; and the optotype arrangement setting module may be connected to the heterogeneous visual acuity chart generation module, the single visual acuity chart generation module and the standard visual acuity chart generation module, respectively.

Compared with the prior art, the present disclosure has the following advantages and positive effects.

(1) The heterogeneous visual acuity chart of the present disclosure is composed of at least two types of optotypes of different sizes. When there are two types of optotypes, the size of the small-sized optotype is 0.64-0.99 times that of the large-sized optotype. When the test distance between the heterogeneous visual acuity chart and the subject is one at which the subject can correctly identify the small-sized optotype, the subject can also correctly identify the large-sized optotype at the same time. If the subject subjectively states that he/she can correctly identify the small-sized optotype but cannot correctly identify the large-sized optotype, the identification is abnormal, prompting that the subject's statement is false and warning that the subject is subjectively uncooperative and feigns a visual acuity.

(2) The heterogeneous visual acuity chart of the present disclosure is a size illusion chart composed of a heterogeneous reference zone and at least two types of optotypes of different sizes. The heterogeneous visual acuity chart includes at least two types of optotypes of different sizes. When the test distance between the heterogeneous visual acuity chart and the subject is a farthest distance at which the subject can identify the large-sized optotype, the small-sized optotype exceeds the subject's visual acuity and cannot be correctly identified. By designing the at least two types of optotypes, the present disclosure improves the test accuracy.

(3) In the heterogeneous visual acuity chart of the present disclosure, at least two types of optotypes of different sizes are provided in the heterogeneous reference zone that is provided with multiple sets of patterns composed of lines, which makes the small-sized optotype not to appear visually smaller than the large-sized optotype. During testing, the at least two types of optotypes of different sizes are easily confused by the subject to cause incorrect identification of the subject on the size of the optotype, thereby preventing the subject from feigning and improving the test accuracy. In addition, there may be another identification abnormality during the test with the heterogeneous visual acuity chart. That is, in the same test with the same heterogeneous visual acuity chart, the visual acuity results obtained from two test distances cannot be explained reasonably. For example, optotypes 0.8 and 0.888 are correctly identified at 2.48 m, but optotypes 0.8 and 0.888 are not identified at 2.68 m, the visual acuities are 0.40 and 0.436, and the visual acuities are <0.429 and <0.472. The optotype 0.436 is seen clearly but the 0.429 optotype is not seen clearly, which cannot be explained reasonably, indicating that the subject lacks subjective cooperation.

(4) The visual acuity testing device of the present disclosure uses two different visual acuity charts, a heterogeneous visual acuity chart and a standard logarithmic visual acuity chart, for visual acuity testing. In the heterogeneous visual acuity chart, the at least two types of optotypes of different sizes are easily confused by the subject to cause incorrect identification of the subject on the size of the optotype, thereby preventing the subject from feigning and improving the test accuracy. The visual acuity testing device determines whether a visual acuity tested with the standard logarithmic visual acuity chart is true based on a difference between visual acuities tested with the heterogeneous visual acuity chart and the standard logarithmic visual acuity chart, thereby effectively identifying a feigned visual acuity so as to avoid a feigned high visual acuity.

(5) The visual acuity testing device of the present disclosure is further provided with a single visual acuity chart. The single visual acuity chart is used together with the heterogeneous visual acuity chart and the standard logarithmic visual acuity chart, and the visual acuity test is repeated many times to make the test result more accurate.

(6) The visual acuity testing device of the present disclosure is provided with a mobile support device and an optotype size setting module. The mobile support device is used to change the distance between the visual acuity chart and the subject, and the optotype size setting module is used to set the sizes of the optotypes. During visual acuity testing, the sizes of the optotypes and the test distances are different each time, and the test is repeated many times to make the test result more accurate. For example, the decimal visual acuity of a subject is 0.25, and the tested best subjective visual acuities of the subject are 0.3 at 4.4 m, 0.27 at 5 m, and 0.2 at 6.3 m, etc.

(7) The true visual acuity tested by the visual acuity testing device and method of the present disclosure is quantified by a minimum visual angle. The present disclosure adopts diversified tests without a memorable visual acuity chart structure. The subject can only rely on his true visual acuity to identify the smallest optotype, thereby preventing the subject from feigning a high visual acuity.

(8) A person to feign a low visual acuity typically chooses a lower visual acuity as his best subjective visual acuity, and his true visual acuity is higher than the best subjective visual acuity. During the multiple times of tests, the person needs to follow the standard logarithmic visual acuity chart structure to maintain the low visual acuity he/she chooses. In the visual acuity testing device and method of the present disclosure, the structures of the visual acuity charts are different, the sizes and directions of the optotypes are changing, and the test distances of the visual acuity charts are also changing. The person cannot always maintain the same false lower subjective visual acuity due to the changes in the visual acuity charts, the optotypes and the test distances. As a result, the best subjective visual acuity of the person changes continuously, which indicates that the person is subjectively uncooperative and feigns. In particular, when tested with the heterogeneous visual acuity chart, a person to feign a low visual acuity often chooses an optotype that appears to be larger visually, and there is often a contradiction that the person identifies a small-sized optotype but fails to identify a large-sized optotype, which is hard to explain reasonably. Therefore, the visual acuity testing method of the present disclosure can warn a potentially feigned low visual acuity.

(9) Because the visual acuity testing highly relies on the subjective cooperation of the subject, if the subject does not actively look at or identify the optotypes, the true visual acuity of the subject is hard to be obtained. If the best subjective visual acuities obtained through multiple tests are significantly different and violate the principle of repeatable visual acuity verification, it can be determined that the subject is subjectively uncooperative. The subjective non-cooperation conclusion made by the visual acuity testing device and method of the present disclosure is conforming to the rules of visual acuity testing, scientifically reliable, and completes the types of visual acuity test conclusions. The present disclosure can effectively prevent those to feign a visual acuity from obtaining improper benefits, and has positive and important practical significance.

(10) The visual acuity testing device and method of the present disclosure can also comprehensively adopt a variety of measures to prevent the subject from feigning, for example, to require the subject to close his eyes to rest at intervals so as to reduce his short-term memory of the optotype and distance, or to randomly use a visual acuity chart with different optotype directions so as to prevent the subject from memorizing the order of the optotypes.

(11) In the visual acuity testing device and method of the present disclosure, during visual acuity testing, the visual acuity chart, the size of the optotypes and the test distance (from near to far or from far to near) change each time. Alternatively, a standard test distance of 5 m is adopted, but the multiple tests are diversified so as to obtain the best subjective visual acuity. The test results rely on true best visual acuities, and no visual acuity test conclusion will be made for those who are subjectively uncooperative, so the visual acuity conclusion is true and reliable.

DETAILED DESCRIPTION OF THE EMBODIMENTS

Figure 1:
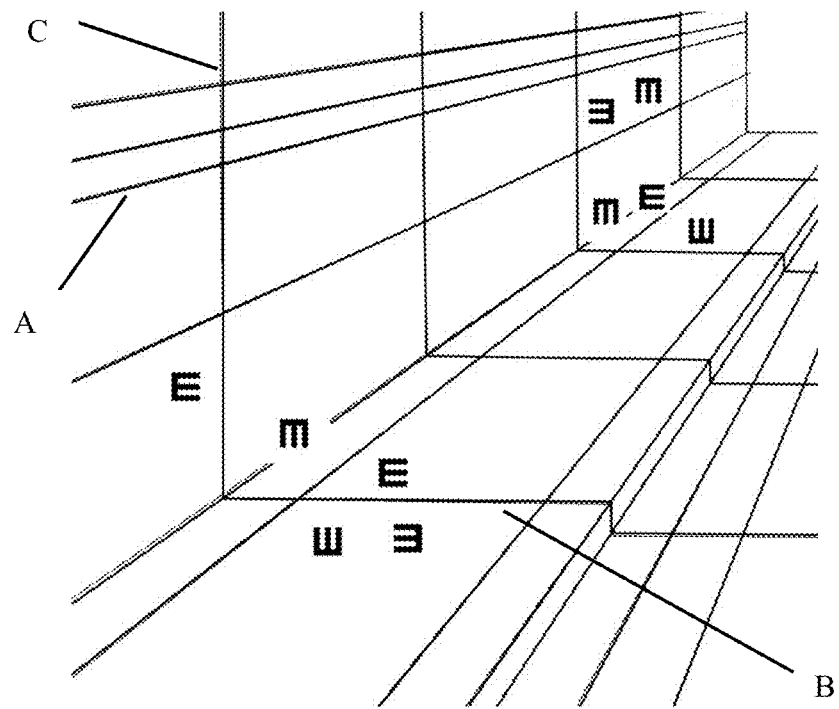
FIGS. 1 to 21 are views illustrating structures of heterogeneous visual acuity charts according to Embodiments 1 to 21 of the present disclosure.

The present disclosure is described in detail below with reference to the illustrative implementations. However, it should be understood that without further description, elements, structures and features in one embodiment may also be beneficially combined into other embodiments.

In the description of the present disclosure, it should be noted that orientations or positional relationships indicated by the terms such as "upper", "lower", "left" and "right" are all based on what are illustrated in the drawings, and such terms are used herein for ease and simplification of description of the present disclosure rather than indicating or implying that the stated device or element must have a specific orientation or must be constructed and operated in a specific orientation, and thus cannot be construed as a limitation to the present disclosure. Moreover, terms such as "first" and "second" are merely intended for the purpose of description, and should not be construed as indicating or implying relative importance.

The present disclosure provides a heterogeneous visual acuity chart. The heterogeneous visual acuity chart is a size illusion chart composed of a heterogeneous reference zone and at least two types of optotypes of different sizes, where the heterogeneous reference zone is used to cause incorrect identification on the different types of optotypes of different sizes, that is, to make a small-sized type of optotype visually appear not to be smaller than a large-sized type of optotype.

Preferably, the heterogeneous reference zone is a perspective that affects a visual depth of the optotypes of different sizes; M large-sized optotypes are provided in visually nearer positions in the perspective, and N small-sized optotypes are provided in visually farther positions in the perspective, M and N being positive integers ≥1; and the incorrect identification on the different types of optotypes of different sizes is caused by causing an illusion on the visual depth.

Preferably, the perspective that affects the visual depth of the optotypes of different sizes is a background part in a size constancy illusion chart; for example, the perspective is defined by grid patterns composed of first lines, second lines and third lines; and multiple first lines are concentrated at one point along a depth direction, multiple second lines parallel to each other intersect the first lines in a horizontal direction, and multiple third lines parallel to each other intersect the first lines in a vertical direction.

Preferably, the heterogeneous reference zone further includes an illusion pattern that makes a small-sized optotype visually larger and a large-sized optotype visually smaller; and the illusion pattern includes, but is not limited to, a pattern to realize an illusion function, such as a letter, a number, a geometric structure and a cone. Preferably, a letter pattern is an optotype pattern with the same structure as the optotype.

Preferably, a color block is further provided between two different sets of optotypes in the heterogeneous reference zone; and the color block separates the two sets of optotypes, which are connected, so as to form a partition visually.

When there are two types of optotypes, there are multiple small-sized optotypes in a first type and multiple large-sized optotypes in a second type; a size of each of the optotypes in the first type is 0.64-0.99 times that of each of the optotypes in the second type; a blank distance between each of the optotypes in each of the types and a surrounding line or illusion pattern that defines the heterogeneous reference zone is more than half of a width the optotype; a blank distance between optotypes of the two types that are adjacent is more than half of a width of the large-sized optotype; and there are at least five optotypes in four directions in each of the two types, and the directions of two adjacent optotypes are different. Specifically, the heterogeneous reference zone includes a first type of optotype pattern and a second type of optotype pattern that have the same structure as the optotypes; the first type of optotype pattern and the second type of optotype pattern are respectively provided around the first type of optotypes and the second type of optotypes; a size of the first type of optotype pattern is not more than 0.5 times that of the first type of optotypes, and a size of the second type of optotype pattern is not less than 1.5 times that of the second type of optotypes; and an Ebbinghaus illusion is caused to make the first type of optotypes appear larger visually and the second type of optotypes appear smaller visually, so as to affect normal identification on the sizes of the optotypes. Specifically, the optotype pattern is an E-type optotype pattern and a C-type optotype pattern, which have the same principle. A cone is provided between the two types of optotypes; and an apex of the cone is near the first type of optotypes, and a bottom surface of the cone is near the second type of optotypes.

Preferably, the size of the first type of optotypes is 0.79-0.81 times that of the second type of optotypes.

Embodiment 1: The present disclosure provides a heterogeneous visual acuity chart. Referring to FIG. 1, the heterogeneous visual acuity chart includes two types of optotypes of different sizes and a perspective that affects a visual depth of the optotypes of different sizes. A first type of optotypes include five small-sized optotypes, and a second type of optotypes include five large-sized optotypes. The first type of optotypes and the second type of optotypes are provided in different positions. The perspective includes first lines A, second lines B and third lines C. Multiple first lines A are concentrated at one point along a depth direction. Multiple parallel second lines B intersect with the first lines A in a horizontal direction to form grid patterns which define a horizontal plane. Multiple parallel third lines C intersect with the first lines A in a vertical direction to form multiple grid patterns, which are arranged in order from large to small to define a vertical plane. The second lines B in the horizontal plane are connected to lower ends of the third lines C in the vertical plane, such that the horizontal plane and the vertical plane are connected to define a three-dimensional space. Specifically, the first type of optotypes are provided in an upper right zone of the heterogeneous visual acuity chart. Among the five optotypes of the first type, optotypes 1 and 2 are provided in the same grid pattern. An optotype 3 is provided in a grid pattern 3 on a lower right side of the grid pattern where the optotypes 1 and 2 are located. Optotypes 4 and 5 are provided between a grid pattern on a lower side of the grid pattern where the optotypes 1 and 2 are located and a grid pattern on a left side of the grid pattern where the optotype 3 is located. A blank distance between each of the optotypes and an edge of the grid pattern where the optotype is located is not less than half of a width of one optotype of the first type. A blank distance between two adjacent optotypes in the same grid pattern is not less than half of the width of one optotype of the first type. There are four optotype directions. The directions of the two optotypes in the same grid pattern are different, and the directions of any two adjacent optotypes are also different. The second type of optotypes are provided in a lower left zone of the heterogeneous visual acuity chart. Among the five optotypes of the second type, optotypes 1 and 2 are provided in the same grid pattern. An optotype 3 is provided in a grid pattern 1 on an upper right side of the grid pattern where the optotypes 1 and 2 are located. An optotype 4 is provided in a grid pattern 1 on an upper left side of a grid pattern on a left side of the grid pattern where the optotypes 1 and 2 are located. An optotype 5 is provided between a grid pattern 1 on an upper right side of the grid pattern where the optotype 4 is located and a grid pattern 1 on a left side of the grid pattern where the optotype 3 is located. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the two optotypes in the same grid pattern are different, and the directions of any two adjacent optotypes are also different.

Figure 2:
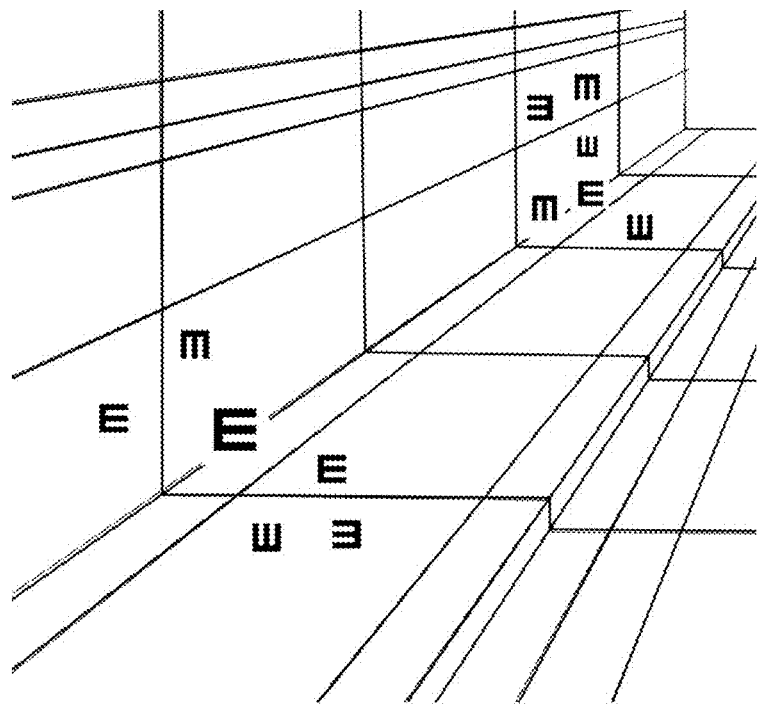

Embodiment 2: The present disclosure provides a heterogeneous visual acuity chart. Referring to FIG. 2, the heterogeneous visual acuity chart includes two types of optotypes of different sizes, a perspective that affects a visual depth of the optotypes of different sizes and two E-type optotype patterns composed of lines. A first type of optotypes include five small-sized optotypes, and a second type of optotypes include five large-sized optotypes. The first type of optotypes and the second type of optotypes are provided in different positions. The structure of the perspective is the same as that in Embodiment 1. Among the two E-type optotype patterns, the size of one E-type optotype pattern is not more than 0.5 times that of the first type of optotype, and the size of the other E-type optotype pattern is not less than 1.5 times that of the second type of optotype. Specifically, the first type of optotypes are provided in an upper right zone of the heterogeneous visual acuity chart. Among the five optotypes of the first type, optotypes 1 and 2 are provided in the same grid pattern. An optotype 3 is provided in a grid pattern 3 on a lower right side of the grid pattern where the optotypes 1 and 2 are located. Optotypes 4 and 5 are provided between a grid pattern on a lower side of the grid pattern where the optotypes 1 and 2 are located and a grid pattern on a left side of the grid pattern where the optotype 3 is located. A small-sized E-type optotype pattern is provided in a grid pattern on a lower side of the grid pattern where the optotypes 1 and 2 are located. A blank distance between each of the optotypes and an edge of the grid pattern where the optotype is located is not less than half of a width of one optotype of the first type. A blank distance between two adjacent optotypes in the same grid pattern is not less than half of the width of one optotype of the first type. There are four optotype directions. The directions of the two optotypes in the same grid pattern are different, and the directions of any two adjacent optotypes are also different. The second type of optotypes are provided in a lower left zone of the heterogeneous visual acuity chart. Among the five optotypes of the second type, optotypes 1 and 2 are provided in the same grid pattern. An optotype 3 is provided in a grid pattern 1 on an upper right side of the grid pattern where the optotypes 1 and 2 are located. An optotype 4 is provided in a grid pattern 1 on an upper left side of a grid pattern on a left side of the grid pattern where the optotype 3 is located. An optotype 5 is provided in a grid pattern on a lower left side of the grid pattern where the optotype 4 is located. A large-sized E-type optotype pattern is provided between a grid pattern on a left side of the grid pattern where the optotype 3 is located and the grid pattern where the optotype 4 is located. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the two optotypes in the same grid pattern are different, and the directions of any two adjacent optotypes are also different.

Figure 3:
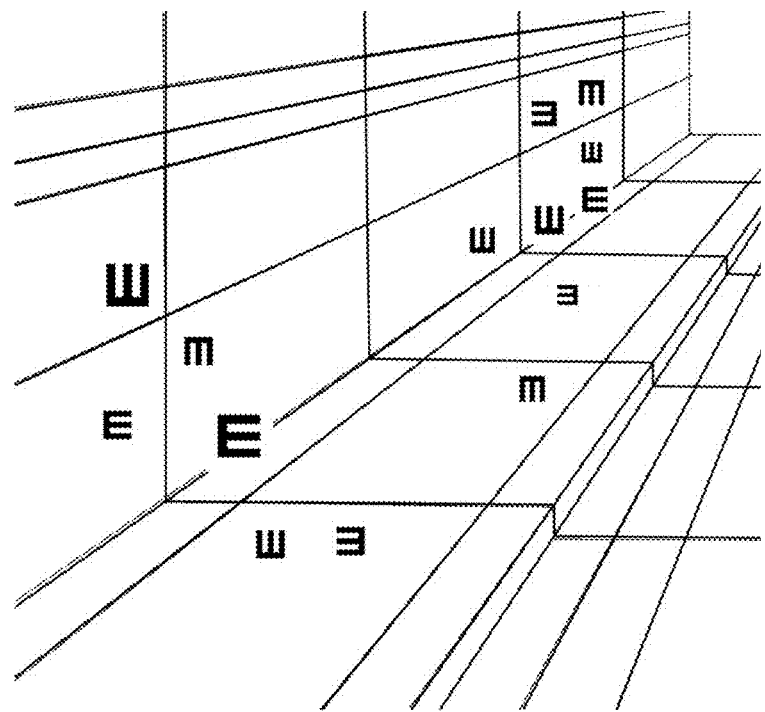

Embodiment 3: The present disclosure provides a heterogeneous visual acuity chart. Referring to FIG. 3, the heterogeneous visual acuity chart includes two types of optotypes of different sizes, a perspective that affects a visual depth of the optotypes of different sizes and four E-type optotype patterns composed of lines. A first type of optotypes include five small-sized optotypes, and a second type of optotypes include five large-sized optotypes. The two types of optotypes are divided into two sets. A first set of optotypes include four optotypes of the first type and one optotype of the second type, and the second set of optotypes include one optotype of the second type and four optotypes of the first type. The optotypes in the first set and the optotypes in the second set are provided in different positions. The four E-type optotype patterns include two small-sized E-type optotype patterns of the same size and two large-sized E-type optotype patterns of the same size. The size of the small-sized E-type optotype pattern is not more than 0.5 times that of the first type of optotype, and the size of the large-sized E-type optotype pattern is not less than 1.5 times that of the second type of optotype. The structure of the perspective is the same as that in Embodiment 1. Specifically, the first set of optotypes are provided in an upper right zone of the heterogeneous visual acuity chart. Among the five optotypes in the first set, optotypes 1, 2, 3 and 4 are the first type of optotypes, and optotype 5 is the second type of optotype. The optotypes 1 and 2 are provided in the same grid pattern. A first small-sized E-type optotype patterns is provided in a grid pattern on a lower side of the grid pattern where the optotypes 1 and 2 are located. The optotype 3 is provided in a grid pattern 1 on a left side of the grid pattern where the first small-sized E-type optotype pattern is located. A second small-sized E-type optotype pattern is provided in a grid pattern 2 on a lower right side of the grid pattern where the optotype 3 is located. Optotypes 4 and 5 are provided between the grid pattern where the first small-sized E-type optotype pattern is located and a grid pattern on a left side of a grid pattern 1 on an upper right side of the grid pattern where the second small-sized E-type optotype pattern is located. The optotype 5 is located on a lower left side of the optotype 4. A blank distance between the first type of optotype and an edge of the grid pattern where the first type of optotype is located is not less than half of a width of one optotype of the first type. A blank distance between two adjacent optotypes of the first type is not less than half of the width one optotype of the first type. A blank distance between the second type of optotype and an edge of the grid pattern where the second type of optotype is located is not less than half of a width of one optotype of the second type. A blank distance between optotypes of the first type and the second type that are adjacent is not less than half of the width of one optotype of the second type. There are four optotype directions. The directions of the two optotypes in the same grid pattern are different, and the directions of any two adjacent optotypes are also different. The second set of optotypes are provided in lower left zone of the heterogeneous visual acuity chart. Among the five optotypes in the second set, optotypes 1, 2, 3 and 4 are the second type of optotypes, and optotype 5 is the first type of optotype. The optotypes 1 and 2 are provided in the same grid pattern. The optotype 5 is provided in a grid pattern 1 on an upper right side of the grid pattern where the optotypes 1 and 2 are located. The optotype 3 is provided in a grid pattern 1 on an upper left side of a grid pattern on a left side of the grid pattern where the optotypes 1 and 2 are located. The optotype 4 is provided in a grid pattern 1 on a right side of the grid pattern where the optotype 3 is located. A first large-sized E-type optotype pattern is provided in a grid pattern 1 on an upper side of the grid pattern where the optotype 3 is located. A second large-sized E-type optotype pattern is provided between the grid pattern where the optotype 4 is located and a grid pattern on a left side of the grid pattern where the optotype 5 is located. A blank distance between each of the optotypes and an edge of the grid pattern where the optotype is located is not less than half of a width of one optotype of the second type. A blank distance between two adjacent optotypes is not less than half of the width of one optotype of the second type. There are four optotype directions. The directions of the two optotypes in the same grid pattern are different, and the directions of any two adjacent optotypes are also different.

Figure 4:
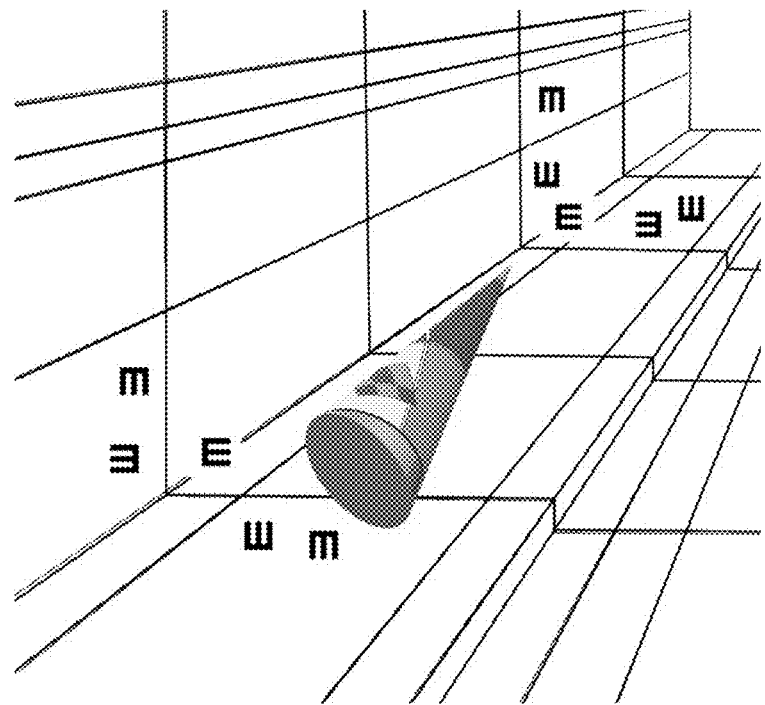

Embodiment 4: The present disclosure provides a heterogeneous visual acuity chart. Referring to FIG. 4, the heterogeneous visual acuity chart includes two types of optotypes of different sizes, a perspective that affects a visual depth of the optotypes of different sizes and a cone composed of lines. The cone is colored. A first type of optotypes include five small-sized optotypes, and a second type of optotypes include five large-sized optotypes. The first type of optotypes and the second type of optotypes are provided in different positions. The structure of the perspective is the same as that in Embodiment 1. Specifically, the first type of optotypes are provided in an upper right zone of the heterogeneous visual acuity chart. Among the five optotypes of the first type, optotypes 1 and 2 are provided in the same grid pattern. An optotype 3 is provided in a grid pattern 1 on an upper left side of a grid pattern on a left side of the grid pattern where the optotypes 1 and 2 are located. An optotype 4 is provided in a grid pattern 1 on an upper side of the grid pattern where the optotype 3 is located. An optotype 5 is provided among the grid pattern where the optotypes 1 and 2 are located, the grid pattern where the optotype 3 is located and a grid pattern on a left side of the grid pattern where the optotypes 1 and 2 located. A blank distance between each of the optotypes and an edge of the grid pattern where the optotype is located is not less than half of a width of one optotype of the first type. A blank distance between two adjacent optotypes in the same grid pattern is not less than half of the width of one optotype of the first type. There are four optotype directions. The directions of the two optotypes in the same grid pattern are different, and the directions of any two adjacent optotypes are also different. The second type of optotypes are provided in a lower left zone of the heterogeneous visual acuity chart. Among the five optotypes of the second type, optotypes 1 and 2 are provided in the same grid pattern. Optotypes 3 and 4 are provided in a grid pattern 1 on an upper left side of a grid pattern on a left side of the grid pattern where the optotypes 1 and 2 are located. An optotype 5 is provided between a grid pattern 1 on a right side of the grid pattern where the optotypes 3 and 4 are located and a grid pattern on a left side of a grid pattern 1 on an upper right side of the grid pattern where the optotypes 1 and 2 are located. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the two optotypes in the same grid pattern are different, and the directions of any two adjacent optotypes are also different. The cone is provided between the two types of optotypes; and an apex of the cone is near the first type of optotypes, and a bottom surface of the cone is near the second type of optotypes.

Figure 5:
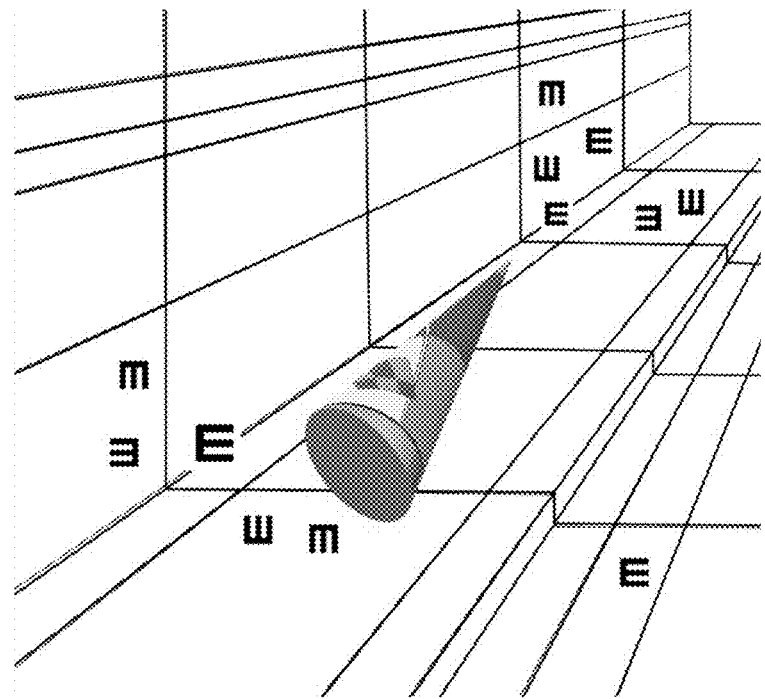

Embodiment 5: The present disclosure provides a heterogeneous visual acuity chart. Referring to FIG. 5, the heterogeneous visual acuity chart includes two types of optotypes of different sizes, a perspective that affects a visual depth of the optotypes of different sizes, two E-type optotype patterns composed of lines and a cone composed of lines. The cone is colored. A first type of optotype include five small-sized optotypes, and a second type of optotype include five large-sized optotypes. The first type of optotypes and the second type of optotypes are provided in different positions. Among the two E-type optotype patterns, the size of one E-type optotype pattern is not more than 0.5 times that of the first type of optotype, and the size of the other E-type optotype pattern is not less than 1.5 times that of the second type of optotype. The structure of the perspective is the same as that in Embodiment 1. Specifically, the first type of optotypes are provided in an upper right zone of the heterogeneous visual acuity chart. Among the five optotypes of the first type, optotypes 1 and 2 are provided in the same grid pattern. Optotypes 3 and 4 are provided in a grid pattern 1 on an upper left side of a grid pattern on a left side of the grid pattern where the optotypes 1 and 2 are located. An optotype 5 is provided in a grid pattern 1 on an upper side of the grid pattern where the optotypes 3 and 4 are located. A small-sized E-type optotype pattern is provided between the grid pattern where the optotypes 3 and 4 are located and a grid pattern on a left side of the grid pattern where the optotypes 1 and 2 are located. A blank distance between each of the optotypes and an edge of the grid pattern where the optotype is located is not less than half of a width of one optotype of the first type. A blank distance between two adjacent optotypes in the same grid pattern is not less than half of the width of one optotype of the first type. There are four optotype directions. The directions of the two optotypes in the same grid pattern are different, and the directions of any two adjacent optotypes are also different. The second type of optotypes are provided in a lower left zone of the heterogeneous visual acuity chart. Among the five optotypes of the second type, optotypes 1 and 2 are provided in the same grid pattern. Optotypes 3 and 4 are provided in a grid pattern 1 on an upper left side of a grid pattern on a left side of the grid pattern where the optotypes 1 and 2 are located. An optotype 5 is provided in a four grid pattern on a right side of the grid pattern where the optotypes 1 and 2 are located. A large-sized E-type optotype pattern is provided between a grid pattern 1 on an upper right side of the grid pattern where the optotypes 3 and 4 are located and a grid pattern 1 on an upper left side of the grid pattern where the optotypes 1 and 2 are located. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the two optotypes in the same grid pattern are different, and the directions of any two adjacent optotypes are also different. The cone is provided between the two types of optotypes; and an apex of the cone is near the first type of optotypes, and a bottom surface of the cone is near the second type of optotypes.

Figure 6:
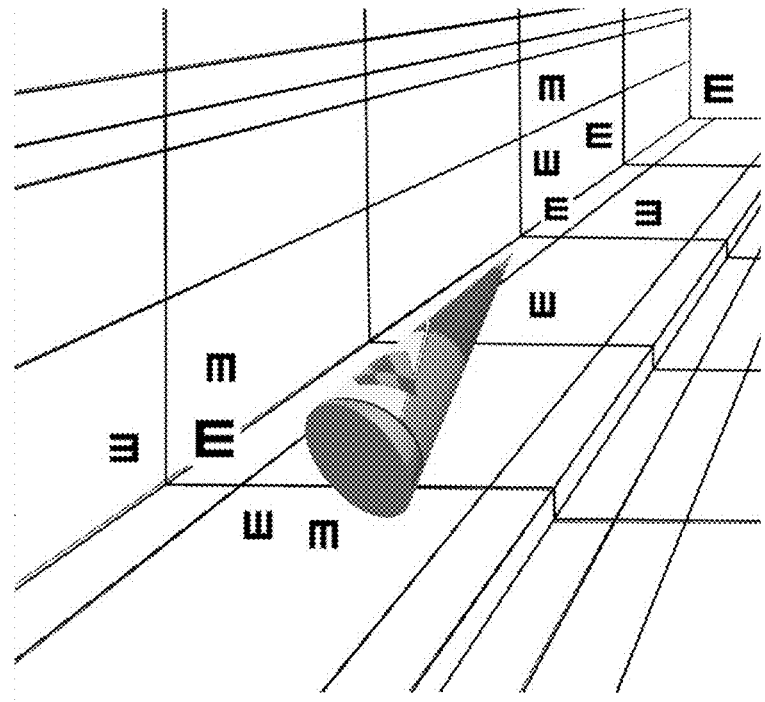

Embodiment 6: The present disclosure provides a heterogeneous visual acuity chart. Referring to FIG. 6, the heterogeneous visual acuity chart includes two types of optotypes of different sizes, a perspective that affects a visual depth of the optotypes of different sizes, two E-type optotype patterns composed of lines and a cone composed of lines. The cone is colored. A first type of optotypes include five small-sized optotypes, and a second type of optotypes include five large-sized optotypes. The two types of optotypes are divided into two sets. A first set of optotypes include five optotypes of the first type and one optotype of the second type, and the second set of optotypes include four optotypes of the second type. The optotypes in the first set and the optotypes in the second set are provided in different positions. Among the two E-type optotype patterns, the size of one E-type optotype pattern is not more than 0.5 times that of the first type of optotype, and the size of the other E-type optotype pattern is not less than 1.5 times that of the second type of optotype. The structure of the perspective is the same as that in Embodiment 1. Specifically, the first set of optotypes are provided in an upper right zone of the heterogeneous visual acuity chart. Among the 6 optotypes in the first set, optotypes 1, 2, 3, 4 and 5 are optotypes of the first type, and an optotype 6 is an optotype of the second type. The optotypes 1 and 2 are provided in the same grid pattern. The optotype 3 is provided in a grid pattern 1 on an upper side of the grid pattern where the optotypes 1 and 2 are located. The optotype 4 is provided in a grid pattern 1 on a right side of a grid pattern on a lower right side of the grid pattern where the optotypes 1 and 2 are located. The optotype 5 is provided in a grid pattern 1 on a lower left side of the grid pattern where the optotype 4 is located. The optotype 6 is provided in a blank zone on an upper right side of all smallest grid patterns. A first small-sized E-type optotype pattern is provided between the grid pattern where the optotypes 1 and 2 are located and a grid pattern on a left side of the grid pattern where the optotype 4 is located. A blank distance between the first type of optotype and an edge of the grid pattern where the optotype is located is not less than half of a width of one optotype of the first type. A blank distance between two optotypes of the first type is not less than half of the width of one optotype of the first type. A blank distance between the second type of optotype and an edge of the grid pattern where the optotype is located is not less than half of a width of one optotype of the second type. There are four optotype directions. The directions of the two optotypes in the same grid pattern are different, and the directions of any two adjacent optotypes are also different. The second set of optotypes are provided in a lower right zone of the heterogeneous visual acuity chart. Among the 4 optotypes of the second set, optotypes 1 and 2 are provided in the same grid pattern. An optotype 3 is provided in a grid pattern 1 on an upper left side of a grid pattern on a left side of the grid pattern where the optotypes 1 and 2 are located. An optotype 4 is provided in a grid pattern 1 on an upper right side of the grid pattern where the optotype 3 is located. A large-sized E-type optotype pattern is provided between the grid pattern where the optotype 4 is located and a grid pattern 1 on an upper left side of grid pattern where the optotypes 1 and 2 are located. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the two optotypes in the same grid pattern are different, and the directions of any two adjacent optotypes are also different. The cone is provided between the two sets of optotypes; and an apex of the cone is near the first set of optotypes, and a bottom surface of the cone is near the second set of optotypes.

Figure 7:
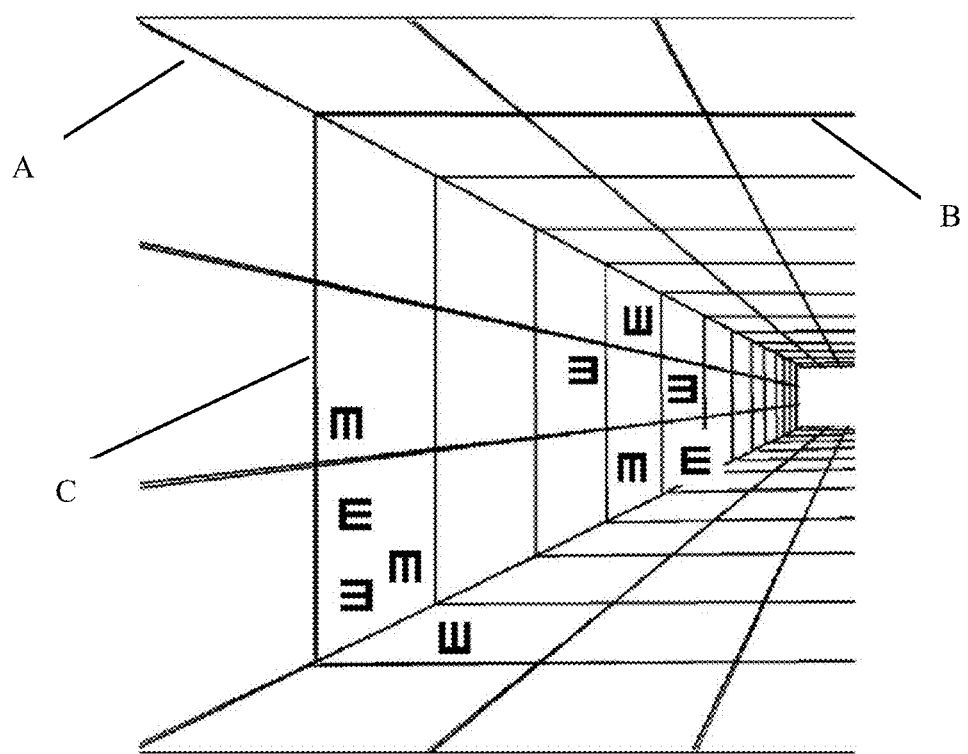

Embodiment 7: The present disclosure provides a heterogeneous visual acuity chart. Referring to FIG. 7, the heterogeneous visual acuity chart includes two types of optotypes of different sizes and a perspective that affects a visual depth of the optotypes of different sizes. A first type of optotypes include five small-sized optotypes, and a second type of optotypes include five large-sized optotypes. The first type of optotypes and the second type of optotypes are provided in different positions. The perspective includes first lines A, second lines B and third lines C. Multiple first lines A are concentrated at one point along a depth direction. Multiple parallel second lines B intersect with the first lines A in a horizontal direction to form grid patterns which define upper and lower horizontal planes. Multiple parallel third lines C intersect with the first lines A in a vertical direction to form multiple grid patterns, which are arranged in order from large to small to define a vertical plane. The second lines B in the upper and lower horizontal planes are respectively connected to the third lines C in the vertical plane at one point, such that the horizontal planes and the vertical plane are connected to define a three-dimensional space. Specifically, the first type of optotypes are provided in an upper right zone of the heterogeneous visual acuity chart. Among the five optotypes of the first type, an optotype 1 is provided in a grid pattern 1 on an upper side of a certain grid pattern. An optotype 2 is provided in a grid pattern 1 on a lower side of the certain grid pattern. An optotype 3 is provided in a grid pattern 1 on a left side of the certain grid pattern. An optotype 4 is provided in a grid pattern 1 on a right side of the certain grid pattern. An optotype 5 is provided among the four adjacent grid patterns. Among the four adjacent grid patterns, one grid pattern is adjacent to the grid pattern where the optotype 2 is located and the grid pattern where the optotype 4 is located. A blank distance between each of the optotypes and an edge of the grid pattern where the optotype is located is not less than half of a width of one optotype of the first type. There are four optotype directions. The directions of any two adjacent optotypes are different except that directions of the optotype 3 and the optotype 4 are the same. The second type of optotypes are provided in a lower left zone of the heterogeneous visual acuity chart. Among the five optotypes of the second type, optotypes 1, 2 and 3 are provided in the same grid pattern. An optotype 4 is provided in a grid pattern 1 on an upper side of the grid pattern where the optotypes 1, 2 and 3 are located. An optotype 5 is provided in a grid pattern 1 on a lower right side of the grid pattern where the optotypes 1, 2 and 3 are located. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the three optotypes in the same grid pattern are different, and the directions of any two adjacent optotypes are also different.

Figure 8:
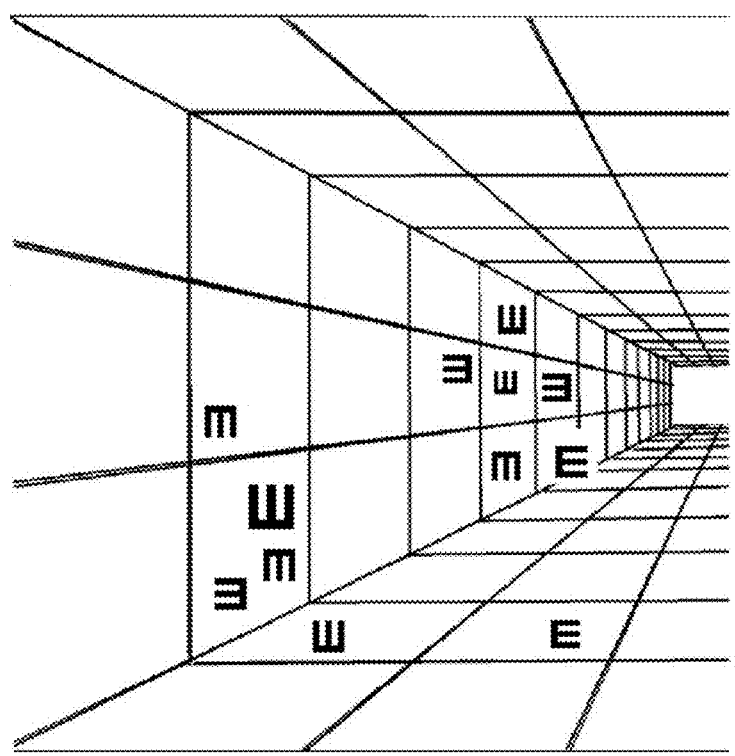

Embodiment 8: The present disclosure provides a heterogeneous visual acuity chart. Referring to FIG. 8, the heterogeneous visual acuity chart includes two types of optotypes of different sizes, a perspective that affects a visual depth of the optotypes of different sizes and two E-type optotype patterns composed of lines. A first type of optotypes include five small-sized optotypes, and a second type of optotypes include five large-sized optotypes. The two types of optotypes are divided into two sets. A first set of optotypes include four optotypes of the first type and one optotype of the second type, and the second set of optotypes include four optotypes of the second type and one optotype of the first type. The optotypes in the first set and the optotypes in the second set are provided in different positions. Among the two E-type optotype patterns, the size of one E-type optotype pattern is not more than 0.5 times that of the first type of optotype, and the size of the other E-type optotype pattern is not less than 1.5 times that of the second type of optotype. The structure of the perspective is the same as that in Embodiment 7. Specifically, the first set of optotypes are provided in an upper right zone of the heterogeneous visual acuity chart. Among the five optotypes of the first set, optotypes 1, 2, 3 and 4 are optotypes of the first type, and an optotype 5 is an optotype of the second type. A small-sized E-type optotype pattern is provided in a certain grid pattern. The optotype 1 is provided in a grid pattern 1 on an upper side of the certain grid pattern. The optotype 2 is provided in a grid pattern 1 on a lower side of the certain grid pattern. The optotype 3 is provided in a grid pattern 1 on a left side of the certain grid pattern. The optotype 4 is provided in a grid pattern 1 on a right side of the certain grid pattern. The optotype 5 is provided among the four adjacent grid patterns. Among the four adjacent grid patterns, one grid pattern is adjacent to the grid pattern where the small-sized E-type optotype pattern is located, the grid pattern where the optotype 2 is located and the grid pattern where the optotype 4 is located. A blank distance between the first type of optotype and an edge of the grid pattern where the optotype is located is not less than half of a width of one optotype of the first type. A blank distance between the second type of optotype and an edge of the grid pattern where the optotype is located is not less than half of a width of one optotype of the second type. There are four optotype directions. The directions of any two adjacent optotypes are different except that directions of the optotype 3 and the optotype 4 are the same. The second set of optotypes are provided in a lower left zone of the heterogeneous visual acuity chart. Among the five optotypes in the second set, optotypes 1, 2, 3 and 4 are optotypes of the second type, and an optotype 5 is an optotype of the first type. The optotypes 1 and 2 are provided in the same grid pattern. The optotype 3 is provided in a grid pattern 1 on an upper side of the grid pattern where the optotypes 1 and 2 are located. The optotype 4 is provided in a grid pattern 1 on a lower right side of the grid pattern where the optotypes 1 and 2 are located. The optotype 5 is provided in a grid pattern 1 on a right side of the grid pattern where the optotype 4 is located. A large-sized E-type optotype pattern is provided in the grid pattern where the optotypes 1 and 2 are located. A blank distance between the first type of optotype and an edge of the grid pattern where the optotype is located is not less than half of a width of one optotype of the first type. A blank distance between the second type of optotype and an edge of the grid pattern where the optotype is located is not less than half of the width of one optotype of the second type. A blank distance between two adjacent optotypes of the second type is not less than half of a width of one optotype of the second type. There are four optotype directions. The directions of the two optotypes in the same grid pattern are different, and the directions of any two adjacent optotypes are also different.

Figure 9:
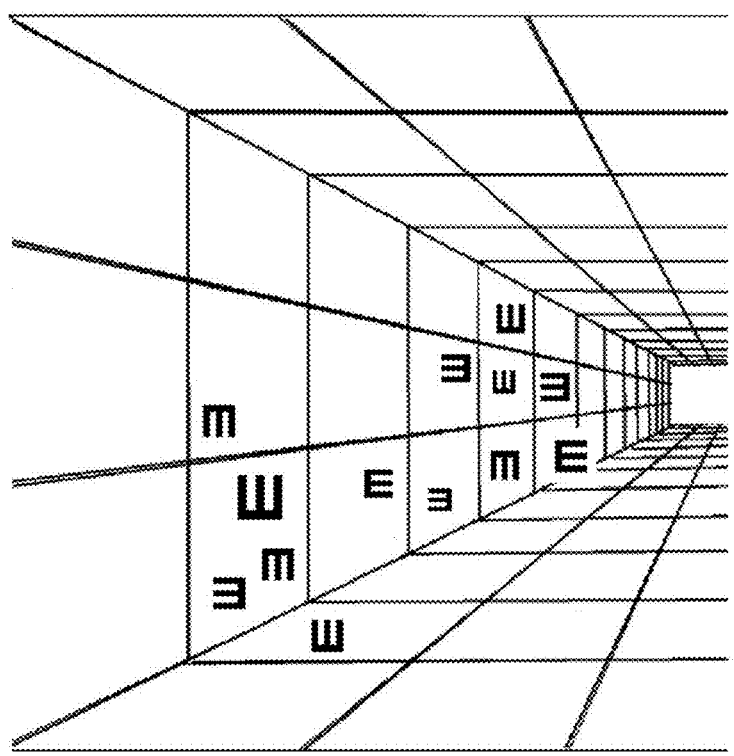

Embodiment 9: The present disclosure provides a heterogeneous visual acuity chart. Referring to FIG. 9, the heterogeneous visual acuity chart includes two types of optotypes of different sizes, a perspective that affects a visual depth of the optotypes of different sizes and three E-type optotype patterns composed of lines. A first type of optotypes include five small-sized optotypes, and a second type of optotypes include five large-sized optotypes. The two types of optotypes are divided into two sets. A first set of optotypes include four optotypes of the first type and one optotype of the second type, and the second set of optotypes include four optotypes of the second type and one optotype of the first type. The optotypes in the first set and the optotypes in the second set are provided in different positions. The three E-type optotype patterns include one large-sized E-type optotype pattern and two small-sized E-type optotype patterns of the same size. The size of the small-sized E-type optotype pattern is not more than 0.5 times that of the first type of optotype, and the size of the large-sized E-type optotype pattern is not less than 1.5 times that of the second type of optotype. The structure of the perspective is the same as that in Embodiment 7. Specifically, the first set of optotypes are provided in an upper right zone of the heterogeneous visual acuity chart. Among the five optotypes of the first set, optotypes 1, 2, 3 and 4 are optotypes of the first type, and an optotype 5 is an optotype of the second type. A first small-sized E-type optotype pattern is provided in a certain grid pattern. The optotype 1 is provided in a grid pattern 1 on an upper side of the certain grid pattern. The optotype 2 is provided in a grid pattern 1 on a lower side of the certain grid pattern. The optotype 3 is provided in a grid pattern 1 on a left side of the certain grid pattern. The optotype 4 is provided in a grid pattern 1 on a right side of the certain grid pattern. The optotype 5 is provided among the four adjacent grid patterns. Among the four adjacent grid patterns, one grid pattern is respectively adjacent to the grid pattern where the first small-sized E-type optotype pattern is located, the grid pattern where the optotype 2 is located and the grid pattern where the optotype 4 is located. A second small-sized E-type optotype pattern is provided in a grid pattern 1 on a lower left side of the grid pattern where the optotype 2 is located. A blank distance between the first type of optotype and an edge of the grid pattern where the optotype is located is not less than half of a width of one optotype of the first type. A blank distance between the second type of optotype and an edge of the grid pattern where the optotype is located is not less than half of a width of one optotype of the second type. There are four optotype directions. The directions of any two adjacent optotypes are different except that directions of the optotype 3 and the optotype 4 are the same. The second set of optotypes are provided in a lower left zone of the heterogeneous visual acuity chart. Among the five optotypes in the second set, optotypes 1, 2, 3 and 4 are optotypes of the second type, and an optotype 5 is an optotype of the first type. The optotypes 1 and 2 are provided in the same grid pattern. The optotype 3 is provided in a grid pattern 1 on an upper side of the grid pattern where the optotypes 1 and 2 are located. The optotype 4 is provided in a grid pattern 1 on a lower right side of the grid pattern where the optotypes 1 and 2 are located. The optotype 5 is provided in a grid pattern 1 on an upper right side of the grid pattern where the optotypes 1 and 2 are located. A large-sized E-type optotype pattern is provided in the grid pattern where the optotypes 1 and 2 are located. A blank distance between the first type of optotype and an edge of the grid pattern where the optotype is located is not less than half of a width of one optotype of the first type. A blank distance between the second type of optotype and an edge of the grid pattern where the optotype is located is not less than half of the width of one optotype of the second type. A blank distance between two adjacent optotypes of the second type is not less than half of a width of one optotype of the second type. There are four optotype directions. The directions of the two optotypes in the same grid pattern are different, and the directions of any two adjacent optotypes are also different.

Figure 10:
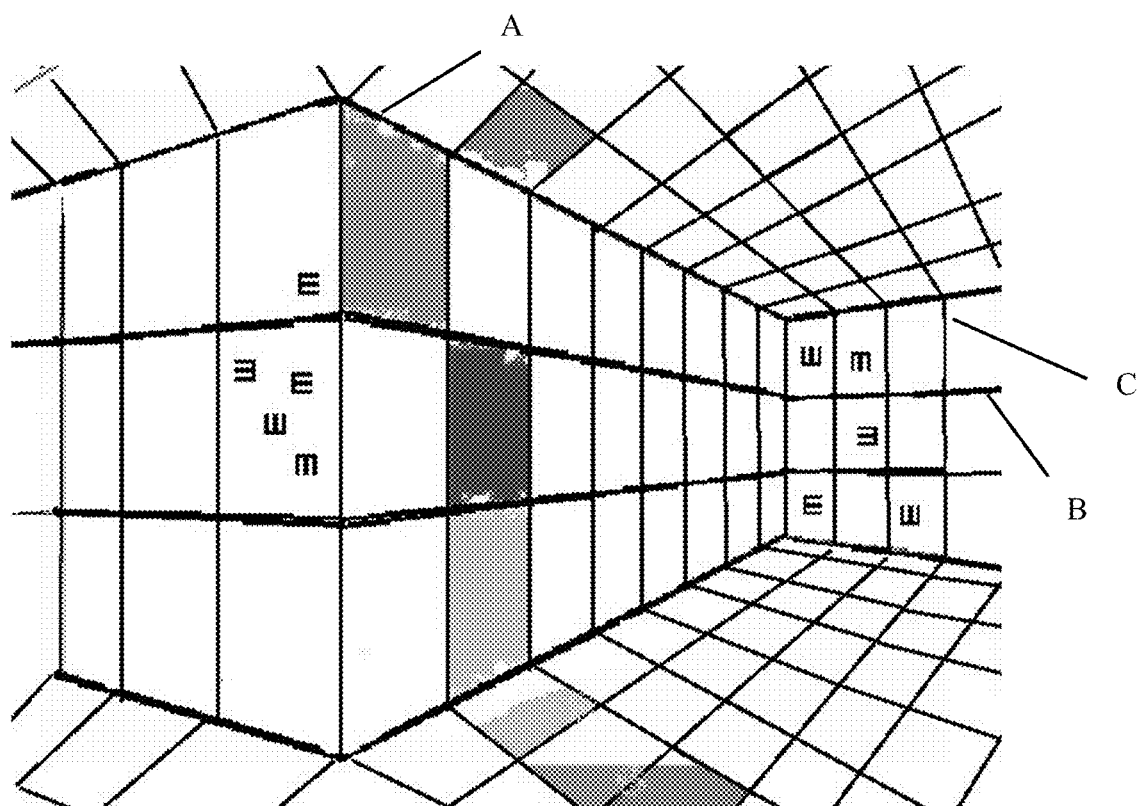

Embodiment 10: The present disclosure provides a heterogeneous visual acuity chart. Referring to FIG. 10, the heterogeneous visual acuity chart includes two types of optotypes of different sizes and a perspective that affects a visual depth of the optotypes of different sizes. A first type of optotypes include five small-sized optotypes, and a second type of optotypes include five large-sized optotypes. The first type of optotypes and the second type of optotypes are provided in different positions. The perspective includes first lines A, second lines B and third lines C. Multiple first lines A are concentrated at one point along a depth direction. Multiple parallel third lines C intersect with the first lines A in a vertical direction to form multiple grid patterns, which are arranged in order from large to small to define a vertical plane. The second lines B intersect with the third lines C to form grid patterns which define front and back planes. The second lines B in the front and back planes are respectively connected to the first lines A in the vertical plane at one point, such that the front and back planes and the vertical plane are connected. Grid patterns are supplemented on upper and lower sides of the vertical plane, the front plane and the back plane to finally define two spaces that are connected. Specifically, the first type of optotypes are provided in a right zone of the heterogeneous visual acuity chart. Among the five optotypes of the first type, an optotype 1 is provided in a certain grid pattern. An optotype 2 is provided in a grid pattern 1 on an upper side of the grid pattern where the optotype 1 is located. An optotype 3 is provided in a grid pattern 1 on a left side of the grid pattern where the optotype 2 is located. An optotype 4 is provided in a grid pattern 2 on a lower side of the grid pattern where the optotype 3 is located. An optotype 5 is provided in a grid pattern 2 on a right side of the grid pattern where the optotype 4 is located. A blank distance between each of the optotypes and an edge of the grid pattern where the optotype is located is not less than half of a width of one optotype of the first type. There are four optotype directions. The directions of any two adjacent optotypes are different. The second type of optotypes are provided in a left zone of the heterogeneous visual acuity chart. The five optotypes of the second type are distributed in two adjacent grid patterns. Among them, optotypes 1, 2, 3 and 4 are provided in the same grid pattern. An optotype 5 is provided in a grid pattern 1 on an upper side of the grid pattern where the optotypes 1, 2, 3 and 4 are located. A grid pattern 1 on a right side of the grid pattern where the optotype 5 is located is a colored grid pattern. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the four optotypes in the same grid pattern are different, and the directions of any two adjacent optotypes are also different.

Figure 11:
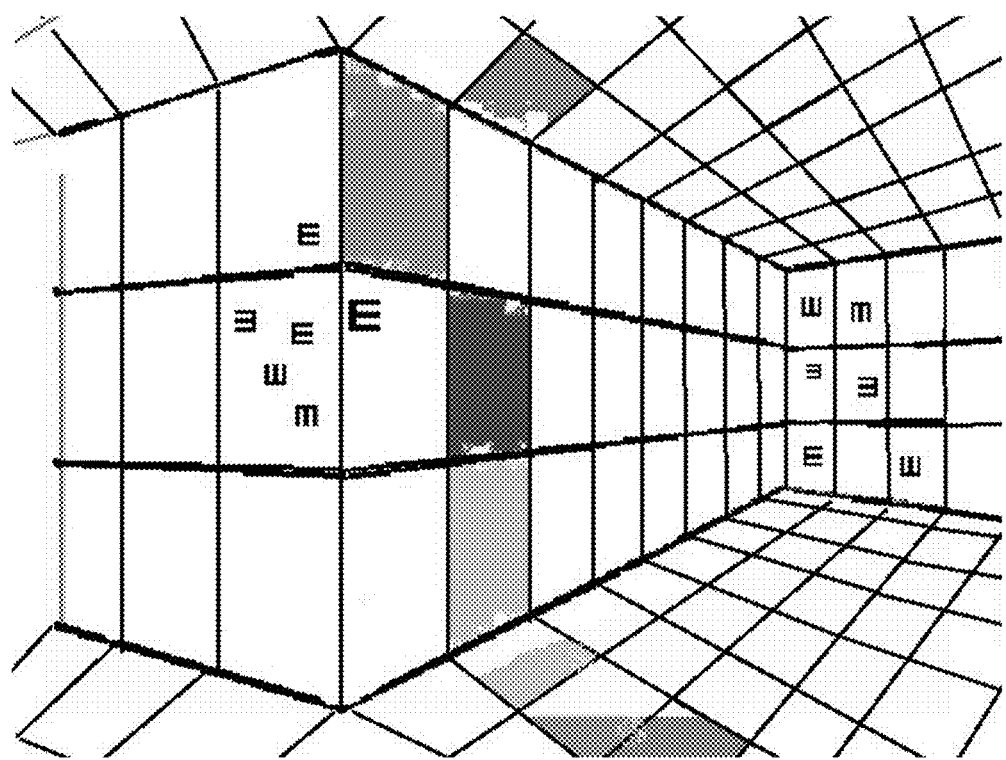

Embodiment 11: The present disclosure provides a heterogeneous visual acuity chart. Referring to FIG. 11, the heterogeneous visual acuity chart includes two types of optotypes of different sizes, a perspective that affects a visual depth of the optotypes of different sizes and two E-type optotype patterns composed of lines. A first type of optotypes include five small-sized optotypes, and a second type of optotypes include five large-sized optotypes. The first type of optotypes and the second type of optotypes are provided in different positions. Among the two E-type optotype patterns, the size of one E-type optotype pattern is not more than 0.5 times that of the first type of optotype, and the size of the other E-type optotype pattern is not less than 1.5 times that of the second type of optotype. The structure of the perspective is the same as that in Embodiment 10. Specifically, the first type of optotypes are provided in a right zone of the heterogeneous visual acuity chart. Among the five optotypes of the first type, an optotype 1 is provided in a certain grid pattern, and an optotype 2 is provided in a grid pattern 1 on an upper side of the grid pattern where the optotype 1 is located. An optotype 3 is provided in a grid pattern 1 on a left side of the grid pattern where the optotype 2 is located. An optotype 4 is provided in a grid pattern 2 on a lower side of the grid pattern where the optotype 3 is located. An optotype 5 is provided in a grid pattern 2 on a right side of the grid pattern where the optotype 4 is located. A small-sized E-type optotype pattern is provided in a grid pattern 1 on a lower side of the grid pattern where the optotype 3 is located. A blank distance between each of the optotypes and an edge of the grid pattern where the optotype is located is not less than half of a width of one optotype of the first type. There are four optotype directions. The directions of any two adjacent optotypes are different. The second type of optotypes are provided in a left zone of the heterogeneous visual acuity chart. The five optotypes of the second type are distributed in two adjacent grid patterns. Among them, optotypes 1, 2, 3 and 4 are provided in the same grid pattern, and an optotype 5 is provided in a grid pattern 1 on an upper side of the grid pattern where the optotypes 1, 2, 3 and 4 are located. A large-sized E-type optotype pattern is provided in a grid pattern 1 on a right side of the grid pattern where the optotypes 1, 2, 3 and 4 are located. A grid pattern 1 on a right side of the grid pattern where the optotype 5 is located is a colored grid pattern, and a grid pattern 1 on a right side of the large-sized E-type optotype pattern is a colored grid pattern. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the four optotypes in the same grid pattern are different, and the directions of any two adjacent optotypes are also different.

Figure 12:
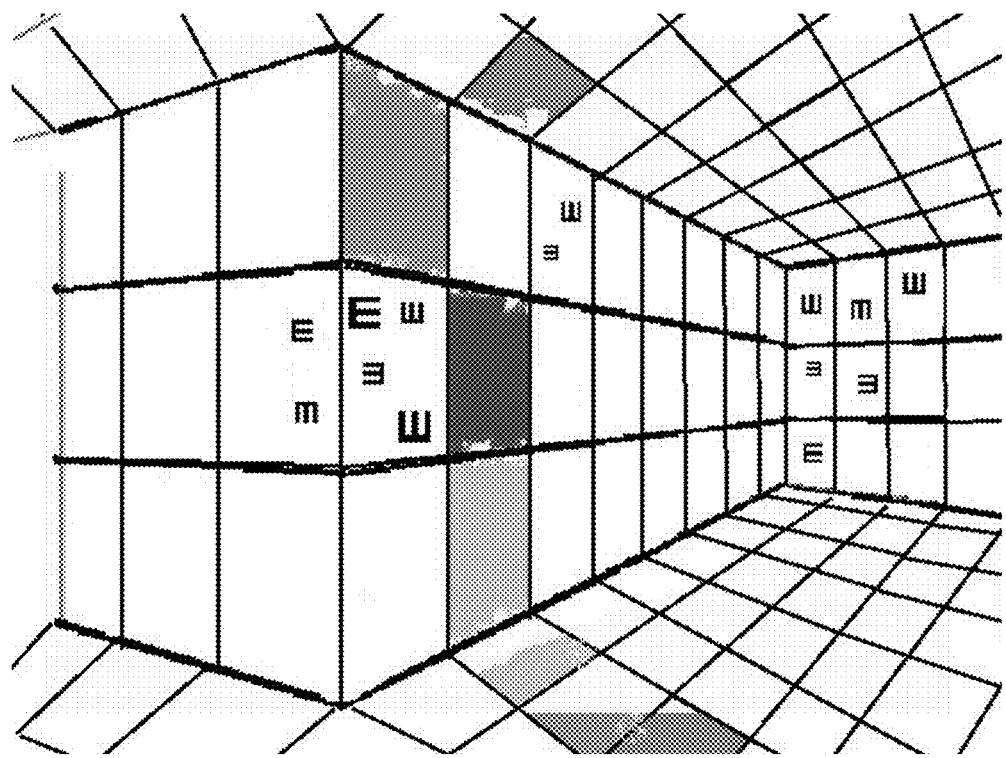

Embodiment 12: The present disclosure provides a heterogeneous visual acuity chart. Referring to FIG. 12, the heterogeneous visual acuity chart includes two types of optotypes of different sizes, a perspective that affects a visual depth of the optotypes of different sizes and four E-type optotype patterns composed of lines. A first type of optotypes include five small-sized optotypes, and a second type of optotypes include five large-sized optotypes. The two types of optotypes are divided into two sets. A first set of optotypes include four optotypes of the first type and one optotype of the second type, and the second set of optotypes include four optotypes of the second type and one optotype of the first type. The optotypes in the first set and the optotypes in the second set are provided in different positions. The four E-type optotype patterns include two small-sized E-type optotype patterns of the same size and two large-sized E-type optotype patterns of the same size. The size of the small-sized E-type optotype pattern is not more than 0.5 times that of the first type of optotype, and the size of the large-sized E-type optotype pattern is not less than 1.5 times that of the second type of optotype. The structure of the perspective is the same as that in Embodiment 10. Specifically, the first set of optotypes are provided in a right zone of the heterogeneous visual acuity chart. Among the five optotypes of the first set, optotypes 1, 2, 3 and 4 are optotypes of the first type, and an optotype 5 is an optotype of the second type. The optotype 1 is provided in a certain grid pattern. The optotype 2 is provided in a grid pattern 1 on an upper side of the grid pattern where the optotype 1 is located. The optotype 3 is provided in a grid pattern 1 on a left side of the grid pattern where the optotype 2 is located. The optotype 4 is provided in a grid pattern 2 on a lower side of the grid pattern where the optotype 3 is located. The optotype a first 5 is provided in a grid pattern 1 on a right side of the grid pattern where the optotype 2 is located. A small-sized E-type optotype pattern is provided in a grid pattern 1 on a lower side of the grid pattern where the optotype 3 is located. A blank distance between each of the optotypes of the first type and an edge of the grid pattern where the optotype is located is not less than half of a width of one optotype of the first type. A blank distance between the optotype of the second type and an edge of the grid pattern where the optotype is located is not less than half of a width of one optotype of the second type. There are four optotype directions. The directions of any two adjacent optotypes are different. The second set of optotypes are provided in a left zone of the heterogeneous visual acuity chart. Among the five optotypes in the second set, optotypes 1, 2, 3 and 4 are optotypes of the second type, and an optotype 5 is an optotype of the first type. The optotypes 1 and 2 are provided in the same grid pattern. The optotypes 3 and 4 are provided in a grid pattern 1 on a right side of the grid pattern where the optotypes 1 and 2 are located. The optotype 5 is provided in a grid pattern 1 on an upper side of a grid pattern 2 on a right side of the grid pattern where the optotypes 3 and 4 are located. First and second large-sized E-type optotype patterns are provided in the grid pattern where the optotypes 3 and 4 are located. A second small-sized E-type optotype pattern is provided in the grid pattern where the optotype 5 is located. The grid patterns 1 on the upper side and the right side of the grid pattern where the optotypes 3 and 4 are located are colored grid patterns. A blank distance between the optotype of the first type and an edge of the grid pattern where the optotype is located is not less than half of a width of one optotype of the first type. A blank distance between each of the optotypes of the second type and an edge of the grid pattern where the optotype is located is not less than half of the width of one optotype of the second type. A blank distance between two adjacent optotypes of the second type is not less than half of a width of one optotype of the second type. There are four optotype directions. The directions of the two optotypes in the same grid pattern are different, and the directions of any two adjacent optotypes are also different.

Figure 13:
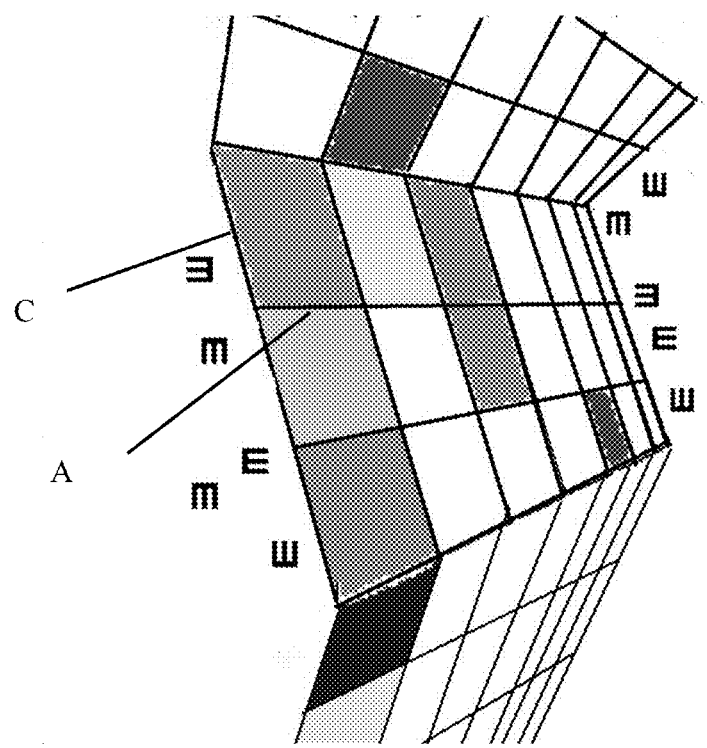

Embodiment 13: The present disclosure provides a heterogeneous visual acuity chart. Referring to FIG. 13, the heterogeneous visual acuity chart includes two types of optotypes of different sizes and a perspective that affects a visual depth of the optotypes of different sizes. A first type of optotypes include five small-sized optotypes, and a second type of optotypes include five large-sized optotypes. The first type of optotypes and the second type of optotypes are provided in different positions. The perspective includes first lines A and third lines C. Multiple first lines A are concentrated at one point along a depth direction. Multiple parallel third lines C intersect with the first lines A in a vertical direction to form multiple grid patterns, which are arranged in order from large to small to define a vertical plane. The vertical plane is inclined at a suitable angle. Specifically, the vertical plane is inclined inward (relative to the paper) around a lower side. Grid patterns are supplemented inward and outward respectively on the upper and lower sides of the vertical plane to form two spaces that are connected. Specifically, the first type of optotypes are provided in a right blank zone of the heterogeneous visual acuity chart. The five optotypes of the first type are arranged in order from top to bottom, which are optotypes 1, 2, 3, 4 and 5 in sequence. The vertical center lines of the five optotypes are different. A blank distance between each of the optotypes and an edge of an adjacent grid pattern is not less than half of a width of one optotype of the first type. A blank distance between two adjacent optotypes is not less than half of the width of one optotype of the first type. There are four optotype directions. The directions of any two adjacent optotypes are different except that the directions of the optotypes 1 and 5 are the same. The second type of optotypes are provided in a left blank zone of the heterogeneous visual acuity chart. The five optotypes of the second type are arranged in order from top to bottom, which are optotypes 1, 2, 3, 4 and 5 in sequence. The vertical center lines of the five optotypes are different. Grid patterns adjacent to the optotypes are all colored grid patterns. A blank distance between each of the optotypes and an edge of the adjacent grid pattern is not less than half of a width of one optotype of the second type. A blank distance between two adjacent optotypes is not less than half of the width of one optotype of the second type. There are four optotype directions. The directions of any two adjacent optotypes are different except that the directions of the optotypes 2 and 4 are the same.

Figure 14:
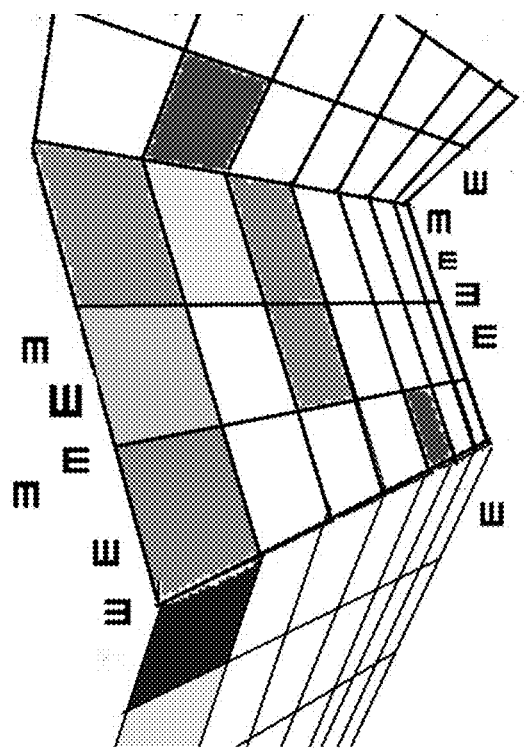

Embodiment 14: The present disclosure provides a heterogeneous visual acuity chart. Referring to FIG. 14, the heterogeneous visual acuity chart includes two types of optotypes of different sizes, a perspective that affects a visual depth of the optotypes of different sizes and two E-type optotype patterns composed of lines. A first type of optotypes include five small-sized optotypes, and a second type of optotypes include five large-sized optotypes. The first type of optotypes and the second type of optotypes are provided in different positions. Among the two E-type optotype patterns, the size of one E-type optotype pattern is not more than 0.5 times that of the first type of optotype, and the size of the other E-type optotype pattern is not less than 1.5 times that of the second type of optotype. The structure of the perspective is the same as that in Embodiment 13. Specifically, the first type of optotypes are provided in a right blank zone of the heterogeneous visual acuity chart. The five optotypes of the first type are arranged in order from top to bottom, which are optotypes 1, 2, 3, 4 and 5 in sequence. The vertical center lines of the five optotypes are different. A small-sized E-type optotype pattern is located between the optotypes 2 and 3. A blank distance between each of the optotypes and an edge of an adjacent grid pattern is not less than half of a width of one optotype of the first type. A blank distance between two adjacent optotypes is not less than half of the width of one optotype of the first type. A blank distance between each of the optotypes 2 and 3 and an edge of the adjacent E-type optotype pattern is not less than half of the width of one optotype of the first type. There are four optotype directions. The directions of any two adjacent optotypes are different except that the directions of the optotypes 1 and 5 are the same. The second type of optotypes are provided in a left blank zone of the heterogeneous visual acuity chart. The five optotypes of the second type are arranged in order from top to bottom, which are optotypes 1, 2, 3, 4 and 5 in sequence. The vertical center lines of the five optotypes are different. A large-sized E-type optotype pattern is located between the optotypes 1 and 2. Grid patterns adjacent to the optotypes are all colored grid patterns. A blank distance between each of the optotypes and an edge of the adjacent grid pattern is not less than half of a width of one optotype of the second type. A blank distance between two adjacent optotypes is not less than half of the width of one optotype of the second type. A blank distance between each of the optotypes and an edge of the adjacent E-type optotype pattern is not less than half of the width of one optotype of the second type. There are four optotype directions. The directions of any two adjacent optotypes are different except that the directions of the optotypes 1 and 3 are the same.

Figure 15:
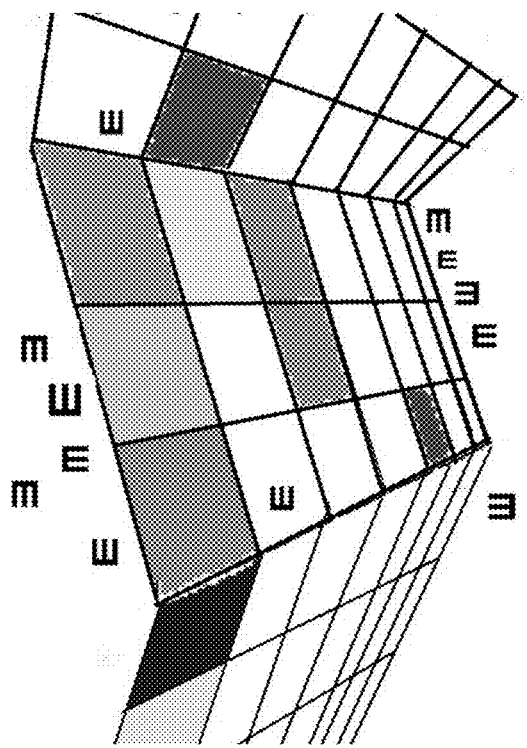

Embodiment 15: The present disclosure provides a heterogeneous visual acuity chart. Referring to FIG. 15, the heterogeneous visual acuity chart includes two types of optotypes of different sizes, a perspective that affects a visual depth of the optotypes of different sizes and two E-type optotype patterns composed of lines. A first type of optotypes include five small-sized optotypes, and a second type of optotypes include five large-sized optotypes. The two types of optotypes are divided into two sets. A first set of optotypes include three optotypes of the first type and one optotype of the second type, and the second set of optotypes include four optotypes of the second type and two optotypes of the first type. The optotypes in the first set and the optotypes in the second set are provided in different positions. Among the two E-type optotype patterns, the size of one E-type optotype pattern is not more than 0.5 times that of the first type of optotype, and the size of the other E-type optotype pattern is not less than 1.5 times that of the second type of optotype. The structure of the perspective is the same as that in Embodiment 13. Specifically, the first set of optotypes are provided in a right blank zone of the heterogeneous visual acuity chart. The four optotypes of the first set are arranged in order from top to bottom, which are optotypes 1, 2, 3 and 4 in sequence. The vertical center lines of the four optotypes are different. The optotypes 1, 2 and 3 are optotypes of the first type, and the optotype 4 is an optotype of the second type. A small-sized E-type optotype pattern is located between the optotypes 1 and 2. A blank distance between each of the optotypes of the first type and an edge of an adjacent grid pattern is not less than half of a width of one optotype of the first type. A blank distance between two adjacent optotypes of the first type is not less than half of the width of one optotype of the first type. A blank distance between each of the optotypes 1 and 2 and an edge of the adjacent E-type optotype pattern is not less than half of the width of one optotype of the first type. A blank distance between optotypes of the first type and the second type that are adjacent is not less than the width of one optotype of the second type. There are four optotype directions. The directions of any two adjacent optotypes are different. The second set of optotypes are provided in a left zone of the heterogeneous visual acuity chart. Among the 6 optotypes, optotypes 1, 2, 3 and 4 are optotypes of the second type, and optotypes 5 and 6 are optotypes of the first type. The optotypes 1, 2, 3 and 4 are provided in a left blank zone of the heterogeneous visual acuity chart, and are arranged in order from top to bottom. The vertical center lines of the four optotypes are different. The optotype 5 is provided in a grid pattern 2 on an upper side of a grid pattern 1 on a right side of the optotype 1. The optotype 6 is provided in a grid pattern 2 on a right side of the optotype 4. Grid patterns 1 to 5 on a lower side of the optotype 5 are all colored grid patterns. A blank distance between each of the optotypes of the first type and an edge of the adjacent grid pattern is not less than half of a width of one optotype of the first type. A blank distance between each of the optotypes of the second type and an edge of the adjacent grid pattern is not less than half of a width of one optotype of the second type. A blank distance between two adjacent optotypes of the second type is not less than half of the width of one optotype of the second type. There are four optotype directions. The directions of any two adjacent optotypes are different except that the directions of the optotypes 1 and 3 are the same.

Figure 16:
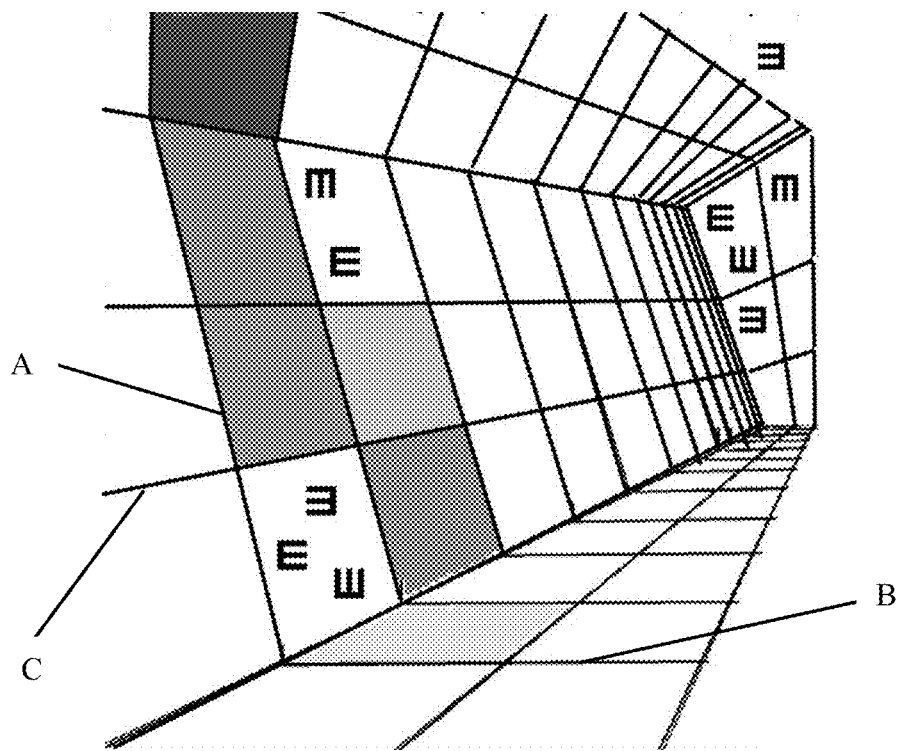

Embodiment 16: The present disclosure provides a heterogeneous visual acuity chart. Referring to FIG. 16, the heterogeneous visual acuity chart includes two types of optotypes of different sizes and a perspective that affects a visual depth of the optotypes of different sizes. A first type of optotypes include five small-sized optotypes, and a second type of optotypes include five large-sized optotypes. The first type of optotypes and the second type of optotypes are provided in different positions. The perspective includes first lines A, second lines B and third lines C. Multiple first lines A are concentrated at one point along a depth direction. Multiple parallel second lines B intersect with the first lines A in a horizontal direction to form grid patterns which define a horizontal plane. Multiple parallel third lines C intersect with the first lines A in a vertical direction to form multiple grid patterns, which are arranged in order from large to small to define a vertical plane. The second lines B in the horizontal plane are respectively connected to the third lines C in the vertical plane at one point, such that the horizontal plane and the vertical plane are connected to define a three-dimensional space. The vertical plane is inclined at a suitable angle. Specifically, the vertical plane is inclined inward (relative to the paper) around a line of intersection between the vertical plane and the horizontal plane. Grid patterns are supplemented on an upper side of the vertical plane to define a three-dimensional space. Specifically, the first type of optotypes are provided in a right zone of the heterogeneous visual acuity chart. Among the five optotypes in the first type, optotypes 1 and 2 are provided in the same grid pattern. An optotype 3 is provided in a grid pattern 1 on a lower side of the grid pattern where the optotypes 1 and 2 are located. An optotype 4 is provided in a grid pattern 1 on a right side of the grid pattern where the optotypes 1 and 2 are located. A blank zone is provided on a right side of the grid pattern where the optotype 4 is located. An optotype 5 is provided in a blank zone on an upper side of the grid pattern where the optotype 4 is located. A blank distance between each of the optotypes and an edge of the grid pattern where the optotype is located or a grid pattern to which the optotype is adjacent is not less than half of a width of one optotype of the first type. There are four optotype directions. The directions of the two optotypes in the same grid pattern are different, and the directions of any two adjacent optotypes are also different. The second type of optotypes are provided in a left zone of the heterogeneous visual acuity chart. Among the five optotypes of the second type, optotypes 1, 2 and 3 are provided in the same grid pattern. Optotypes 4 and 5 are provided in a grid pattern 1 on a right side of a grid pattern 2 on an upper side of the grid pattern where the optotypes 1, 2 and 3 are located. Grid patterns 1 to 3 on the upper side of the grid pattern where the optotypes 1, 2 and 3 are located, grid pattern 1 on a lower side of the grid pattern where the optotypes 1, 2 and 3 are located and grid patterns 1 and 2 on a lower side of the grid pattern where the optotypes 4 and 5 are located are all colored grid patterns. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the optotypes in the same grid pattern are different, and the directions of any two adjacent optotypes are also different.

Figure 17:
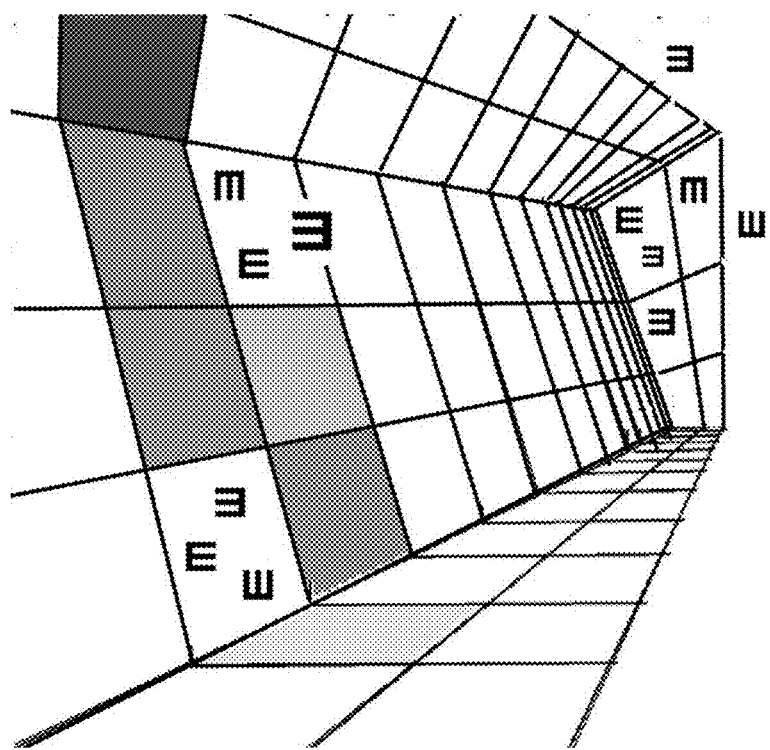

Embodiment 17: The present disclosure provides a heterogeneous visual acuity chart. Referring to FIG. 17, the heterogeneous visual acuity chart includes two types of optotypes of different sizes, a perspective that affects a visual depth of the optotypes of different sizes and two E-type optotype patterns composed of lines. A first type of optotypes include five small-sized optotypes, and a second type of optotypes include five large-sized optotypes. The first type of optotypes and the second type of optotypes are provided in different positions. Among the two E-type optotype patterns, the size of one E-type optotype pattern is not more than 0.5 times that of the first type of optotype, and the size of the other E-type optotype pattern is not less than 1.5 times that of the second type of optotype. The perspective is the same as that in Embodiment 16. Specifically, the first type of optotypes are provided in a right zone of the heterogeneous visual acuity chart. Among the five optotypes of the first type, an optotype 1 is provided in a certain grid pattern, and an optotype 2 is provided in a grid pattern 1 on a lower side of the grid pattern where the optotype 1 is located. An optotype 3 is provided in a grid pattern 1 on a right side of the grid pattern where the optotype 1 is located. A blank zone is provided on a right side of the grid pattern where the optotype 3 is located. An optotype 4 is provided in the blank zone on the right side of the grid pattern where the optotype 3 is located. An optotype 5 is provided in a blank zone on an upper side of the grid pattern where the optotype 3 is located. A small-sized E-type optotype pattern is provided in the grid pattern where the optotype 1 is located. A blank distance between each of the optotypes and an edge of the grid pattern where the optotype is located or a grid pattern to which the optotype is adjacent is not less than half of a width of one optotype of the first type. There are four optotype directions. The directions of any two adjacent optotypes are different. The second type of optotypes are provided in a left zone of the heterogeneous visual acuity chart. Among the five optotypes of the second type, optotypes 1, 2 and 3 are provided in the same grid pattern. Optotypes 4 and 5 are provided in a grid pattern 1 on a right side of a grid pattern 2 on an upper side of the grid pattern where the optotypes 1, 2 and 3 are located. A large-sized E-type optotype pattern is located between the grid pattern where the optotypes 4 and 5 are located and the grid pattern 1 on the right side of the grid pattern where the optotypes 4 and 5 are located. Grid patterns 1 to 3 on the upper side of the grid pattern where the optotypes 1, 2 and 3 are located, grid pattern 1 on a lower side of the grid pattern where the optotypes 1, 2 and 3 are located and grid patterns 1 and 2 on a lower side of the grid pattern where the optotypes 4 and 5 are located are all colored grid patterns. A blank distance between each of the optotypes and an edge of the grid pattern where the optotype is located is not less than half of a width of one optotype of the second type. A blank distance between two adjacent optotypes in the same grid pattern is not less than half of the width of one optotype of the second type. There are four optotype directions. The directions of the optotypes in the same grid pattern are different, and the directions of any two adjacent optotypes are also different.

Figure 18:
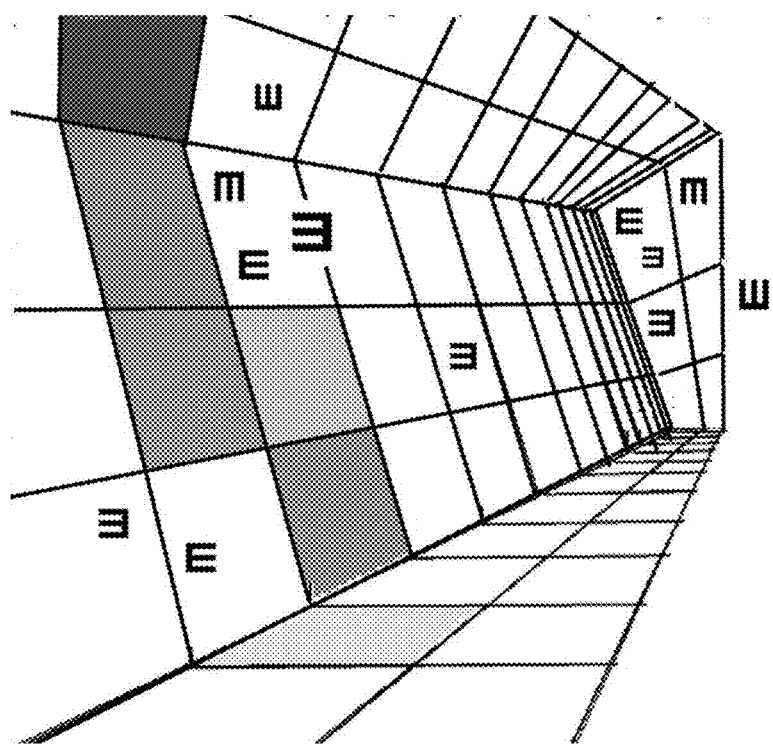

Embodiment 18: The present disclosure provides a heterogeneous visual acuity chart. Referring to FIG. 18, the heterogeneous visual acuity chart includes two types of optotypes of different sizes, a perspective that affects a visual depth of the optotypes of different sizes and two E-type optotype patterns composed of lines. A first type of optotypes include five small-sized optotypes, and a second type of optotypes include five large-sized optotypes. The two types of optotypes are divided into two sets. A first set of optotypes include three optotypes of the first type and one optotype of the second type, and the second set of optotypes include four optotypes of the second type and two optotypes of the first type. The optotypes in the first set and the optotypes in the second set are provided in different positions. Among the two E-type optotype patterns, the size of one E-type optotype pattern is not more than 0.5 times that of the first type of optotype, and the size of the other E-type optotype pattern is not less than 1.5 times that of the second type of optotype. The perspective is the same as that in Embodiment 16. Specifically, the first set of optotypes are provided in a right zone of the heterogeneous visual acuity chart. Among the 4 optotypes of the first set, optotypes 1, 2 and 3 are optotypes of the first type, and an optotype 4 is an optotype of the second type. The optotype 1 is provided in a certain grid pattern. The optotype 2 is provided in a grid pattern 1 on a lower side of the grid pattern where the optotype 1 is located. The optotype 3 is provided in a grid pattern 1 on a right side of the grid pattern where the optotype 1 is located. A blank zone is provided on a right side of the grid pattern where the optotype 3 is located. The optotype 4 is provided in a blank zone on a right side of a grid pattern 1 on a lower side of the grid pattern where the optotype 3 is located. A small-sized E-type optotype pattern is provided in the grid pattern where the optotype 1 is located. A blank distance between each of the optotypes of the first type and an edge of the grid pattern where the optotype is located or a grid pattern to which the optotype is adjacent is not less than half of a width of one optotype of the first type. A blank distance between the optotype of the second type and an edge of a grid pattern to which the optotype is adjacent is not less than half of a width of one optotype of the second type. There are four optotype directions. The directions of any two adjacent optotypes are different. The second set of optotypes are provided in a left zone of the heterogeneous visual acuity chart. Among the 6 optotypes in the second set, optotypes 1, 2, 3 and 4 are optotypes of the second type, and optotypes 5 and 6 are optotypes of the first type. The optotypes 1 and 2 are provided in the same grid pattern. The optotype 3 is provided in a grid pattern 2 on a lower side of a grid pattern 1 on a left side of the grid pattern where the optotypes 1 and 2 are located. The optotype 4 is provided in a grid pattern 1 on a left side of the grid pattern where the optotype 3 is located. The optotype 5 is provided in a grid pattern 1 on an upper side of the grid pattern where the optotypes 1 and 2 are located. The optotype 6 is provided in a grid pattern 2 on a right side of a grid pattern 1 on a lower side of the grid pattern where the optotypes 1 and 2 are located. A large-sized E-type optotype pattern is provided between the grid pattern where the optotypes 1 and 2 are located and a grid pattern 1 on the right side of the grid pattern where the optotypes 1 and 2 are located. Grid patterns 1 to 3 on an upper side of the grid pattern where the optotype 3 is located, a grid pattern on a lower side of the grid pattern where the optotype 3 is located and grid patterns 1 and 2 on the lower side of the grid pattern where the optotypes 1 and 2 are located are all colored grid patterns. A blank distance between each of the optotypes of the first type and an edge of the grid pattern where the optotype is located is not less than half of a width of one optotype of the first type. A blank distance between each of the optotypes of the second type and an edge of the grid pattern where the optotype is located is not less than half of the width of one optotype of the second type. A blank distance between two adjacent optotypes of the second type is not less than half of the width of one optotype of the second type. There are four optotype directions. The directions of the two optotypes in the same grid pattern are different, and the directions of any two adjacent optotypes are also different.

Figure 19:
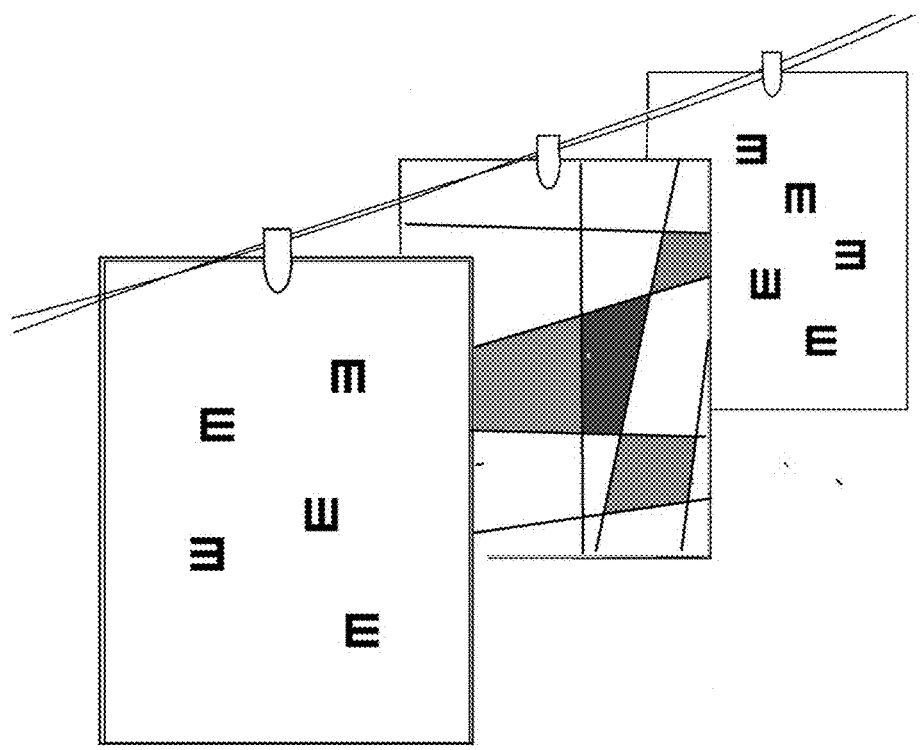

Embodiment 19: The present disclosure provides a heterogeneous visual acuity chart. Referring to FIG. 19, the heterogeneous visual acuity chart includes two types of optotypes of different sizes and a perspective that affects a visual depth of the optotypes of different sizes. A first type of optotypes include five small-sized optotypes, and a second type of optotypes include five large-sized optotypes. The first type of optotypes and the second type of optotypes are provided in different positions. The perspective includes a first rectangle, a second rectangle and a third rectangle. The three rectangles are arranged in sequence from front to back, and corresponding corner lines (dashed lines in the figure) of the three rectangles are concentrated at one point along a depth direction to define a three-dimensional space. Specifically, grid lines are provided on the second rectangle, and some of the grid lines are filled with a color. The first type of optotypes are provided on the third rectangle. Among the five optotypes from top to bottom, an optotype 1 is provided in an upper left corner of the first rectangle. An optotype 2 is provided in a lower right corner of the optotype 1. An optotype 3 is provided in a lower right corner of the optotype 2. An optotype 4 is provided in a lower left corner of the optotype 3. An optotype 5 is located at a lower right corner of the optotype 4 and a lower left corner of the optotype 3. A blank distance between each of the optotypes and an edge of the first rectangle is not less than half of a width of one optotype of the first type. A blank distance between two adjacent optotypes is not less than half of the width of one optotype of the first type. There are four optotype directions, and the directions of any two adjacent optotypes are different. The second type of optotypes are provided on the first rectangle. Among the five optotypes from top to bottom, an optotype 1 is provided in an upper right corner of the first rectangle. An optotype 2 is provided below and to the left of the optotype 1. An optotype 3 is provided below and to the right of the optotype 2. An optotype 4 is provided below and to the left of the optotype 2. An optotype 5 is located in a lower left corner of the optotype 3. A blank distance between each of the optotypes and an edge of the third rectangle is not less than half of a width of one optotype of the second type. A blank distance between two adjacent optotypes is not less than half of the width of one optotype of the second type. There are four optotype directions, and the directions of any two adjacent optotype are different.

Figure 20:
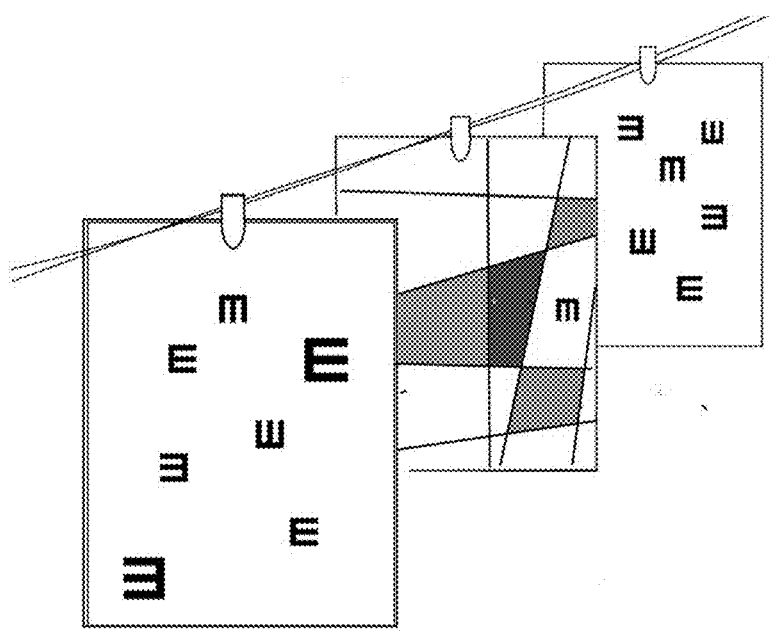

Embodiment 20: The present disclosure provides a heterogeneous visual acuity chart. Referring to FIG. 20, the heterogeneous visual acuity chart includes two types of optotypes of different sizes, a perspective that affects a visual depth of the optotypes of different sizes and four E-type optotype patterns composed of lines. A first type of optotypes include five small-sized optotypes, and a second type of optotypes include five large-sized optotypes. The first type of optotypes and the second type of optotypes are provided in different positions. The four E-type optotype patterns include two large-sized E-type optotype pattern of the same size and two small-sized E-type optotype patterns of the same size. The size of the small-sized E-type optotype pattern is not more than 0.5 times that of the first type of optotype, and the size of the large-sized E-type optotype pattern is not less than 1.5 times that of the second type of optotype. The perspective is the same as that in Embodiment 19. Specifically, grid lines are provided on the second rectangle, and some of the grid lines are filled with a color. The first type of optotypes are provided on the third rectangle. Among the five optotypes from top to bottom, an optotype 1 is provided in an upper left corner of the first rectangle. An optotype 2 is provided in a lower right corner of the optotype 1. An optotype 3 is provided in a lower right corner of the optotype 2. An optotype 4 is provided in a lower left corner of the optotype 3. An optotype 5 is located at a lower right corner of the optotype 4 and a lower left corner of the optotype 3. A first small-sized E-type optotype pattern is located on a right side of the optotype 1 and in an upper right corner of the optotype 2, and a second small-sized E-type optotype pattern is provided in a blank grid of the second rectangle. A blank distance between each of the optotypes and an edge of the pattern (including the third rectangle and the E-type optotype pattern) is not less than half of a width of one optotype of the first type. A blank distance between two adjacent optotypes is not less than half of the width of one optotype of the first type. There are four optotype directions, and the directions of any two adjacent optotypes are different. The second type of optotypes are provided on the first rectangle. Among the five optotypes from top to bottom, an optotype 1 is provided in an upper middle part of the first rectangle. An optotype 2 is provided below and to the left of the optotype 1. An optotype 3 is provided below and to the right of the optotype 2. An optotype 4 is provided below and to the left of the optotype 2. An optotype 5 is located in a lower left corner of the optotype 3 and a lower left corner of the optotype 4. A first large-sized E-type optotype pattern is located in a lower right corner of the optotype 1 and a lower right corner of the optotype 3, and a second large-sized E-type optotype pattern is located in a lower left corner of the optotype 4. A blank distance between each of the optotypes and an edge of the pattern (including the third rectangle and the E-type optotype pattern) is not less than half of a width of one optotype of the second type. A blank distance between two adjacent optotypes is not less than half of the width of one optotype of the second type. There are four optotype directions, and the directions of any two adjacent optotype are different. Grid lines are provided on the second rectangle, and some of the grid lines are filled with a color.

Figure 21:
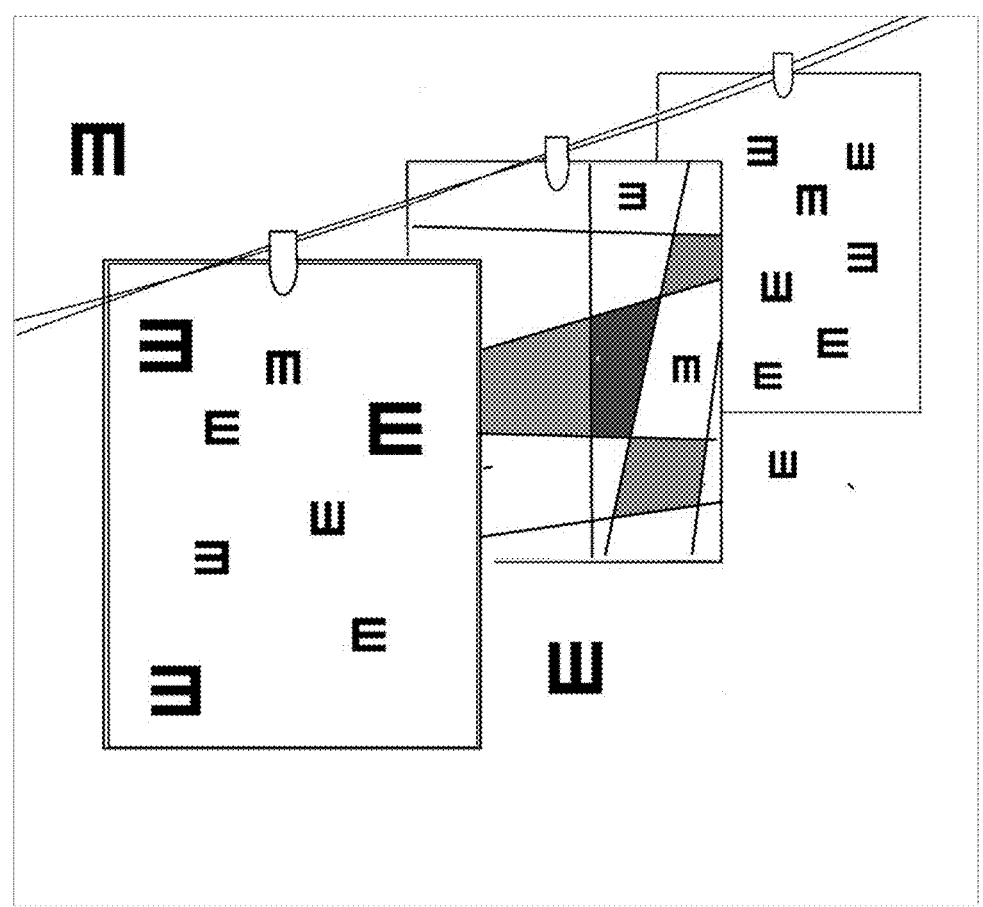

Embodiment 21: The present disclosure provides a heterogeneous visual acuity chart. Referring to FIG. 21, the heterogeneous visual acuity chart includes two types of optotypes of different sizes, a perspective that affects a visual depth of the optotypes of different sizes and 10 E-type optotype patterns composed of lines. A first type of optotypes include five small-sized optotypes, and a second type of optotypes include five large-sized optotypes. The first type of optotypes and the second type of optotypes are provided in different positions. The 10 E-type optotype patterns include 5 large-sized E-type optotype pattern of the same size and 5 small-sized E-type optotype patterns of the same size. The size of the small-sized E-type optotype pattern is not more than 0.5 times that of the first type of optotype, and the size of the large-sized E-type optotype pattern is not less than 1.5 times that of the second type of optotype. The perspective is the same as that in Embodiment 19. Specifically, grid lines are provided on a second rectangle, and some of the grid lines are filled with a color. The first type of optotypes are provided on a third rectangle. Among the five optotypes from top to bottom, an optotype 1 is provided in an upper left corner of the first rectangle. An optotype 2 is provided in a lower right corner of the optotype 1. An optotype 3 is provided in a lower right corner of the optotype 2. An optotype 4 is provided in a lower left corner of the optotype 3. An optotype 5 is located at a lower right corner of the optotype 4 and a lower left corner of the optotype 3. A first small-sized E-type optotype pattern is located on a right side of the optotype 1 and an upper right corner of the optotype 2. Second and third small-sized E-type optotype pattern are located in a blank grid of the second rectangle. A fourth small-sized E-type optotype pattern is located at a lower left corner of the optotype 4. A fifth small-sized E-type optotype pattern is located on a lower side of the third rectangle. A blank distance between each of the optotypes and an edge of the pattern (including the third rectangle and the E-type optotype pattern) is not less than half of a width of one optotype of the first type. A blank distance between two adjacent optotypes is not less than half of the width of one optotype of the first type. There are four optotype directions, and the directions of any two adjacent optotypes are different. The second type of optotypes are provided on the first rectangle. Among the five optotypes from top to bottom, an optotype 1 is provided in an upper middle part of the first rectangle. An optotype 2 is provided below and to the left of the optotype 1. An optotype 3 is provided below and to the right of the optotype 2. An optotype 4 is provided below and to the left of the optotype 2. An optotype 5 is located in a lower right corner of the optotype 3 and a lower right corner of the optotype 4. A first large-sized E-type optotype pattern is located in a lower right corner of the optotype 1 and an upper right corner of the optotype 2. A second large-sized E-type optotype pattern is located in a lower left corner of the optotype 4. A third large-sized E-type optotype pattern is located on a right side of the first rectangle. A fourth large-sized E-type optotype pattern is located in an upper right corner of the first rectangle. A fifth large-sized E-type optotype pattern is located in an upper left corner of the first rectangle. A blank distance between each of the optotypes and an edge of the pattern (including the third rectangle and the E-type optotype pattern) is not less than half of a width of one optotype of the second type. A blank distance between two adjacent optotypes is not less than half of the width of one optotype of the second type. There are four optotype directions, and the directions of any two adjacent optotype are different. Grid lines are provided on the second rectangle, and some of the grid lines are filled with a color.

Figure 22:
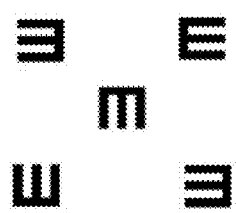
FIG. 22 is a view illustrating a structure of a single visual acuity chart according to Embodiment 22 of the present disclosure.

Embodiment 22: The present disclosure provides a single visual acuity chart. Referring to FIG. 22, the single visual acuity chart includes five optotypes of the same size. The five optotypes are arranged in a square, of which four optotypes are located at four corners of the square, and one optotype is located at the center of the square. A blank distance between any two adjacent optotypes is more than half of a width of the optotype. The directions of any two adjacent optotypes in a vertical direction are different, and the directions of any two adjacent optotypes in a horizontal direction are different.

Further, the single visual acuity chart may be provided with 7, 9 or more optotypes.

Further, the optotypes in the single visual acuity chart may be arranged in a row, or arranged in a column, or arranged in multiple rows and multiple columns, or arranged randomly.

Figure 23:
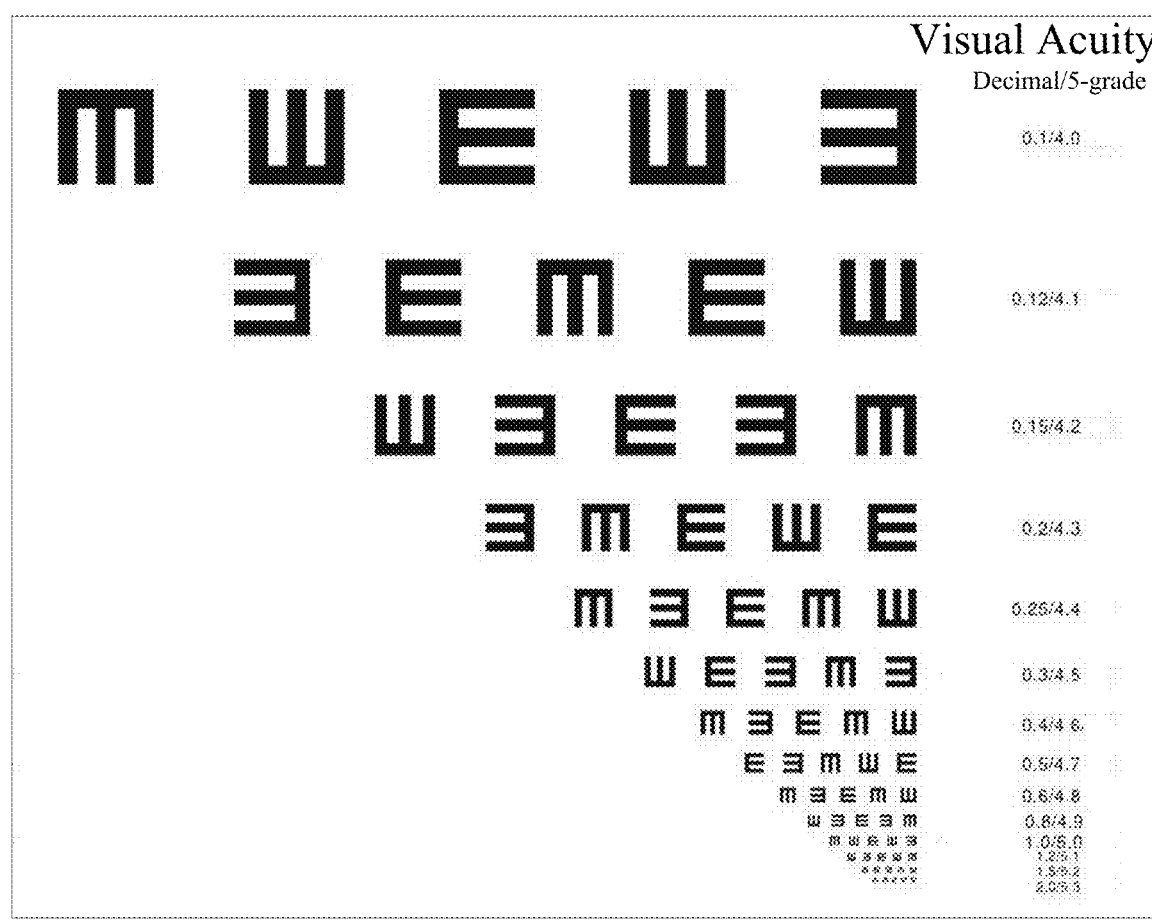
FIG. 23 is a view illustrating a structure of a standard logarithmic visual acuity chart according to Embodiment 23 of the present disclosure.

Embodiment 23: The present disclosure provides a standard logarithmic visual acuity chart. Referring to FIG. 23, the standard logarithmic visual acuity chart is formulated according to the *GB* 11533 *Standard for Logarithmic Visual Acuity Charts*, which adjusts the number of optotypes in each row of the standard logarithmic distant visual acuity chart (Appendix A) to 5. Specifically, the standard logarithmic visual acuity chart includes 14 rows of optotypes arranged in order of size from top to bottom. According to a 5-grade notation, the 14 optotypes correspond to visual acuities 4.0, 4.1, 4.2, 4.3, 4.4, 4.5, 4.6, 4.7, 4.8, 4.9, 5.0, 5.1, 5.2 and 5.3, respectively. These rows have a spacing of 24 mm. A blank distance between any two adjacent optotypes in each row is more than half of a width of the optotype. In FIG. 5, half of the width of the optotype is taken. In order to unify the criteria for identifying each type of optotype in the process of visual acuity testing, the number of each type of optotype is the same. In addition, beside the number of 5, there may be 7, 9 or more optotypes in each row.

Figure 24:
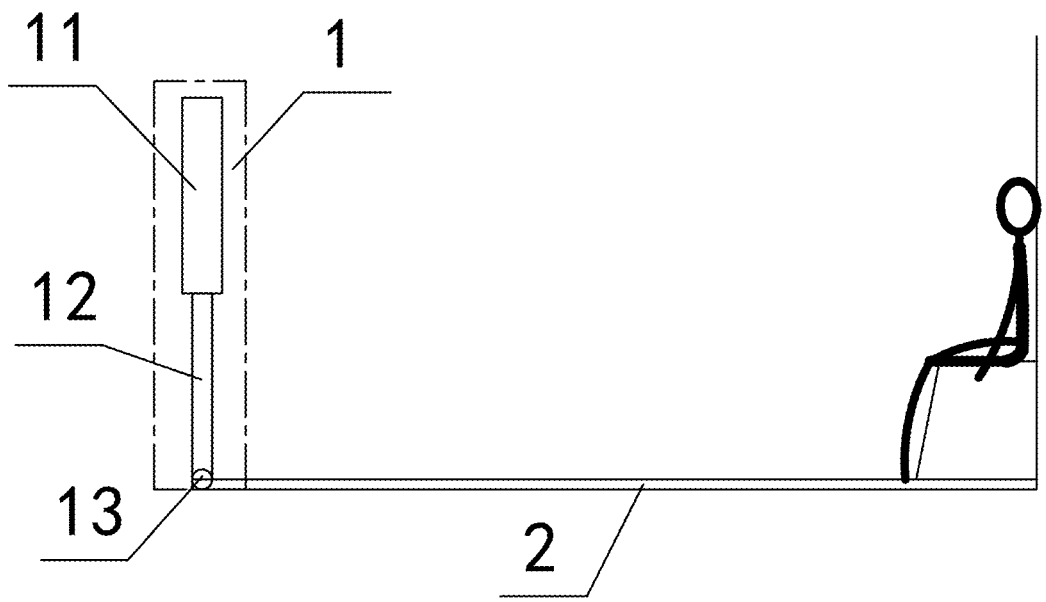
FIG. 24 is a view illustrating a structure of a visual acuity testing device according to Embodiment 24 of the present disclosure.

Embodiment 24: Referring to FIG. 24, the present disclosure provides a visual acuity testing device. The visual acuity testing device includes a visual acuity chart, a first support device 1 and a distance measuring device 2. The visual acuity chart is detachably provided on a support plate 11 of the first support device. The distance measuring device 2 is used to measure a distance between a subject and a testing visual acuity chart. The visual acuity chart includes the heterogeneous visual acuity chart described in any one of the above Embodiments 1 to 21 and the standard logarithmic visual acuity chart described in Embodiment 23. The testing visual acuity chart is the visual acuity chart. During measurement, the subject is away from or close to the first support device, and the test distance between the subject and the visual acuity chart is changed.

In a preferred implementation of this embodiment, the visual acuity chart further includes the single visual acuity chart described in Embodiment 22.

In a preferred implementation of this embodiment, the above visual acuity testing device further includes a moving device. The moving device is used to realize relative movement between the testing visual acuity chart and the subject.

Specifically, the first support device includes a first bracket 12 at the bottom and a support plate 11 provided on the first bracket 12. The moving device is a wheel 13 fixed at the bottom of the first bracket 12.

In a preferred solution of this embodiment, the distance measuring device is a ruler provided on the ground, and the ruler is provided between the first support device and the subject. When the test distance between the subject and the visual acuity chart is changed, the first support device is moved along the ruler, and after the first support device stops moving, the test distance corresponding to the optotype is obtained.

In another preferred solution of this embodiment, the distance measuring device is a sliding rail with a ruler. The sliding rail is provided between the first support device and the subject, and the wheel is in a sliding fit with the sliding rail. When the test distance between the subject and the visual acuity chart is changed, the first support device is moved along the sliding rail, and when the first support device stops moving, the test distance corresponding to the optotype is obtained.

Any other device capable of distance measurement may be used as the distance measuring device of this embodiment.

In this embodiment, in the heterogeneous visual acuity chart, the size of the small-sized optotype is 0.8 times that of the large-sized optotype.

In the visual acuity testing device of this embodiment, there may be 5, 6, 7, 8, 9 or more optotypes of each type in various visual acuity charts, which may specifically be set according to actual conditions.

In addition, in order to meet the illumination requirements of the visual acuity chart, at least one illuminating lamp is provided at each of four corners of the support plate 11, and any two adjacent illuminating lamps are symmetrically arranged.

In a preferred implementation of this embodiment, the visual acuity testing device further includes a visual acuity chart mounting and adjustment device. The visual acuity chart mounting and adjustment device includes first magnets and second magnets that are mutually attracted. The first magnets are fixedly provided on the heterogeneous visual acuity chart, the standard logarithmic visual acuity chart and the single visual acuity chart. The second magnets are provided on the support plate 11 of the first support device. Through a magnetic force between the first magnets and the second magnets, the heterogeneous visual acuity chart, the standard logarithmic visual acuity chart and the single visual acuity chart are automatically provided on the support plate of the first support device.

The subject may utilize reference objects to find the rule of the optotypes, and it is easy for him to feign when there are many reference objects. In order to prevent the subject from utilizing the reference objects for feigning, the first magnets are fixedly provided on the back of various visual acuity charts, and at least one first magnet is provided at each of four corners respectively. The first magnets may be ring-shaped, bar-shaped, square-shaped or triangular, etc. They may be regular or irregular, depending on the size of the visual acuity chart. The second magnets have the same number and the same or similar shape as the first magnets, and their mounting positions are corresponding to those of the first magnets, respectively. The second magnets are embedded in the support plate of the first support device, such that upper surfaces of the second magnets are on the same level as a surface of the support plate.

Further, in order to prevent the subject from utilizing the support plate used to provide the visual acuity chart as a reference object for feigning, the support plate is in a color that is the same as a background color of the visual acuity chart.

The visual acuity testing device tests as follows:

S1: Perform a visual acuity test with the heterogeneous visual acuity chart; move a testing heterogeneous visual acuity chart from far to near or from near to far relative to a subject so as to change a test distance between the subject and the testing heterogeneous visual acuity chart, until a number of optotypes correctly identified by the subject in any set of optotypes reaches half of a total number or more and a number of optotypes correctly identified by the subject in the other set of optotypes is less than half of a total number; and record the number of correctly identified optotypes in each of the two types in the heterogeneous visual acuity chart, calculate and record a tested visual acuity.

S2: Perform a visual acuity test with a single visual acuity chart; move a testing single visual acuity chart relative to a subject from far to near so as to change a test distance between the subject and the testing single visual acuity chart, until a farthest distance where the subject correctly identifies more than half of the optotypes; and calculate and record a tested visual acuity.

S3: Perform a standard visual acuity test with a standard logarithmic visual acuity chart, where the subject is in a test distance from a testing standard logarithmic visual acuity chart, and record a tested visual acuity.

S4: Test with the heterogeneous visual acuity chart and the single visual acuity chart each for ≥1 time for the same subject, and determine whether a visual acuity of the subject is true according to a difference between visual acuities tested with the heterogeneous visual acuity chart, a difference between visual acuities tested with the single visual acuity chart, a difference between visual acuities tested with the heterogeneous visual acuity chart and the single visual acuity chart and a difference between visual acuities tested with the single visual acuity chart and a standard logarithmic visual acuity chart. Specifically, the determining whether a visual acuity of the subject is true includes:

Define a row of the standard logarithmic visual acuity chart as a standard visual acuity row.

Determine that a visual acuity tested with the standard logarithmic visual acuity chart is true if these differences are all within one standard visual acuity row, that is, the differences ≤1 standard visual acuity row.

Determine that the subject is uncooperative and the visual acuity tested with the standard logarithmic visual acuity chart is false, if one of these differences reaches two standard visual acuity rows or more, that is, the difference ≥2 standard visual acuity rows, or the subject does not cooperate to complete the test.

Determine that the subject is likely to be subjectively uncooperative and the visual acuity tested with the standard logarithmic visual acuity chart is likely to be false, if, although these differences do not reach two standard visual acuity rows, in the test of the heterogeneous visual acuity chart, the subject correctly identifies the small-sized optotype but fails to correctly identify the large-sized optotype, or there is a contradiction hard to be explained reasonably between the tested visual acuities.

In the actual testing process, the distant visual acuity chart (Appendix A) in the *GB 11533 Standard for Logarithmic Visual Acuity Charts* may also be used to replace the above standard logarithmic visual acuity chart. In order to unify the criteria for identifying each type of optotype in the process of visual acuity testing, the above standard logarithmic visual acuity chart may be preferred. Meanwhile, in order to avoid systematic errors caused by the number of different optotypes in the testing process, the number of optotypes maintains the same in the single visual acuity chart and the standard logarithmic visual acuity chart for the same subject.

The visual acuity testing device described in this embodiment adopts different visual acuity charts to alternately test. When the heterogeneous visual acuity chart and the single visual acuity chart are used for testing, the test distance between the subject and the testing visual acuity chart is changed, so as to obtain the best visual acuity of the subject. The best visual acuity means that the subject correctly identifies more than half of the optotypes of a certain size at the farthest test distance or correctly identifies more than half of the smallest optotype at a certain test distance. According to a visual acuity difference between different visual acuity charts or different visual acuity test results, it is determined whether the visual acuity tested with the standard logarithmic visual acuity chart is true, so as to effectively identify a feigned visual acuity and avoid a feigned high visual acuity. Since the visual acuity chart is detachably provided on the first support device, the mounting direction of the visual acuity chart may be manually changed, thereby changing the optotype directions. The rotation directions of all the heterogeneous visual acuity charts involved in the drawings in the specification do not affect the illusion effect.

Figure 25:
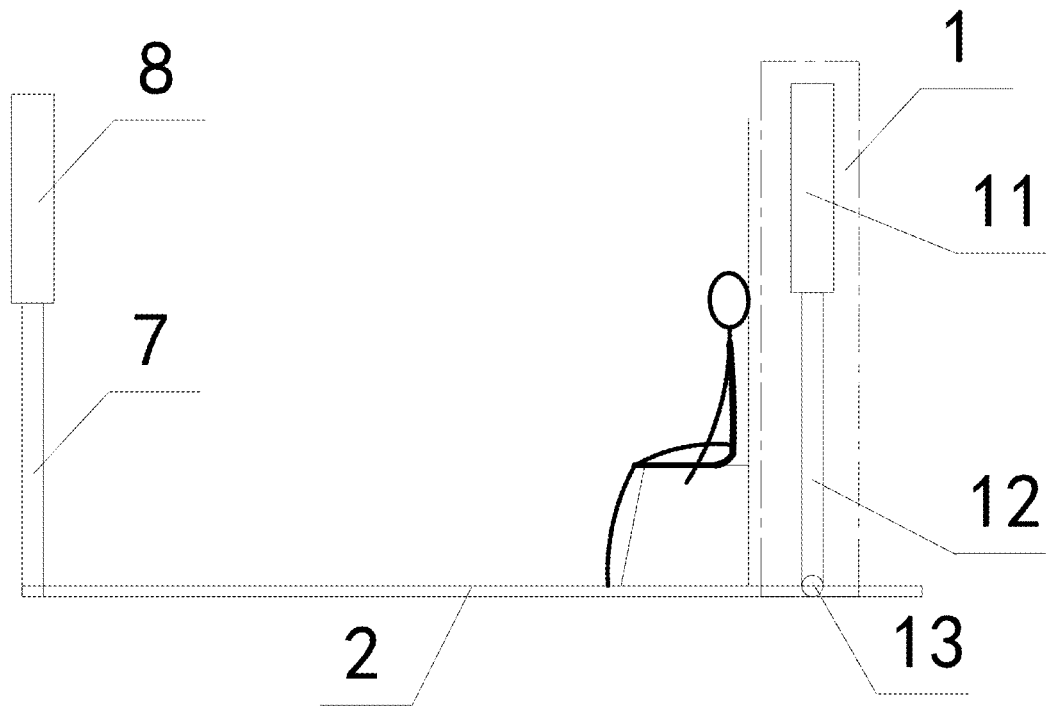
FIG. 25 is a view illustrating a structure of a visual acuity testing device according to Embodiment 25 of the present disclosure.

Embodiment 25: The present disclosure provides a visual acuity testing device. Referring to FIG. 25, the visual acuity testing device includes a visual acuity chart, a first support device 1, a distance measuring device 2, a second support device 7 and a mirror 8. The first support device 1 is provided opposite to the second support device 7. The visual acuity chart is detachably provided on the first support device 1. The mirror is provided on the second support device 7, such that the mirror and the visual acuity chart are opposite to each other. The visual acuity chart includes the heterogeneous visual acuity chart described in any one of the above Embodiments 1 to 21 and the standard logarithmic visual acuity chart described in Embodiment 23. The distance measuring device is used to measure a distance between a subject and a testing visual acuity chart. The testing visual acuity chart is an image of the visual acuity chart in the mirror. During visual acuity testing, the second support device is located in front of the subject, and the first support device is located behind the subject. The subject moves between the first support device and the second support device to change the test distance between the subject and the testing visual acuity chart.

In a preferred implementation of this embodiment, the visual acuity chart further includes the single visual acuity chart described in Embodiment 19.

Referring to FIG. 24, the first support device includes a first bracket 12 at the bottom and a support plate 11 provided on the first bracket 12. The bottom of the first bracket 12 is provided with a wheel 13. The second support device is a second bracket, and the mirror is located on the top of the second bracket.

The visual acuity testing device of this embodiment further includes a moving device. The moving device is used to realize movement of the subject relative to the testing visual acuity chart. Specifically, the moving device is a wheel 13 fixed at the bottom of the first support bracket 12, or a wheel fixed at the bottom of the second support bracket.

In a preferred implementation of this embodiment, the visual acuity testing device further includes a visual acuity chart mounting and adjustment device. The structure of the visual acuity chart mounting and adjustment device is the same as that of Embodiment 21, and will not be repeated here.

In a preferred solution of this embodiment, the distance measuring device is a ruler provided on the ground, and the ruler is provided between the first support device and the second support device. When the wheel is fixed at the bottom of the first support device, the first support device is moved along the ruler to change the distance between the subject and the testing visual acuity chart. After the first support device stops moving, the test distance corresponding to the optotype is obtained. When the wheel is fixed at the bottom of the second support device, the second support device is moved along the ruler to change the distance between the subject and the testing visual acuity chart. After the second support device stops moving, the test distance corresponding to the optotype is obtained.

In this embodiment, the testing visual acuity chart is the image of the visual acuity chart in the mirror. The mirror interferes with the subject's perception of distance and increases the test accuracy. When the first support device or the second support device is moved simultaneously with the subject, it interferes with the subject's determination of the distance, thereby increasing the test accuracy.

In another preferred solution of this embodiment, the distance measuring device is a sliding rail with a ruler. The ruler is provided between the first support device and the second support device, and the wheel is in a sliding fit with the sliding rail. By changing the test distance between the subject and the testing visual acuity chart, the test distance corresponding to the optotype is obtained.

The testing steps of this embodiment are the same as those in Embodiment 24, and will not be repeated here.

Other content of this embodiment is the same as those in Embodiment 24, and will not be repeated here.

Figure 26:
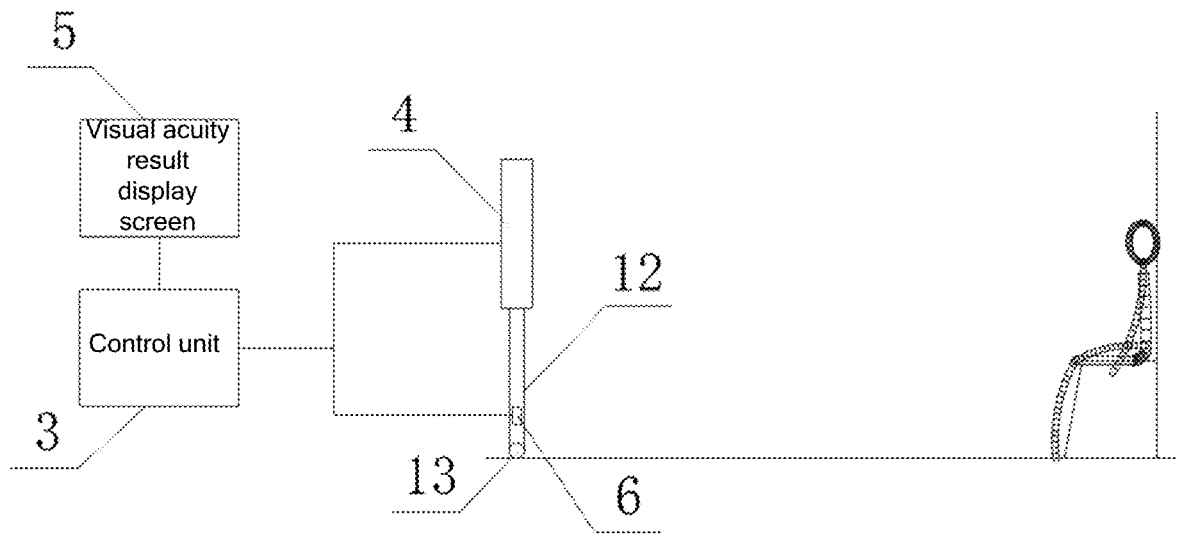
FIG. 26 is a view illustrating a structure of a visual acuity testing device according to Embodiment 26 of the present disclosure.
Figure 27:
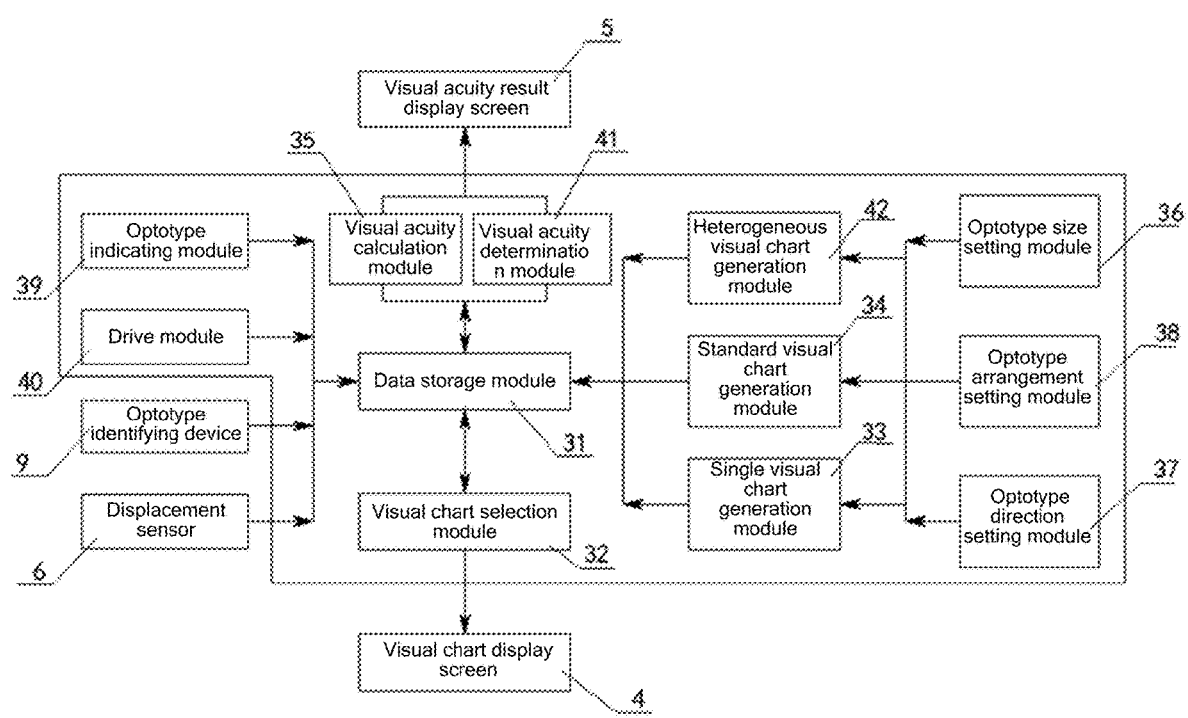
FIG. 27 is a view illustrating a structure of a control unit of a visual acuity testing device according to Embodiment 27 of the present disclosure.

Embodiment 26: The present disclosure provides a visual acuity testing device. Referring to FIGS. 26 and 27, the visual acuity testing device includes a first support device, a control unit 3, a visual acuity chart display screen 4 and a visual acuity result display screen 5 connected to the control unit 3, and a displacement sensor 6 connected to the control unit 3. The visual acuity chart display screen 4 and the displacement sensor 6 are respectively provided on the first support device. The control unit 3 is provided with a data storage module 31, a visual acuity chart selection module 32, a heterogeneous visual acuity chart generation module 42 for generating the heterogeneous visual acuity chart, a standard visual acuity chart generation module 34 for generating the standard logarithmic visual acuity chart and a visual acuity calculation module 35 for calculating a visual acuity. The visual acuity chart calculation module 35, the visual acuity chart selection module 32, the heterogeneous visual acuity chart generation module 42 and the standard visual acuity chart generation module 34 are respectively connected to the data storage module 31.

Further, the visual acuity testing device further includes a single visual acuity chart generation module 33 for generating the single visual acuity chart in Embodiment 22, and the single visual acuity chart generation module 33 is connected to the data storage module 31.

The single visual acuity chart generation module 33, the heterogeneous visual acuity chart generation module 42 and the standard visual acuity chart generation module 34 respectively deliver the generated single visual acuity chart, heterogeneous visual acuity chart and standard logarithmic visual acuity chart to the data storage module 31 for storage.

The visual acuity chart selection module 32 selects a visual acuity chart from the data storage module 31, and sends the selected visual acuity chart to the visual acuity chart display screen 4 for display. A tester performs a visual acuity test on the subject according to the visual acuity chart displayed on the visual acuity chart display screen 4, and enters a visual acuity test result into the data storage module 31. The data storage module 31 stores an optotype visual acuity of the subject in real time. In the process, the displacement sensor 6 sends the test distance between the subject and the first support device 12 to the data storage module 31 for storage. The visual acuity calculation module 35 calculates a visual acuity according to the test distance and the optotype visual acuity, and sends the calculated visual acuity to the data storage module 31 for storage. The data storage module 31 sends the tested visual acuity to the visual acuity result display screen 5 for display.

As a preferred implementation of this embodiment, the visual acuity testing device further includes a smart moving device, an optotype indicating module 39 and an optotype identifying device 9. The smart moving device includes a wheel 13 at a bottom of the first support device, a drive motor connected to the wheel 13 and a brake on the wheel. The drive motor and the brake are respectively connected to a drive module 40 in the control unit. The optotype indicating module 39 is used to indicate optotypes to be identified by the subject. The optotype identifying device 9 is used to confirm the start of identifying the optotypes and input an identification result on the optotypes to be identified. The drive module 40, the optotype indicating module 39 and the optotype identifying device 9 are respectively connected to the data storage module 31.

The drive module 40 drives a motor to work according to the visual acuity chart selected by the visual acuity chart selection module 32, and drives the first support device 12 to move to a position to test. Specifically, when the standard logarithmic visual acuity chart is used, the first support device 12 is moved to a set test distance. For the standard logarithmic visual acuity chart in Embodiment 23, the test distance between the eye nodal point of the subject and the visual acuity chart is 5 m. When the single visual acuity chart is used, the first support device 12 is moved to the subject from far to near. When the heterogeneous visual acuity chart is used, the first support device 12 is moved to the subject from far to near or from near to far. When the subject is ready to identify the optotypes in the visual acuity chart, the optotype identifying device 9 confirms the start of identification. The data storage module 31 obtains and stores the distance of the subject from the single visual acuity chart or the heterogeneous visual acuity chart at the start of identification. The optotype indicating module 39 sequentially indicates the optotypes in the visual acuity chart to be identified by the subject. The subject enters an identification result showing the directions of the optotypes (up, down, left, right) or non-clarity in the optotype identifying device. The identification result is sent to the data storage module 31 for storage. The visual acuity calculation module 35 first obtains the visual acuity of the optotype indicated by the optotype indicating module 39 from the data storage module 31, and then determines whether the subject identifies more than half of the optotypes according to the identification result. If the determination result is yes, the visual acuity of the subject is calculated according to the test distance and the tested visual acuity of the optotype, and the visual acuity of the subject is sent to the data storage module 31 for storage. The data storage module 31 sends tested visual acuities (including those tested by the single visual acuity chart, the heterogeneous visual acuity chart and the standard logarithmic visual acuity chart) to the visual acuity result display screen 5 for display.

As a preferred implementation of this embodiment, the control unit further includes a feigned visual acuity determination module 41. The feigned visual acuity determination module 41 is connected to the data storage module 31. The feigned visual acuity determination module is used to obtain visual acuities tested with the single visual acuity chart, the heterogeneous visual acuity chart and the standard logarithmic visual acuity chart from the data storage module 31, compare multiple visual acuities to determine whether a visual acuity is false according to the method described in Embodiment 20 or 21, send a determination result to the data storage module 31 for storage, and send the determination result on the subject to the visual acuity result display screen 5 for display.

By alternately testing the visual acuity of the subject with the single visual acuity chart and the heterogeneous visual acuity chart, the present disclosure improves the test accuracy, reduces the possibility for the subject to feign a visual acuity, and can effectively identify feigned high and low visual acuities.

Referring to FIG. 27, the control unit 3 further includes an optotype size setting module 36 for setting optotype sizes. The optotype size setting module 36 is connected to the heterogeneous visual acuity chart generation module 42, the single visual acuity chart generation module 33 and the standard visual acuity chart generation module 34, respectively. The optotype size setting module sets optotype sizes, and sends the set optotype sizes to the heterogeneous visual acuity chart generation module 42, the single visual acuity chart generation module 33 and the standard visual acuity chart generation module 34, respectively. The heterogeneous visual acuity chart generation module 42, the single visual acuity chart generation module 33 and the standard visual acuity chart generation module 34 generate a visual acuity chart according to the obtained optotype sizes, and send the generated visual acuity chart to the data storage module 31 for storage. The sizes of the optotypes in the generated visual acuity chart are the same as the set optotype sizes.

Referring to FIG. 27, the control unit 3 further includes an optotype direction setting module 37 for setting optotype directions. The optotype direction setting module 37 is respectively connected to the heterogeneous visual acuity chart generation module 42, the single visual acuity chart generation module 33 and the standard visual acuity chart generation module 34. The optotype direction setting module sets the optotype directions, and sends the set optotype directions to the heterogeneous visual acuity chart generation module 42, the single visual acuity chart generation module 33 and the standard visual acuity chart generation module 34, respectively. The heterogeneous visual acuity chart generation module 42, the single visual acuity chart generation module 33 and the standard visual acuity chart generation module 34 generate a visual acuity chart according to the obtained optotype directions, and send the generated visual acuity chart to the data storage module 31 for storage. The directions of the optotypes in the generated visual acuity chart are the same as the set optotype directions.

Referring to FIG. 27, the control unit 3 further includes an optotype arrangement setting module 38 for arranging optotype positions. The optotype arrangement setting module 38 is respectively connected to the heterogeneous visual acuity chart generation module 42, the single visual acuity chart generation module 33 and the standard visual acuity chart generation module 34. The optotype arrangement setting module 38 sets the optotype positions, and sends the set optotype positions to the heterogeneous visual acuity chart generation module 42, the single visual acuity chart generation module 33 and the standard visual acuity chart generation module 34, respectively. The heterogeneous visual acuity chart generation module 42, the single visual acuity chart generation module 33 and the standard visual acuity chart generation module 34 generate a visual acuity chart according to the obtained optotype positions, and send the generated visual acuity chart to the data storage module 31 for storage. The positions of the optotypes in the generated visual acuity chart are the same as the set optotype positions.

Referring to FIG. 26, the first support device includes a first bracket 12 and a wheel 13 at the bottom of the first bracket 12. The visual acuity chart display screen 4 is provided on the top of the first bracket 12, and the displacement sensor 6 is provided on a lower part of the first bracket 12.

In the visual acuity testing device of this embodiment, there may be 5, 6, 7, 8, 9 or more optotypes in various visual acuity charts, which may specifically be set according to actual conditions.

The visual acuity testing device described in this embodiment adopts different visual acuity charts to alternately test. When the heterogeneous visual acuity chart and the single visual acuity chart are used for testing, the test distance between the subject and the visual acuity chart is changed, so as to obtain the best visual acuity of the subject. The best visual acuity means that the subject correctly identifies more than half of the optotypes of a certain size at the farthest test distance or correctly identifies more than half of the smallest optotype at a certain test distance. According to a visual acuity difference between different visual acuity charts or visual acuity test results, it is determined whether a visual acuity tested by the standard logarithmic visual acuity chart is true so as to effectively identify a feigned visual acuity and avoid a feigned high visual acuity.

The testing steps of this embodiment are the same as those in Embodiment 24, and will not be repeated here. Different from Embodiment 24, in this embodiment, the directions, sizes and positions of the optotypes are automatically changed.

Embodiment 27: The present disclosure provides a visual acuity testing method, which uses the visual acuity testing device according to any one of the above embodiments, and includes the following steps:

S1: Perform a visual acuity test with the heterogeneous visual acuity chart; move a testing heterogeneous visual acuity chart from far to near or from near to far relative to a subject so as to change a test distance between the subject and the testing heterogeneous visual acuity chart, until a number of optotypes, correctly identified by the subject, in any set of optotypes is less than half; and record the number of correctly identified optotypes in each of the two types in the heterogeneous visual acuity chart, calculate and record a tested visual acuity.

S2: Perform a standard visual acuity test with a standard logarithmic visual acuity chart, where the subject is in a test distance from a testing standard logarithmic visual acuity chart, and record a tested visual acuity.

S3: Test with the heterogeneous visual acuity chart for ≥1 time for the same subject, and determine whether a visual acuity of the subject is true according to a difference between visual acuities tested with the heterogeneous visual acuity chart and a difference between visual acuities tested with the heterogeneous visual acuity chart and the standard logarithmic visual acuity chart. Specifically, the determining whether a visual acuity of the subject is true includes:

Define a row of the standard logarithmic visual acuity chart as a standard visual acuity row.

Determine that a visual acuity tested with the standard logarithmic visual acuity chart is true if these differences are all within one standard visual acuity row, that is, the differences ≤1 standard visual acuity row.

Determine that the subject is uncooperative and the visual acuity tested with the standard logarithmic visual acuity chart is false, if one of these differences reaches two standard visual acuity rows or more, that is, the difference ≥2 standard visual acuity rows, or the subject does not cooperate to complete the test.

Determine that the subject is likely to be subjectively uncooperative and the visual acuity tested with the standard logarithmic visual acuity chart is likely to be false, if, although these differences do not reach two standard visual acuity rows, when tested with the heterogeneous visual acuity chart, the subject correctly identifies an optotype in the first type but fails to correctly identify an optotype in the second type, or there is a contradiction hard to be explained reasonably between the tested visual acuities.

During the testing process, by increasing the number of tests in Step S1, the determination accuracy can be improved. In addition, by continuously changing the distance between the testing heterogeneous visual acuity chart and the subject from far to near and from near to far, the determination accuracy can also be improved.

Embodiment 28: The present disclosure provides a visual acuity testing method, which uses the visual acuity testing device according to any one of the above embodiments, and includes the following steps:

S1: Perform a visual acuity test with the heterogeneous visual acuity chart; move a testing heterogeneous visual acuity chart from far to near or from near to far relative to a subject so as to change a test distance between the subject and the testing heterogeneous visual acuity chart, until a number of optotypes, correctly identified by the subject, in any set of optotypes is less than half; and record the number of correctly identified optotypes in each of the two types in the heterogeneous visual acuity chart, calculate and record a tested visual acuity.

S2: Perform a visual acuity test with a single visual acuity chart; move a testing single visual acuity chart relative to a subject from far to near so as to change a test distance between the subject and the testing single visual acuity chart, until a farthest distance where the subject correctly identifies more than half of the optotypes; and calculate and record a tested visual acuity.

S3: Perform a standard visual acuity test with a standard logarithmic visual acuity chart, where the subject is in a test distance from a testing standard logarithmic visual acuity chart, and record a tested visual acuity.

S4: Test with the heterogeneous visual acuity chart and the single visual acuity chart each for ≥1 time for the same subject, and determine whether a visual acuity of the subject is true according to a difference between visual acuities tested with the heterogeneous visual acuity chart, a difference between visual acuities tested with the single visual acuity chart, a difference between visual acuities tested with the heterogeneous visual acuity chart and the single visual acuity chart and a difference between visual acuities tested with the single visual acuity chart and a standard logarithmic visual acuity chart. Specifically, the determining whether a visual acuity of the subject is true includes:

Define a row of the standard logarithmic visual acuity chart as a standard visual acuity row.

Determine that a visual acuity tested with the standard logarithmic visual acuity chart is true if these differences are all within one standard visual acuity row, that is, the differences ≤1 standard visual acuity row.

Determine that the subject is uncooperative and the visual acuity tested with the standard logarithmic visual acuity chart is false, if one of these differences reaches two standard visual acuity rows or more, that is, the difference ≥2 standard visual acuity rows, or the subject does not cooperate to complete the test.

Determine that the subject is likely to be subjectively uncooperative and the visual acuity tested with the standard logarithmic visual acuity chart is likely to be false, if, although these differences do not reach two standard visual acuity rows, when tested with the heterogeneous visual acuity chart, the subject correctly identifies an optotype in the first type but fails to correctly identify an optotype in the second type, or there is a contradiction hard to be explained reasonably between the tested visual acuities.

Among the above steps, steps S1, S2, and S3 may be interchanged with each other. For example, steps S1 and S2 may be interchanged below. S1: Perform a visual acuity test with a single visual acuity chart; move a testing single visual acuity chart relative to a subject from far to near so as to change a test distance between the subject and the testing single visual acuity chart, until a farthest distance where the subject correctly identifies more than half of the optotypes; and calculate and record a tested visual acuity. S2: Perform a visual acuity test with the heterogeneous visual acuity chart; move a testing heterogeneous visual acuity chart from far to near or from near to far relative to a subject so as to change a test distance between the subject and the testing heterogeneous visual acuity chart, until a number of optotypes, correctly identified by the subject, in any set of optotypes is less than half; and record the number of correctly identified optotypes in each of the two types in the heterogeneous visual acuity chart, calculate and record a tested visual acuity. For example, steps S1 and S3 may be interchanged below. S1: Perform a standard visual acuity test with a standard logarithmic visual acuity chart, where the subject is in a test distance from a testing standard logarithmic visual acuity chart, and record a tested visual acuity. S3: Perform a visual acuity test with the heterogeneous visual acuity chart; move a testing heterogeneous visual acuity chart from far to near or from near to far relative to a subject so as to change a test distance between the subject and the testing heterogeneous visual acuity chart, until a number of optotypes, correctly identified by the subject, in any set of optotypes is less than half; and record the number of correctly identified optotypes in each of the two types in the heterogeneous visual acuity chart, calculate and record a tested visual acuity. For example, steps S2 and S3 may be interchanged below. S2: Perform a standard visual acuity test with a standard logarithmic visual acuity chart, where the subject is in a test distance from a testing standard logarithmic visual acuity chart, and record a tested visual acuity. S3: Perform a visual acuity test with a single visual acuity chart; move a testing single visual acuity chart relative to a subject from far to near so as to change a test distance between the subject and the testing single visual acuity chart, until a farthest distance where the subject correctly identifies more than half of the optotypes; and calculate and record a tested visual acuity. As long as the adjacent steps do not involve the same visual acuity chart, the order between the different visual acuity charts can be interchanged, which will not be repeated here.

During visual acuity testing, the test distance varies within 2-7 m. The heterogeneous visual acuity chart is moved from 2 m to 7 m or from 7 m to 2 m. The single visual acuity chart is moved from 7 m to 2 m. The heterogeneous visual acuity chart is moved from near to far or from far to near, which facilitates the confusion of the two different optotypes and leads the subject to make incorrect identification, thereby preventing the subject from feigning and improving the test accuracy. The single visual acuity chart is moved from far to near, which can effectively prevent the subject from feigning by memorizing the arrangement order of the optotypes, thereby improving the test accuracy.

During each visual acuity test, the optotype directions in each visual acuity chart are changed manually or automatically, so as to make the optotype directions in each visual acuity chart different in each visual acuity test. By changing the optotype directions, the present disclosure can effectively prevent the subject from feigning by memorizing the arrangement order of the optotypes, thereby improving the test accuracy.

During visual acuity testing, in order to further improve the test accuracy, an optotype size difference in each test exceeds one standard visual acuity row, and two adjacent visual acuity tests are performed with different visual acuity charts. By using different visual acuity charts to test and making that the optotype size difference more than one standard visual acuity row, that is, by changing the optotype sizes for testing, the present disclosure can improve the test accuracy and effectively identify a feigned visual acuity.

During visual acuity testing, in order to further improve the test accuracy, the time interval for each test is at least 5 min. During the time interval, the subject is required to close his eyes to rest in a soundproofed and shaded environment. By requiring the subject to close his eyes to rest at the time interval, the present disclosure can reduce the subject's short-term memory of the optotypes and the test distance, thereby further improving the test accuracy.

In order to ensure the test accuracy, the single visual acuity chart, the heterogeneous visual acuity chart and the standard logarithmic visual acuity chart are used to test at least once. A greater number of tests indicate a higher test accuracy. Specifically, the number of tests and the number of uses of the various visual acuity charts are determined according to the actual situation of the subject.

For example, the single visual acuity chart, the heterogeneous visual acuity chart and the standard logarithmic visual acuity chart are used to test for one time respectively, and the tests are performed in the order of the heterogeneous visual acuity chart, the single visual acuity chart and the standard logarithmic visual acuity chart. Compared with the existing testing methods, in the present disclosure, testing with each of the visual acuity charts for one time improves the test accuracy. However, in the present disclosure, compared with testing with each of the visual acuity charts for multiple times, testing with each of the visual acuity charts for one time has the lowest test accuracy.

For another example, the single visual acuity chart and the standard logarithmic visual acuity chart are used to test for one time respectively, the heterogeneous visual acuity chart is used to test double times, and the tests are performed in the order of the heterogeneous visual acuity chart, the single visual acuity chart, the heterogeneous visual acuity chart and the standard logarithmic visual acuity chart. Testing with the heterogeneous visual acuity chart double times facilitates the identification of a subject who feigns, thereby further improving the test accuracy.

In order to describe the advantages of the heterogeneous visual acuity chart and the visual acuity testing method and device more clearly, the heterogeneous visual acuity chart and the visual acuity testing method and device are described in further detail below with reference to specific experiments.

Experiment:

Subjects: 81 volunteers, age: 19-51, male or female, education level: high school or above to doctoral student, who were clear about the purpose and procedures of the experiment, and were willing to actively cooperate with the experiment. The test distance was 2-7 m. The relationship between the decimal visual acuity, the optotype and the test distance was:

Visual acuity=optotype visual acuity×test distance/5

As shown in FIG. 10, the single visual acuity chart was composed of five optotypes. As shown in FIGS. 1 to 9, the heterogeneous visual acuity chart was composed of two types of optotypes of different sizes. The size of the first type of optotype was 0.8 times that of the second type of optotype, and there were five optotypes in either type.

The relationship between the optotypes and the visual acuities of each visual acuity chart is shown in Table 1.

TABLE 1

| 5-Grade Visual Acuity | Visual Angle α (') | Design Distance D (m) | Side Length of Optotype (mm) | Decimal Visual Acuity V |
|---|---|---|---|---|
| 5-lgα | 10" | 5α | 5 × 5,000 αρ | 1/α |

In Table 1, ρ is a mathematical symbol, the number of radians of 1', being $2.90888 \times 10^{-4}$ rad.

Two testers were assigned to test by using the above visual acuity testing device according to the following steps in sequence:

S1. A first tester tested a true visual acuity of a subject with the standard logarithmic visual acuity chart, which was denoted as a visual acuity 1.

S2. The subject independently chose to feign or not to feign a visual acuity. If the subject chose to feign, the subject decreased or increased his true visual acuity by more than 2 rows. The feigning succeeded if the test of the feigned visual acuity could be repeated. The first tester tested the true or feigned visual acuity of the subject with the standard logarithmic visual acuity chart, which was denoted as a visual acuity 2. If the subject chose to feign, the subject was informed of the change of the tester. During the test by the second tester, the subject maintained the feigned visual acuity. If it was found that the subject did not cooperate, it meant that the feigning failed.

The feigning was aided by a reprint of the standard logarithmic visual acuity chart posted in front of the subject.

S3. The visual acuity chart was replaced with the heterogeneous visual acuity chart, and the second tester continued the visual acuity test on the subject with the heterogeneous visual acuity chart. The heterogeneous visual acuity chart was moved from 2 m to 7 m, until the number of any one type of optotypes correctly identified by the subject did not reach 3, and the number of the other type of optotypes correctly identified by the subject reached 3 or more. The number of the correctly identified optotypes in each of the two types was recorded, and a visual acuity was calculated and recorded, which was denoted as a visual acuity 3.

S4. The visual acuity chart was replaced with the single visual acuity chart, and the second tester continued the visual acuity test on the subject with the single visual acuity chart. The single visual acuity chart was moved from 7 m to the subject until a farthest distance at which the subject correctly identified 3 optotypes or more. The visual acuity was calculated and recorded, which was denoted as a visual acuity 4.

S5. The visual acuity chart was replaced with the heterogeneous visual acuity chart, and the second tester continued the visual acuity test on the subject with the heterogeneous visual acuity chart. The heterogeneous visual acuity chart was moved from 2 m to 7 m, until the number of any one type of optotypes correctly identified by the subject did not reach 3, and the number of the other type of optotypes correctly identified by the subject reached 3 or more. The number of the correctly identified optotypes in each of the two types was recorded, and a visual acuity was calculated and recorded, which was denoted as a visual acuity 5.

S6. The visual acuity chart was replaced with the standard logarithmic visual acuity chart, and the second tester continued the visual acuity test on the subject with the standard logarithmic visual acuity chart. A visual acuity was recorded, which was denoted as a visual acuity 6.

S7. The second tester independently determined the authenticity of the visual acuity 6. Specifically, the authenticity of the visual acuity was determined as follows. If maximum differences between the visual acuity 3, the visual acuity 4, the visual acuity 5 and the visual acuity 6 obtained by the 4 tests performed in steps S3, S4, S5 and S6 were all within one standard visual acuity row (i.e. ≤1 standard visual acuity row), the visual acuity 6 was a true visual acuity. If the visual acuity difference was more than 2 standard visual acuity rows (i.e. ≥2 standard visual acuity rows) or the test could not be completed due to the non-cooperation of the subject, it was concluded that the test was not cooperated and the visual acuity 6 was false. If, although the difference between the visual acuity 3, the visual acuity 4, the visual acuity 5 and the visual acuity 6 obtained by the 4 tests was less than 2 standard visual acuity rows (i.e. <2 standard visual acuity rows), the subject correctly identified the first type of optotype in the heterogeneous visual acuity chart but failed to correctly identify the second type of optotype, or the visual acuity results obtained with two different test distances in one test of the heterogeneous visual acuity chart could not be explained reasonably, or there was a contradiction between these visual acuities that could not be explained reasonably, it was concluded that the subject was likely to be subjectively uncooperative and the visual acuity 6 was likely to be false. The conclusion on the authenticity of the visual acuity 6 was recorded.

S8. The subject was required to show a true visual acuity. The first tester tested the true visual acuity of the subject with the standard logarithmic visual acuity chart, which was denoted as a visual acuity 7.

According to the visual acuity 1, the visual acuity 2 and the visual acuity 7, the determination conclusion of the visual acuity 6 was verified. The test results are shown in Table 2.

TABLE 2

Visual Acuity Test Results

| | First Tester | | Second Tester | | | | | Second Tester | |
|---|---|---|---|---|---|---|---|---|---|
| No. | Visual Acuity 1 | Visual Acuity 2 | Visual Acuity 3 | Visual Acuity 4 | Visual Acuity 5 | | Visual Acuity 6 and Determination | | Visual Acuity 7 | Description |

| No. | V1 | V2 | V3 | V4 | V5a | V5b | V6 | Det. | V7 | Description |
|---|---|---|---|---|---|---|---|---|---|---|
| 1 | 0.5 | 0.2 | 0.356 | <0.418 | 0.424 | 0.305 | <0.342 | 0.25 | False | 0.5 | |
| 2 | 1.2 | 1.2 | 1.0 | 1.172 | 1.330 | — | — | 1.2 | True | 1.2 | To be retested, No. 77 |
| 3 | 1.0 | 0.25 | 0.323 | 0.379 | 0.434 | <0.278 | 0.311 | 0.25 | False | 1.0 | |
| 4 | 1.2 | 0.6 | 0.6 | <0.716 | 0.376 | 0.544 | <0.604 | 0.6 | False | 1.2 | |
| 5 | 0.6 | 0.25 | 0.168 | <0.198 | 0.17 | 0.204 | <0.240 | 0.2 | Suspicious | 0.6 | |
| 6 | 0.8 | 0.8 | 0.654 | 0.768 | 0.81 | 0.891 | <0.989 | 0.8 | True | 1.0 | |
| 7 | 0.3 | 0.1 | 0.074 | 0.083 | 0.12 | 0.24 | <0.266 | 0.1 | False | 0.3 | |
| 8 | 0.6 | 0.6 | 0.53 | 0.623 | 0.592 | 0.505 | 0.606 | 0.5 | True | 0.6 | |
| 9 | 1.0 | 0.5 | 0.768 | <0.859 | 0.968 | 0.747 | 0.829 | 0.5 | False | 1.0 | |
| 10 | 0.8 | 0.5 | 0.307 | <0.341 | 0.326 | <0.12 | 0.134 | 0.3 | False | 0.8 | |
| 11 | 1.0 | 0.4 | <0.428 | 0.503 | 0.415 | 0.595 | 0.661 | 0.5 | False | 1.2 | |
| 12 | 1.2 | 0.5 | 0.72 | <0.799 | 0.586 | 0.582 | <0.652 | 0.5 | Suspicious | 1.2 | Not to be retested |
| 13 | 0.5 | 0.2 | 0.573 | <0.642 | 0.684 | 0.507 | <0.563 | 0.2 | False | 0.8 | |
| 14 | 1.0 | 0.2 | 0.438 | 0.487 | 0.354 | 0.32 | <0.358 | 0.15 | False | 1.2 | |
| 15 | 1.2 | 1.2 | 1.2 | <1.34 | 1.27 | — | — | 1.2 | True | 1.2 | |
| 16 | 0.8 | 1.2 | 1.043 | 1.158 | 0.878 | 0.94 | 1.01 | 1.2 | False | 1.0 | |
| 17 | 0.8 | 0.8 | <0.890 | 0.987 | 0.828 | 0.672 | 0.746 | 0.8 | Suspicious | 0.8 | Not to be retested, poor subjective cooperation |
| 18 | 0.8 | 0.3 | <0.204 | 0.24 | 0.346 | 0.225 | <0.250 | 0.3 | False | 0.8 | |
| 19 | 1.2 | 0.6 | 0.39 | 0.433 | 0.377 | Untestable | | 0.4 | False | 1.2 | |
| 20 | 0.5 | 0.2 | 0.24 | <0.282 | 0.256 | 0.2 | 0.224 | 0.2 | True× | 0.5 | Feign through ambiguity |
| 21 | 1.0 | 0.25 | 0.499 | <0.554 | 0.435 | 0.292 | <0.325 | 0.25 | False | 1.0 | |
| 22 | 0.5 | 0.1 | <0.283 | 0.333 | 0.282 | 0.202 | <0.225 | 0.1 | False | 0.5 | |
| 23 | 1.0 | 0.5 | 0.552 | <0.613 | 0.6 | 0.3 | <0.356 | 0.5 | False | 1.2 | To be retested, No. 67 |
| 24 | 0.8 | 0.4 | 0.522 | 0.609 | 0.678 | 0.474 | <0.527 | 0.4 | False | 0.8 | |
| 25 | 1.2 | 0.3 | 0.291 | <0.323 | 0.276 | 0.218 | 0.242 | 0.3 | False | 1.2 | |
| 26 | 1.2 | 0.6 | <0.444 | <0.522 | 0.5648 | 0.45 | 0.503 | 0.6 | False | 1.2 | |
| 27 | 0.8 | 0.4 | <0.364 | 0.408 | 0.546 | <0.220 | 0.259 | 0.3 | False | 0.8 | |
| 28 | 1.0 | 0.2 | 0.381 | <0.423 | 0.31 | 0.174 | <0.205 | 0.2 | False | 1.2 | |
| 29 | 1.2 | 0.25 | 0.619 | <0.728 | 0.574 | 0.218 | <0.257 | 0.4 | False | 1.2 | |
| 30 | 1.2 | 0.5 | 0.76 | <0.844 | 0.821 | 0.334 | <0.393 | 0.5 | False | 1.5 | To be retested, No. 71 |
| 31 | 0.8 | 0.1 | 0.115 | <0.126 | 0.126 | 0.072 | <0.085 | 0.1 | False | 0.6 | |
| 32 | 1.0 | 0.4 | 0.33 | <0.389 | 0.604 | 0.416 | 0.463 | 0.4 | False | 1.0 | |
| 33 | 1.0 | 0.4 | 0.404 | <0.452 | 0.562 | 0.394 | <0.433 | 0.4 | Suspicious | 1.0 | Not to be retested |
| 34 | 0.8 | 0.25 | 0.522 | <0.584 | 0.644 | 0.588 | <0.657 | 0.25 | False | 0.8 | |
| 35 | 1.0 | 0.25 | 0.272 | <0.305 | 0.396 | 0.496 | <0.551 | 0.2 | False | 1.0 | |
| 36 | 1.0 | 0.25 | 0.188 | <0.222 | 0.334 | 0.404 | <0.452 | 0.3 | False | 1.2 | |
| 37 | 0.8 | 0.25 | 0.36 | <0.400 | 0.427 | 0.239 | <0.281 | 0.25 | False | 0.8 | |
| 38 | 1.5 | 0.25 | 0.146 | <0.164 | 0.116 | 0.195 | <0.217 | 0.25 | False | 1.5 | |
| 39 | 1.5 | 0.5 | 0.407 | <0.453 | 0.5676 | 0.437 | <0.485 | 0.5 | False | 1.5 | Retested, 0.835 |
| 40 | 1.2 | 0.4 | 0.353 | <0.456 | 0.527 | 0.361 | <0.424 | 0.4 | False | 1.2 | |
| 41 | 0.6 | 0.25 | 0.322 | <0.361 | 0.464 | 0.208 | <0.245 | 0.25 | False | 0.8 | |
| 42 | 1.5 | 0.25 | <0.367 | 0.431 | 0.516 | 0.243 | <0.271 | 0.25 | False | 1.5 | |
| 43 | 0.3 | 0.6 | Untestable | | 0.705 | Untestable | | 0.6 | False/invalid | 0.8 | Visual acuity 1 false, invalid experiment |
| 44 | 0.6 | 0.25 | 0.52 | <0.582 | 0.416 | 0.271 | <0.298 | 0.25 | False | 0.6 | |
| 45 | 0.5 | 0.25 | 0.244 | <0.286 | 0.295 | 0.254 | <0.300 | 0.25 | Suspicious | 0.6 | Not to be retested |
| 46 | 1.2 | 2 | 1.296 | 1.449 | 1.308 | — | — | 2.56 | False | 1.5 | |
| 47 | 0.5 | 0.25 | <0.343 | 0.403 | 0.488 | <0.256 | 0.270 | 0.2 | False | 0.4 | |
| 48 | 1.0 | 0.6 | <0.400 | 0.405 | 0.629 | 0.403 | <0.448 | 0.15 | False | 0.8 | |
| 49 | 0.4 | 0.15 | <0.227 | 0.254 | 0.454 | 0.187 | <0.220 | 0.15 | False | 0.4 | |
| 50 | 1.0 | 0.4 | 0.303 | <0.357 | 0.534 | 0.338 | <0.373 | 0.4 | False | 1.0 | |
| 51 | 0.3 | 0.12 | 0.186 | <0.208 | 0.170 | <0.076 | 0.090 | 0.2 | False | 0.3 | |

TABLE 2-continued

Visual Acuity Test Results

| | First Tester | | Second Tester | | | | | Second Tester | |
|---|---|---|---|---|---|---|---|---|---|
| No. | Visual Acuity 1 | Visual Acuity 2 | Visual Acuity 3 | Visual Acuity 4 | Visual Acuity 5 | | Visual Acuity 6 and Determination | | Visual Acuity 7 | Description |
| 52 | 0.5 | 0.2 | <0.173 | 0.191 | 0.188 | 0.192 | <0.214 | 0.2 | False | 0.6 | Retested, 0.315 |
| 53 | 1.0 | 0.25 | 0.185 | <0.206 | 0.260 | 0.219 | <0.243 | 0.25 | False | 1.0 | |
| 54 | 0.8 | 0.3 | 0.315 | <0.353 | 0.7 | 0.614 | <0.687 | 0.3 | False | 0.6 | |
| 55 | 0.8 | 0.3 | 0.302 | <0.338 | 0.453 | 0.322 | <0.360 | 0.3 | False | 0.8 | Retested, 0.659 |
| 56 | 1.0 | 0.4 | 0.238 | <0.279 | 0.563 | 0.403 | <0.448 | 0.3 | False | 1.0 | |
| 57 | 1.2 | 0.12 | 0.162 | <0.180 | 0.208 | 0.194 | <0.228 | 0.15 | False | 1.2 | Retested, 0.336, <0.376 |
| 58 | 0.8 | 0.3 | 0.307 | <0.341 | 0.384 | 0.304 | <0.340 | 0.3 | True× | 0.8 | Retested, 0.316, <0.426, 0.25 |
| 59 | 1.0 | 0.3 | 0.337 | <0.422 | 0.479 | <0.232 | 0.273 | 0.5 | False | 0.8 | |
| 60 | 1.2 | 0.4 | 0.248 | <0.292 | 0.678 | 0.207 | <0.244 | 0.3 | False | 1.0 | |
| 61 | 1.2 | 0.2 | 0.356 | <0.398 | 0.613 | <0.216 | <0.2545 | 0.2 | False | 1.2 | |
| 62 | 0.4 | 0.1 | <0.160 | 0.178. | 0.256 | <0.246 | 0.289 | 0.1 | False | 0.4 | |
| 63 | 1.0 | 0.12 | 0.136 | <0.144 | 0.401 | 0.228 | <0.268 | 0.12 | False | 1.2 | |
| 64 | 1.0 | 0.12 | 0.472 | <0.528 | 0.365 | <0.352 | 0.364 | 0.12 | False | 1.0 | |
| 65 | 1.2 | 0.5 | 0.268 | <0.298 | 0.434 | <0.392 | 0.4156 | 0.5 | False | 1.2 | |
| 66 | 1.2 | 0.2 | 0.188 | <0.209 | 0.410 | 0.094 | <0.106 | 0.15 | False | 1.2 | |
| 67 | 1.2 | 0.5 | 0.332 | <0.369 | 0.649 | <0.36 | 0.423 | 0.5 | False | 1.2 | No. 23 volunteer |
| 68 | 1.2 | 0.3 | <0.245 | 0.288 | 0.345 | <0.429 | 0.436 | 0.4 | False | 1.2 | |
| 69 | 0.5 | 0.2 | <0.19 | 0.213 | 0.323 | 0.134 | <0.149 | 0.25 | False | 0.6 | |
| 70 | 0.5 | 0.2 | 0.419 | <0.469 | 0.588 | 0.27 | <0.301 | 0.2 | False | 0.5 | |
| 71 | 1.0 | 1.5 | 1.260 | <1.410 | 1.236 | 1 | <1.118 | 2 | False | 1.0 | No. 30 volunteer |
| 72 | 0.8 | 0.25 | <0.260 | 0.291 | 0.425 | 0.4 | <0.447 | 0.3 | False | 0.8 | |
| 73 | 1.2 | 0.5 | 0.468 | <0.524 | 0.698 | 0.362 | <0.403 | 0.5 | False | 1.2 | |
| 74 | 0.6 | 1.0 | 0.601 | <0.706 | 0.878 | 0.8 | <0.888 | 1.0 | False/invalid | 0.8 | Visual acuity 1 false, invalid experiment |
| 75 | 0.8 | 0.25 | 0.280 | 0.315 | 0.419 | <0.268 | <0.305 | 0.25 | False | 0.8 | |
| 76 | 0.6 | 0.25 | <0.289 | 0.324 | 0.222 | 0.198 | <0.234 | 0.25 | False | 0.6 | |
| 77 | 1.0 | 2.0 | 1.032 | <1.145 | 1.2 | 1.2 | <1.34 | 2 | False | 0.8 | No. 2 volunteer |
| 78 | 1.0 | 0.6 | 0.550 | <0.616 | 0.528 | 0.413 | <0.485 | 0.6 | False | 1.0 | |
| 79 | 1.2 | 0.6 | 0.542 | <0.602 | 0.602 | 0.48 | <0.538 | 0.6 | False | 1.2 | Tester, retested, 0.808 |
| 80 | 1.2 | 0.5 | 0.472 | <0.524 | 0.406 | 0.49 | <0.545 | 0.5 | False | 1.2 | Tester, retested, 0.666, <0.702 |
| 81 | 0.8 | 0.15 | 0.132 | <0.148 | 0.233 | 0.074 | <0.088 | 0.15 | False | 0.8 | Tester, binocular |

Referring to Table 2, it can be seen from the experimental results that the subjects No. 16, No. 43 and No. 74 did not show their true visual acuities, and the experiment on these 3 cases was invalid. There were 78 valid cases.

Among the 78 cases, 2 cases were incorrectly concluded, with an incorrect conclusion rate of 2.56%. There were 5 true cases. Among them, 4 cases were correctly identified, and 1 case, No. 17, who identified the small-sized optotype but failed to identify the large-sized optotype in the heterogeneous visual acuity chart, was identified as suspicious. There were 4 cases of feigned high visual acuities, all of which were identified. There were 7 volunteers who gave up feigning high visual acuities after understanding the testing method. There were 70 cases of feigned low visual acuities. Among them, 68 cases were identified, with an identification rate of 97.1%, and 2 cases, that is, No. 20 and No. 58, were incorrectly identified as false.

25 (35.7%) subjects feigning low visual acuities for 29 times showed abnormal identification on the optotype sizes, that is, they identified the small-sized optotype but failed to identify the large-sized optotype in the heterogeneous visual acuity chart. 17 subjects (24.2%) feigning low visual acuities for 19 times produced two visual acuity results from different test distances, which could not be explained reasonably, in a test with the heterogeneous visual acuity chart. For example, the subject No. 32, with a visual acuity 5, correctly identified 3 or more 0.4 and 0.445 optotypes at 5.2 m but failed to correctly identify 0.4 and 0.445 optotypes at 5.5 m, showing visual acuities 0.416 and 0.463, <0.439 and <0.490. The abnormal identification cases totaled 38 among those who feigning low visual acuities, 38/70, 54.3%.

No abnormal identification was found among those feigning high visual acuities. Only 1 case of true visual acuity (No. 17) was identified abnormal due to the wild guess and poor cooperation of the subject.

Among those feigning low visual acuities, there were 4 suspicious cases whose test results contradicted but could not be explained reasonably. For example, the total visual acuity difference of the subject No. 5 was within one standard visual acuity row, but the test results of the subject were contradictory in that the visual acuity 3 denied the identification of 0.198, which was inconsistent with the visual acuity 5 and the visual acuity 6. In fact, the subject No. 5 was a female, 22 years old, and a fourth-year university student. She worn 300-degree myopia glasses, with the degree of astigmatism unknown and uncorrected. According to the subject No. 5, the 0.2 optotype was clear, the 0.25 optotype was slightly blurred, and the 0.3, 0.4 and 0.5 optotypes were more blurred. She feigned a low visual acuity based on the degree of blur. The experimental program was adjusted for those after No. 50. For suspicious visual acuities that could not be explained reasonably, the subjects were retested once with the heterogeneous visual acuity chart or the single visual acuity chart test. Therefore, no suspicious cases were found among the subjects after No. 50.

The 2 incorrectly concluded cases came from those feigning low visual acuities, with their test results showing the visual acuity difference ≤1 standard visual acuity row. The subject No. 20 was female, 19 years old, and a second-year university student. She had astigmatism in her right eye, the degree of which was unknown and not corrected, and she did not usually wear glasses. The subject No. 20 stated that she could rely on the degree of astigmatism to identify the 0.2 optotype so as to feign a low visual acuity. The subject No. 58 was a male, 24 years old, and a graduate student majoring in computer image processing. He stated that he could identify the size of the optotype, but his method was unknown.

Volunteers No. 67, No. 71 and No. 77 participated in the experiment for the second time. Volunteers No. 79, No. 80 and No. 81, who were testers of this experiment, also participated in the experiment as subjects. They were familiarity with the testing methods and procedures but their test results were not affected.

Excluding the 2 invalid cases and 5 true cases, there were 73 valid cases in the identification of feigned low visual acuities. Among them, the test results with the heterogeneous visual acuity chart (visual acuity 3) and the standard logarithmic visual acuity chart (visual acuity 6) showed that, there were 33 cases having a visual acuity difference of more than 2 standard rows, with an identification rate of 45.2%. By comparing the two test results (visual acuity 3 and visual acuity 5) with the heterogeneous visual acuity chart, there were 48 cases having a visual acuity difference of more than 2 standard rows, with an identification rate of 65.8%.

In the above experiment, the subjects were tested by using the visual acuity testing device. The identification rate of true visual acuities reached 95% and above. The present disclosure can effectively discover subjective non-cooperation and feigned high visual acuities, and provide evidence support for social issues involving social security, personal injury insurance claims, etc. so as to prevent those who feign from obtaining improper benefits. The present disclosure has very important practical significance.

Experiment:

Subjects: 25 volunteers, age: 19-25, male or female, education level: high school or above, who were clear about the purpose and procedures of the experiment, and were willing to actively cooperate with the experiment. The test distance was 2-7 m. The relationship between the decimal visual acuity, the optotype and the test distance was:

Visual acuity=optotype visual acuity×test distance/5

As shown in FIG. 1, the single visual acuity chart is composed of five optotypes.

The relationship between the optotypes and the visual acuities of each visual acuity chart is shown in Table 1.

TABLE 1

| 5-Grade Visual Acuity | Visual Angle $\alpha$ (') | Design Distance D (m) | Side Length of Optotype (mm) | Decimal Visual Acuity V |
|---|---|---|---|---|
| 5-lg$\alpha$ | $10''$ | $5\alpha$ | $5 \times 5{,}000\ \alpha\rho$ | $1/\alpha$ |

In Table 1, $\rho$ is a mathematical symbol, the number of radians of 1', being $2.90888 \times 10^{-4}$ rad.

Two testers were assigned to test by using the above visual acuity testing device according to the following steps in sequence:

S1. A first tester tested a true visual acuity of a subject with the standard logarithmic visual acuity chart, which was denoted as a visual acuity 1.

S2. The subject independently chose to feign or not to feign his visual acuity. If the subject chose to feign, the subject decreased or increased his true visual acuity by more than 2 rows. The feigning succeeded if the test of the feigned visual acuity could be repeated. The first tester tested the true or feigned visual acuity of the subject with the standard logarithmic visual acuity chart, which was denoted as a visual acuity 2. If the subject chose to feign, the subject was informed of the change of the tester. During the test by the second tester, the subject maintained the feigned visual acuity. If it was found that the subject did not cooperate, it meant that the feigning failed.

The feigning was aided by a reprint of the standard logarithmic visual acuity chart posted in front of the subject.

S3. The visual acuity chart was replaced with the single visual acuity chart, and the second tester continued the visual acuity test on the subject with the single visual acuity chart. The single visual acuity chart was moved from 7 m to the subject until a farthest distance at which the subject correctly identified 3 optotypes or more. The visual acuity was calculated and recorded, which was denoted as a visual acuity 3.

S4. The visual acuity chart was replaced with the standard logarithmic visual acuity chart, and the second tester continued the visual acuity test on the subject with the standard logarithmic visual acuity chart. A visual acuity was recorded, which was denoted as a visual acuity 4.

S5. The second tester independently determined the authenticity of the visual acuity 4. Specifically, the authenticity of the visual acuity was determined as follows. If the difference between the visual acuity 3 obtained by the test of step S3 and the visual acuity 4 obtained by the test of step S4 reached 2 standard visual acuity rows or more (i.e. ≥2 standard visual acuity rows), it was concluded that the test was not cooperated and the visual acuity 4 was false. The conclusion on the visual acuity 4 was recorded.

S6. The subject was required to show a true visual acuity. The first tester tested the true visual acuity of the subject with the standard logarithmic visual acuity chart, which was denoted as a visual acuity 5.

According to the visual acuity 1, the visual acuity 2 and the visual acuity 5, the determination conclusion of the visual acuity 4 was evaluated.

TABLE 2

Visual Acuity Test Results

| Subject No. | First Tester | | Second Tester | | First Tester |
|---|---|---|---|---|---|
| | Visual Acuity 1 | Visual Acuity 2 | Visual Acuity 3 | Visual Acuity 4/ Determination | | Visual Acuity 5 |
| 1 | 0.5 | 0.2 | 0.42 | 0.25 | False | 0.5 |
| 2 | 1.2 | 1.2 | 1.33 | 1.2 | | 1.2 |
| 3 | 1.0 | 0.25 | 0.43 | 0.25 | False | 1.0 |
| 4 | 1.2 | 0.6 | 0.38 | 0.6 | False | 1.2 |
| 5 | 0.6 | 0.25 | 0.17 | 0.2 | | 0.6 |
| 6 | 0.8 | 0.8 | 0.81 | 0.8 | | 1.0 |
| 7 | 0.3 | 0.1 | 0.12 | 0.1 | | 0.3 |
| 8 | 0.6 | 0.6 | 0.59 | 0.5 | | 0.6 |
| 9 | 1.0 | 0.5 | 0.97 | 0.5 | False | 1.0 |
| 10 | 0.8 | 0.5 | 0.33 | 0.3 | | 0.8 |
| 11 | 1.0 | 0.4 | 0.42 | 0.5 | | 1.2 |
| 12 | 1.2 | 0.5 | 0.59 | 0.5 | | 1.2 |
| 13 | 0.5 | 0.2 | 0.68 | 0.2 | False | 0.8 |
| 14 | 1.0 | 0.2 | 0.35 | 0.15 | False | 1.2 |
| 15 | 1.2 | 1.2 | 1.27 | 1.2 | | 1.2 |
| 16 | 0.8 | 1.2 | 0.88 | 1.2 | False | 1.0 |
| 17 | 0.8 | 0.8 | 0.83 | 0.8 | | 0.8 |
| 18 | 0.8 | 0.3 | 0.35 | 0.3 | | 0.8 |
| 19 | 1.2 | 0.6 | 0.38 | 0.4 | | 1.2 |
| 20 | 0.5 | 0.2 | 0.26 | 0.2 | | 0.5 |
| 21 | 1.0 | 0.25 | 0.44 | 0.25 | False | 1.0 |
| 22 | 0.5 | 0.1 | 0.28 | 0.1 | False | 0.5 |
| 23 | 1.0 | 0.5 | 0.60 | 0.5 | | 1.2 |
| 24 | 1.2 | 2.0 | 1.31 | 2.0 | False | 1.0 |
| 25 | 1.2 | 0.3 | 0.28 | 0.3 | | 1.2 |

Referring to Table 2, it can be seen from the experimental results that among the 25 experimental samples, there were 5 cases of true visual acuities, and the difference between the visual acuity 3 and the visual acuity 4 was within one standard visual acuity row. 10 cases of false visual acuities all came from feigned visual acuities, with an identification rate of 100%.

Among 20 cases of feigned visual acuities, 10 cases were identified to be false, with an identification rate of 50%. 2 cases of feigned high visual acuities were identified, with an identification rate of 100%. Among 18 cases of feigned low visual acuities, 8 cases were identified, with an identification rate of 44.4%. 10 cases of feigned low visual acuities were not identified, where the difference between the visual acuity 3 and the visual acuity 4 was within one standard visual acuity row.

In the above experiment, the subjects were tested with the single visual acuity chart by using the visual acuity testing device and method. The identification rate of feigned visual acuities was about 50%, where the identification rate of feigned high visual acuities was 100%, and the identification rate of feigned low visual acuities was about 44%. The present disclosure can effectively discover subjective non-cooperation and feigned high visual acuities, and provide evidence support for social issues involving social security, personal injury insurance claims, etc., so as to prevent those who feign from obtaining improper benefits. The present disclosure has very important practical significance.

The above embodiments are intended to explain the present disclosure, rather than to limit the present disclosure. Any modifications and changes made to the present disclosure within the spirit and the protection scope defined by the claims should all fall within the protection scope of the present disclosure.

The above embodiments are intended to explain the present disclosure, rather than to limit the present disclosure. Any modifications and changes made to the present disclosure within the spirit and the protection scope defined by the claims should all fall within the protection scope of the present disclosure.

What is claimed is:

1. A heterogeneous visual acuity chart, wherein the heterogeneous visual acuity chart is a size illusion chart composed of a heterogeneous reference zone and at least two types of optotypes of different sizes; and the heterogeneous reference zone is used to cause an incorrect identification on the at least two types of optotypes of different sizes, and the incorrect identification is to make a small-sized optotype visually appear not to be smaller than a large-sized optotype.

2. The heterogeneous visual acuity chart according to claim 1, wherein the heterogeneous reference zone is a perspective affecting a visual depth of the at least two types of optotypes of different sizes; M large-sized optotypes are provided in visually nearer positions in the perspective, and N small-sized optotypes are provided in visually farther positions in the perspective, M and N being positive integers ≥1; and the incorrect identification on the at least two types of optotypes of different sizes is caused by causing an illusion on the visual depth.

3. The heterogeneous visual acuity chart according to claim 2, wherein the heterogeneous reference zone further comprises an illusion pattern making the small-sized optotype visually larger and the large-sized optotype visually smaller; and the illusion pattern comprises one or more of a letter pattern, a number pattern, a geometric structure pattern and a cone.

4. The heterogeneous visual acuity chart according to claim 3, wherein the letter pattern is an optotype pattern with a same structure as each of the small-sized optotype and the large-sized optotype.

5. The heterogeneous visual acuity chart according to claim 4, wherein a color block is further provided between two different sets of optotypes in the heterogeneous reference zone.

6. The heterogeneous visual acuity chart according to claim 5, wherein when there are two types of optotypes, a plurality of small-sized optotypes are contained in a first type of the two types of optotypes, and a plurality of large-sized optotypes are contained in a second type of the two types of optotypes; a size of each of the plurality of small-sized optotypes in the first type is 0.64-0.99 times a size of each of the plurality of large-sized optotypes in the second type; a blank distance between each optotype of the plurality of small-sized optotypes in the first type and the plurality of large-sized optotypes in the second type and a surrounding line or pattern forming the heterogeneous reference zone is more than half of a width of the each optotype; a blank distance between two adjacent optotypes of the two types of optotypes is more than half of a width of each the plurality of large-sized optotypes; and there are at least five optotypes in four directions in each of the two types of optotypes, and directions of the two adjacent optotypes are different.

7. The heterogeneous visual acuity chart according to claim 6, wherein the heterogeneous reference zone comprises a first type of optotype pattern and a second type of optotype pattern, the first type of optotype pattern and the second type of optotype pattern have the same structure as each of the small-sized optotype and the large-sized optotype; the first type of optotype pattern and the second type of optotype pattern are respectively provided around the first type of optotypes and the second type of optotypes; a size of the first type of optotype pattern is not more than 0.5 times a size of the first type of optotypes, and a size of the second type of optotype pattern is not less than 1.5 times a size of the second type of optotypes; an Ebbinghaus illusion is caused to make the first type of optotypes appear larger visually and the second type of optotypes appear smaller visually, so as to affect a normal identification on a size of the first type of optotypes and a size of the second type of optotypes; when the illusion pattern comprises the cone, the cone is provided between the two types of optotypes; and an apex of the cone is near the first type of optotypes, and a bottom surface of the cone is near the second type of optotypes.

8. The heterogeneous visual acuity chart according to claim 7, wherein the size of the first type of optotypes is 0.79-0.81 times the size of the second type of optotypes.

9. A visual acuity testing method according to claim 1, comprising the following steps:
performing a visual acuity test with the heterogeneous visual acuity chart; moving a testing heterogeneous visual acuity chart from far to near or from near to far relative to a subject so as to change a test distance between the subject and the testing heterogeneous visual acuity chart, until a number of optotypes, correctly identified by the subject, in any set of optotypes is less than half; and recording the number of correctly identified optotypes in each of the at least two types of optotypes in the heterogeneous visual acuity chart, calculating and recording a first tested visual acuity;
performing a standard visual acuity test with a standard logarithmic visual acuity chart, wherein the subject is in the test distance from a testing standard logarithmic visual acuity chart, and recording a second tested visual acuity; and
testing with the heterogeneous visual acuity chart for ≥1 time for the subject, and determining whether a visual acuity of the subject is true according to a difference between visual acuities tested with the heterogeneous visual acuity chart and a difference between visual acuities tested with the heterogeneous visual acuity chart and the standard logarithmic visual acuity chart.

10. The visual acuity testing method according to claim 9, wherein the visual acuity testing method further comprises: performing a visual acuity test with a single visual acuity chart; moving a testing single visual acuity chart relative to the subject from far to near so as to change the test distance between the subject and the testing single visual acuity chart, until a farthest distance where the subject correctly identifies more than half of the optotypes; and calculating and recording a third tested visual acuity;
wherein the single visual acuity chart is a plan composed of at least five optotypes of a same size; there are four optotype directions in the single visual acuity chart; a blank distance between two adjacent optotypes of the single visual acuity chart is more than half of a width of each of the optotypes; and directions of two adjacent optotypes in a vertical direction are different, and directions of two adjacent optotypes in a horizontal direction are also different; and
testing with the heterogeneous visual acuity chart and the single visual acuity chart each for ≥1 time for the subject, and determining whether the visual acuity of the subject is true according to the difference between the visual acuities tested with the heterogeneous visual acuity chart, a difference between visual acuities tested with the single visual acuity chart, a difference between visual acuities tested with the heterogeneous visual acuity chart and the single visual acuity chart, the difference between the visual acuities tested with the heterogeneous visual acuity chart and the standard logarithmic visual acuity chart, and a difference between visual acuities tested with the single visual acuity chart and the standard logarithmic visual acuity chart.

11. The visual acuity testing method according to claim 9, wherein the determining whether the visual acuity of the subject is true comprises:
defining a row of the standard logarithmic visual acuity chart as a standard visual acuity row;
determining that a visual acuity tested with the standard logarithmic visual acuity chart is true if the differences are all within one standard visual acuity row, that is, the differences ≤1 standard visual acuity row;
determining that the subject is uncooperative and the visual acuity tested with the standard logarithmic visual acuity chart is false, if one of the differences reaches two standard visual acuity rows or more, that is, the difference ≥2 standard visual acuity rows, or the subject does not cooperate to complete the visual acuity test; and
determining that the subject is likely to be subjectively uncooperative and the visual acuity tested with the standard logarithmic visual acuity chart is likely to be false, if, although the differences do not reach two standard visual acuity rows, when tested with the heterogeneous visual acuity chart, the subject correctly identifies an optotype in the first type but fails to correctly identify an optotype in the second type, or there is a contradiction hard to be explained reasonably between the tested visual acuities.

12. The visual acuity testing method according to claim 11, wherein in each visual acuity test, there are a same number of optotypes of each type in the standard logarithmic visual acuity chart, the heterogeneous visual acuity chart and the single visual acuity chart.

13. The visual acuity testing method according to claim 11, wherein in each visual acuity test, optotype directions in each visual acuity chart of the standard logarithmic visual acuity chart, the heterogeneous visual acuity chart and the single visual acuity chart are changed manually or automatically, so as to make the optotype directions in the each visual acuity chart different in each visual acuity test.

14. The visual acuity testing method according to claim 11, wherein an optotype size difference in each visual acuity test exceeds one standard visual acuity row, and two adjacent visual acuity tests are performed with different visual acuity charts.

15. A visual acuity testing device corresponding to the visual acuity testing method according to claim 10, comprising a distance measuring device, a visual acuity chart mounting and adjustment device and a visual acuity chart support device, wherein the visual acuity chart mounting and adjustment device is fixed on the visual acuity chart support device for changing and displaying different visual acuity charts; the distance measuring device is used to measure a distance between the subject and a testing visual acuity chart; the testing visual acuity chart is defined by each visual acuity chart of the heterogeneous visual acuity chart, the standard logarithmic visual acuity chart and the single visual acuity chart or an image of the each visual acuity chart in a mirror.

16. The visual acuity testing device according to claim 15, wherein the visual acuity chart support device is a first support device; the each visual acuity chart is detachably mounted on a support plate of the first support device; and the each visual acuity chart serves as the testing visual acuity chart.

17. The visual acuity testing device according to claim 15, wherein the visual acuity testing device further comprises a second support device and the mirror; the visual acuity chart support device is a first support device; the each visual acuity chart is detachably mounted on a support plate of the first support device; the first support device is provided opposite to the second support device; the mirror is mounted on the second support device, such that the mirror is opposite to the heterogeneous visual acuity chart or the standard logarithmic visual acuity chart; and the testing visual acuity chart is defined by an image of the each visual acuity chart in the mirror.

18. The visual acuity testing device according to claim 16, wherein the visual acuity testing device further comprises a moving device, and the moving device is used to realize a relative movement between the testing visual acuity chart and the subject.

19. The visual acuity testing device according to claim 15, wherein the visual acuity chart support device is a first support device; the visual acuity chart mounting and adjustment device comprises a control unit, a visual acuity chart display screen and a visual acuity result display screen, the visual acuity chart display screen and the visual acuity result display screen are connected to the control unit; the visual acuity chart display screen is mounted on the first support device; the control unit is provided with a data storage module, a visual acuity chart selection module, a heterogeneous visual acuity chart generation module for generating the heterogeneous visual acuity chart, a standard visual acuity chart generation module for generating the standard logarithmic visual acuity chart, a single visual acuity chart generation module for generating the single visual acuity chart and a visual acuity calculation module for calculating a visual acuity; the visual acuity calculation module, the visual acuity chart selection module, the heterogeneous visual acuity chart generation module, the single visual acuity chart generation module and the standard visual acuity chart generation module are respectively connected to the data storage module; and the testing visual acuity chart is a visual acuity chart generated in the visual acuity chart display screen.

20. The visual acuity testing device according to claim 19, wherein the distance measuring device is a displacement sensor mounted on the first support device and connected to the control unit.

21. The visual acuity testing device according to claim 20, wherein the visual acuity testing device further comprises a smart moving device, an optotype indicating module and an optotype identifying device; the smart moving device comprises a wheel at a bottom of the first support device, a drive motor connected to the wheel and a brake on the wheel; the drive motor and the brake are respectively connected to a drive module in the control unit; the optotype indicating module is used to indicate optotypes to be identified by the subject; the optotype identifying device is used to confirm a start of identifying the optotypes and input an identification result of the optotypes to be identified; and the drive module, the optotype indicating module and the optotype identifying device are respectively connected to the data storage module.

22. The visual acuity testing device according to claim 21, wherein the control unit further comprises a feigned visual acuity determination module; the feigned visual acuity determination module is connected to the data storage module; and the feigned visual acuity determination module is used to obtain the visual acuities tested with the single visual acuity chart, the heterogeneous visual acuity chart and the standard logarithmic visual acuity chart from the data storage module, compare multiple visual acuities to determine whether a visual acuity is false, send a determination result to the data storage module for storage, and send the determination result of the subject to the visual acuity result display screen for display.

23. The visual acuity testing device according to claim 22, wherein the control unit further comprises an optotype size setting module for setting optotype sizes; the optotype size setting module is connected to the heterogeneous visual acuity chart generation module, the single visual acuity chart generation module and the standard visual acuity chart generation module, respectively; the control unit further comprises an optotype direction setting module for setting optotype directions; the optotype direction setting module is connected to the heterogeneous visual acuity chart generation module, the single visual acuity chart generation module and the standard visual acuity chart generation module, respectively; the control unit further comprises an optotype arrangement setting module for arranging optotype positions; and the optotype arrangement setting module is connected to the heterogeneous visual acuity chart generation module, the single visual acuity chart generation module and the standard visual acuity chart generation module, respectively.

* * * * *